United States Patent
Lo et al.

(10) Patent No.: US 9,028,436 B2
(45) Date of Patent: May 12, 2015

(54) HEMODIALYSIS SYSTEM WITH CASSETTE-BASED BLOOD AND DIALYSTE PUMPING

(75) Inventors: Ying-Cheng Lo, Green Oaks, IL (US); Robert W. Childers, Trinity, FL (US); Thomas D. Kelly, Highland Park, IL (US); Justin Rohde, Des Plaines, IL (US)

(73) Assignees: Baxter International Inc., Deerfield, IL (US); Baxter Healthcare S.A., Glattpark (Opfikon) (CH)

(*) Notice: Subject to any disclaimer, the term of this patent is extended or adjusted under 35 U.S.C. 154(b) by 573 days.

(21) Appl. No.: 13/213,692

(22) Filed: Aug. 19, 2011

(65) Prior Publication Data

US 2011/0303598 A1    Dec. 15, 2011

Related U.S. Application Data

(63) Continuation of application No. 11/530,842, filed on Sep. 11, 2006, now Pat. No. 8,038,639, which is a continuation-in-part of application No. 10/982,170, filed on Nov. 4, 2004, now Pat. No. 8,029,454.

(60) Provisional application No. 60/517,730, filed on Nov. 5, 2003.

(51) Int. Cl.
  *A61M 1/14*      (2006.01)
  *A61M 1/16*      (2006.01)
  (Continued)

(52) U.S. Cl.
  CPC ........... *A61M 1/16* (2013.01); *A61M 2205/127* (2013.01); *A61M 1/28* (2013.01); *A61M 1/34* (2013.01); *A61M 1/1635* (2014.02)

(58) Field of Classification Search
  USPC ............... 604/4.01–5.04, 6.09, 6.11, 6.13
  See application file for complete search history.

(56) References Cited

U.S. PATENT DOCUMENTS

| 3,774,762 | A | 11/1973 | Lichtenstein |
| 3,912,455 | A | 10/1975 | Lichtenstein |

(Continued)

FOREIGN PATENT DOCUMENTS

| DE | 20 02 033 | 8/1970 |
| DE | 29 01 628 | 7/1980 |

(Continued)

OTHER PUBLICATIONS

European Search Report for European Application No. EP 11 18 5090 mailed on Dec. 22, 2011.

(Continued)

*Primary Examiner* — Susan Su
(74) *Attorney, Agent, or Firm* — K&L Gates LLP

(57) ABSTRACT

A hemodialysis system includes: (i) a dialyzer; (ii) a dialysate source; a dialysate pump; (iii) a dialysate cassette operatively connected to the dialysate pump such that the dialysate pump can pump dialysate through the dialysate cassette when the dialysate cassette is in fluid communication with the dialysate source, the dialysate cassette in fluid communication with the dialyzer; (iv) a blood pump; and (v) a blood cassette separate from the dialysate cassette, the blood cassette operatively connected to the blood pump such that the blood pump can pump blood through the blood cassette, the blood cassette including a housing, the housing including a from-patient tube connector, a to-patient tube connector, a saline/priming tube connector, a to-dialyzer tube connector, a from-dialyzer tube connector, and an internal air separation chamber.

23 Claims, 35 Drawing Sheets

(51) Int. Cl.
*A61M 1/28* (2006.01)
*A61M 1/34* (2006.01)

(56) References Cited

U.S. PATENT DOCUMENTS

| | | |
|---|---|---|
| 3,946,731 A | 3/1976 | Lichtenstein |
| 4,161,264 A | 7/1979 | Malmgren et al. |
| 4,190,536 A | 2/1980 | Grimsrud |
| 4,209,391 A | 6/1980 | Landau et al. |
| 4,244,816 A | 1/1981 | Vogler et al. |
| 4,366,061 A | 12/1982 | Papanek et al. |
| 4,386,634 A | 6/1983 | Stasz et al. |
| 4,464,172 A | 8/1984 | Lichtenstein |
| 4,468,329 A | 8/1984 | Shaldon et al. |
| 4,477,342 A | 10/1984 | Allan et al. |
| 4,479,760 A | 10/1984 | Bilstad et al. |
| 4,650,458 A | 3/1987 | Dahlberg et al. |
| 4,676,905 A | 6/1987 | Nagao et al. |
| 4,702,829 A | 10/1987 | Polaschegg et al. |
| 4,708,802 A | 11/1987 | Rath et al. |
| 4,767,399 A | 8/1988 | Bollish |
| 4,770,769 A | 9/1988 | Schael |
| 4,838,865 A | 6/1989 | Flank et al. |
| 5,114,580 A | 5/1992 | Ahmad et al. |
| 5,173,125 A | 12/1992 | Felding |
| 5,221,267 A | 6/1993 | Folden |
| 5,288,463 A | 2/1994 | Chemelli |
| 5,318,556 A | 6/1994 | Avallone et al. |
| 5,324,422 A | 6/1994 | Colleran et al. |
| D350,822 S | 9/1994 | Lanigan |
| D350,823 S | 9/1994 | Lanigan |
| 5,350,357 A | 9/1994 | Kamen et al. |
| D357,312 S | 4/1995 | Riquier et al. |
| 5,421,823 A | 6/1995 | Kamen et al. |
| 5,441,636 A | 8/1995 | Chevallet et al. |
| 5,470,483 A | 11/1995 | Bene et al. |
| 5,522,998 A | 6/1996 | Polaschegg |
| 5,542,919 A | 8/1996 | Simon et al. |
| 5,570,026 A | 10/1996 | Buffaloe, IV et al. |
| 5,614,677 A | 3/1997 | Wansiedler et al. |
| 5,660,722 A | 8/1997 | Nederlof |
| 5,702,597 A | 12/1997 | Chevallet et al. |
| 5,730,712 A | 3/1998 | Falkvall et al. |
| 5,836,908 A | 11/1998 | Beden et al. |
| 5,846,419 A | 12/1998 | Nederlof |
| 5,863,421 A | 1/1999 | Peter, Jr. et al. |
| 5,871,694 A | 2/1999 | Beden et al. |
| 5,919,369 A | 7/1999 | Ash |
| 5,925,011 A | 7/1999 | Faict et al. |
| 5,928,744 A | 7/1999 | Heilmann et al. |
| 5,932,799 A | 8/1999 | Moles |
| 5,989,423 A | 11/1999 | Kamen et al. |
| 6,004,311 A | 12/1999 | Heilmann et al. |
| 6,042,784 A | 3/2000 | Wamsiedler et al. |
| 6,110,384 A | 8/2000 | Goux et al. |
| 6,126,831 A | 10/2000 | Goldau et al. |
| 6,139,748 A | 10/2000 | Ericson et al. |
| 6,210,361 B1 | 4/2001 | Kamen et al. |
| 6,254,567 B1 | 7/2001 | Treu et al. |
| 6,260,715 B1 | 7/2001 | Simard et al. |
| 6,280,632 B1 | 8/2001 | Polaschegg |
| 6,287,516 B1 | 9/2001 | Matson et al. |
| 6,322,551 B1 | 11/2001 | Brugger |
| 6,364,857 B1 | 4/2002 | Gray et al. |
| 6,382,923 B1 | 5/2002 | Gray |
| 6,454,736 B1 | 9/2002 | Ludt et al. |
| 6,484,383 B1 | 11/2002 | Herklotz |
| 6,491,656 B1 | 12/2002 | Morris |
| 6,495,366 B1 | 12/2002 | Briggs |
| 6,531,061 B1 | 3/2003 | Cholewa |
| 6,554,789 B1 | 4/2003 | Brugger et al. |
| 6,572,576 B2 | 6/2003 | Brugger et al. |
| 6,572,641 B2 | 6/2003 | Brugger et al. |
| 6,579,253 B1 | 6/2003 | Burbank et al. |
| 6,582,385 B2 | 6/2003 | Burbank et al. |
| 6,589,482 B1 | 7/2003 | Burbank et al. |
| 6,620,120 B2 | 9/2003 | Landry et al. |
| 6,638,477 B1 | 10/2003 | Treu et al. |
| 6,638,478 B1 | 10/2003 | Treu et al. |
| 6,649,063 B2 | 11/2003 | Brugger et al. |
| 6,663,359 B2 | 12/2003 | Gray |
| 6,702,561 B2 | 3/2004 | Stillig et al. |
| 6,743,201 B1 | 6/2004 | Doenig et al. |
| 6,752,172 B2 | 6/2004 | Lauer |
| 6,764,460 B2 | 7/2004 | Dolecek et al. |
| 6,770,049 B2 | 8/2004 | Ludt et al. |
| 6,821,441 B2 | 11/2004 | Pedrini et al. |
| 6,830,553 B1 | 12/2004 | Burbank et al. |
| 6,843,779 B1 | 1/2005 | Andrysiak et al. |
| 6,852,090 B2 | 2/2005 | Burbank et al. |
| 6,918,886 B1 | 7/2005 | Baurmeister |
| 7,112,273 B2 | 9/2006 | Weigel et al. |
| 7,115,107 B2 | 10/2006 | Delnevo et al. |
| 7,300,413 B2 | 11/2007 | Burbank et al. |
| 2001/0021817 A1 | 9/2001 | Brugger et al. |
| 2001/0032818 A1 | 10/2001 | Nikaido et al. |
| 2001/0037079 A1 | 11/2001 | Burbank et al. |
| 2001/0045395 A1 | 11/2001 | Kitaevich et al. |
| 2002/0017489 A1 | 2/2002 | Utterberg |
| 2002/0041825 A1 | 4/2002 | Scheunert et al. |
| 2002/0072718 A1 | 6/2002 | Brugger et al. |
| 2002/0082728 A1 | 6/2002 | Mueller et al. |
| 2002/0103453 A1 | 8/2002 | Burbank et al. |
| 2002/0147423 A1 | 10/2002 | Burbank et al. |
| 2003/0010717 A1 | 1/2003 | Brugger et al. |
| 2003/0010718 A1 | 1/2003 | Burbank et al. |
| 2003/0018290 A1 | 1/2003 | Brugger et al. |
| 2003/0036719 A1 | 2/2003 | Giacomelli et al. |
| 2003/0047184 A1 | 3/2003 | Lockhart et al. |
| 2004/0019312 A1 | 1/2004 | Childers et al. |
| 2004/0019313 A1* | 1/2004 | Childers et al. ............ 604/5.01 |
| 2004/0019314 A1 | 1/2004 | Delnevo |
| 2004/0069709 A1 | 4/2004 | Brugger et al. |
| 2004/0138607 A1 | 7/2004 | Burbank et al. |
| 2004/0158189 A1 | 8/2004 | Tonelli et al. |
| 2004/0176724 A1 | 9/2004 | Kamen et al. |
| 2004/0186416 A1 | 9/2004 | Caleffi |
| 2004/0238416 A1 | 12/2004 | Burbank et al. |
| 2004/0243046 A1 | 12/2004 | Brugger et al. |
| 2004/0243047 A1 | 12/2004 | Brugger et al. |
| 2004/0243048 A1 | 12/2004 | Brugger et al. |
| 2004/0243049 A1 | 12/2004 | Brugger et al. |
| 2004/0243050 A1 | 12/2004 | Treu et al. |
| 2004/0245161 A1 | 12/2004 | Treu et al. |
| 2004/0249331 A1 | 12/2004 | Burbank et al. |
| 2004/0267184 A1 | 12/2004 | Burbank et al. |
| 2004/0267185 A1 | 12/2004 | Weaver et al. |
| 2005/0000868 A1 | 1/2005 | Weigel et al. |
| 2005/0004502 A1 | 1/2005 | O'Mahony et al. |
| 2005/0010158 A1 | 1/2005 | Brugger et al. |
| 2005/0011823 A1 | 1/2005 | Delnevo et al. |
| 2005/0020958 A1 | 1/2005 | Paolini et al. |
| 2005/0020959 A1 | 1/2005 | Brugger et al. |
| 2005/0020960 A1 | 1/2005 | Brugger et al. |
| 2005/0095141 A1 | 5/2005 | Lanigan et al. |
| 2005/0096583 A1 | 5/2005 | Demers et al. |
| 2005/0131332 A1 | 6/2005 | Kelly et al. |
| 2005/0230292 A1 | 10/2005 | Beden et al. |
| 2006/0084906 A1 | 4/2006 | Burbank et al. |
| 2007/0129707 A1 | 6/2007 | Blott et al. |
| 2008/0208103 A1 | 8/2008 | Demers et al. |
| 2009/0101549 A1 | 4/2009 | Kamen et al. |

FOREIGN PATENT DOCUMENTS

| | | |
|---|---|---|
| DE | 31 22 756 | 6/1982 |
| DE | 33 07 830 | 6/1984 |
| DE | 40 03 452 | 8/1991 |
| DE | 42 08 054 | 10/1992 |
| DE | 41 22 754 | 1/1993 |
| DE | 198 30 928 C1 | 5/1999 |
| DE | 198 14 695 A1 | 10/1999 |
| DE | 198 54 338 | 6/2000 |
| DE | 100 11 208 C1 | 9/2001 |

(56) References Cited

FOREIGN PATENT DOCUMENTS

| | | |
|---|---|---|
| DE | 101 00 146 A1 | 7/2002 |
| EP | 0 143 341 | 6/1985 |
| EP | 0165751 | 6/1985 |
| EP | 0165751 A2 | 12/1985 |
| EP | 0 166 920 A1 | 1/1986 |
| EP | 0 233 848 | 8/1987 |
| EP | 0 306 241 A2 | 3/1989 |
| EP | 0 373 455 | 6/1990 |
| EP | 0 222 709 | 5/1991 |
| EP | 0 490 212 | 6/1992 |
| EP | 0 623 357 A1 | 11/1994 |
| EP | 0 722 744 | 7/1996 |
| EP | 0 796 998 A1 | 9/1997 |
| EP | 0 659 091 | 12/2000 |
| EP | 1 097 724 | 5/2001 |
| EP | 1 235 613 | 8/2009 |
| FR | 78 31918 | 2/1979 |
| FR | 2 585 251 | 1/1987 |
| GB | 1 492 387 | 11/1977 |
| GB | 2 014 060 | 8/1979 |
| GB | 2 246 718 A | 2/1992 |
| JP | 61-008057 | 1/1986 |
| JP | 63-95063 | 4/1988 |
| JP | 07-035413 | 2/1995 |
| JP | 11 226121 | 8/1999 |
| JP | 2000-84071 | 3/2000 |
| JP | 217908 | 8/2000 |
| JP | 296318 | 10/2000 |
| JP | 2003518964 | 6/2003 |
| JP | 2004-205146 | 7/2004 |
| JP | 2004-209103 | 7/2004 |
| JP | 2006-500968 | 1/2006 |
| RU | 1001945 | 3/1983 |
| RU | 1821222 | 6/1993 |
| WO | WO 98/22165 | 5/1998 |
| WO | WO 98/32477 | 7/1998 |
| WO | WO 99/42150 | 8/1999 |
| WO | WO 00/09182 | 2/2000 |
| WO | WO 00/31967 | 6/2000 |
| WO | WO 00/57925 | 10/2000 |
| WO | WO 00/57926 | 10/2000 |
| WO | WO 00/57927 | 10/2000 |
| WO | WO 00/64510 | 11/2000 |
| WO | WO 01/37786 | 5/2001 |
| WO | WO 01/37894 | 5/2001 |
| WO | WO 01/37895 | 5/2001 |
| WO | WO 01/37900 | 5/2001 |
| WO | WO 01/41831 | 6/2001 |
| WO | WO 01/41832 | 6/2001 |
| WO | WO 01/42758 | 6/2001 |
| WO | WO 01/45769 | 6/2001 |
| WO | WO 0141833 | 6/2001 |
| WO | 01/47581 A1 | 7/2001 |
| WO | WO 01/47576 | 7/2001 |
| WO | WO 02/070042 | 9/2002 |
| WO | 03/011376 | 2/2003 |
| WO | 03/041764 | 5/2003 |
| WO | 2004/082731 | 9/2004 |
| WO | 2005/042065 | 5/2005 |
| WO | 2005/044339 | 5/2005 |
| WO | 2005/044339 A2 | 5/2005 |
| WO | 2005/044340 | 5/2005 |
| WO | WO 2005/044339 | 5/2005 |
| WO | WO 2006/105605 | 10/2006 |
| WO | WO 2007/074425 | 7/2007 |
| WO | WO 2008/033788 | 3/2008 |

OTHER PUBLICATIONS

European Search Report for European Application No. EP 11 18 5112 mailed on Dec. 20, 2011.
Japanese Office Action Mailed Dec. 20, 2012 for corresponding Japanese Appln. No. 2010-514907.
Japanese Office Action mailed Jan. 10, 2014 for related Japanese Appln. No. 2013-000322.
European Office Action dated Feb. 12, 2013 for related European Appln. No. 11075124.5.
European Search Report for Application No. EP 11 07 5130 mailed on Mar. 15, 2012.
European Office Action received Mar. 14, 2013 for related European Appln. No. 11075126.0.
European Search Report for European Application No. 11 07 5124 mailed on Mar. 16, 2012.
European Search Report for European Application No. 11 07 5125 mailed on Mar. 26, 2012.
European Search Report for European Application No. 11 07 5126 mailed on Mar. 22, 2012.
European Search Report for European Application No. 11 07 5127 mailed on Mar. 28, 2012.
European Search Report for European Application No. 11 07 5128 mailed on Apr. 3, 2012.
European Search Report for European Application No. 11 07 5129 mailed on Mar. 29, 2012.
Manns et al., The acu-menTM: A new device for continuous renal replacement therapy in acute renal failure, Kidney International, 1998, pp. 268-274, vol. 54.
European Office Action issued Apr. 18, 2013 for related European Appln. No. 11075127.8.
Mexican Office Action for Application No. PA/a/2006/005045 mailed Apr. 17, 2012.
European Office Action issued Jun. 6, 2013 for related European Appln. No. 11075125.2.
European Search Report issued Mar. 26, 2012, corresponding to European Appln. No. 11075125.2.
European Office Action issued Aug. 20, 2013 for related European Appln. No. 11075128.6.
U.S. Appl. No. 13/213,350, filed Aug. 19, 2011, Kelly et al.
U.S. Appl. No. 13/213,358, filed Aug. 19, 2011, Kelly et al.
U.S. Appl. No. 13/213,676, filed Aug. 19, 2011, Lo et al.
U.S. Appl. No. 13/213,812, filed Aug. 19, 2011, Lo et al.
U.S. Appl. No. 13/213,737, filed Aug. 19, 2011, Childers et al.
U.S. Appl. No. 13/213,727, filed Aug. 19, 2011, Childers et al.
U.S. Appl. No. 13/213,707, filed Aug. 19, 2011, Childers et al.
International Search Report and the Written Opinion for International Application No. PCT/US2008/064086 mailed on Jan. 27, 2009.
Japanese Office Action Received Sep. 18, 2012 for corresponding Japanese Appln. No. 2009-527618.
European Office Action received by foreign associate on Sep. 26, 2013 for related European Appln. No. 11075129.4.
European Office Action received by foreign associate on Sep. 30, 2013 for related European Appln. No. 11075130.2.
European Office Action received by foreign associate on Sep. 30, 2013 for related European Appln. No. 11185112.7.
European Office Action received by foreign associate on Sep. 26, 2013 for related European Appln. No. 11185090.5.
European Office Action mailed Aug. 7, 2014 for related European Appln. No. 11075128.6 (5 pages).
Japanese of Action mailed Jun. 30, 2014 for related Japanese Appln. No. 2013-169818 (10 pages).
Japanese Office Action issued Sep. 29, 2014 in corresponding Japanese Application No. 2011-163710.
Japanese Office Action mailed Jan. 30, 2014 in corresponding Japanese Patent Application No. 2011-163710.

* cited by examiner

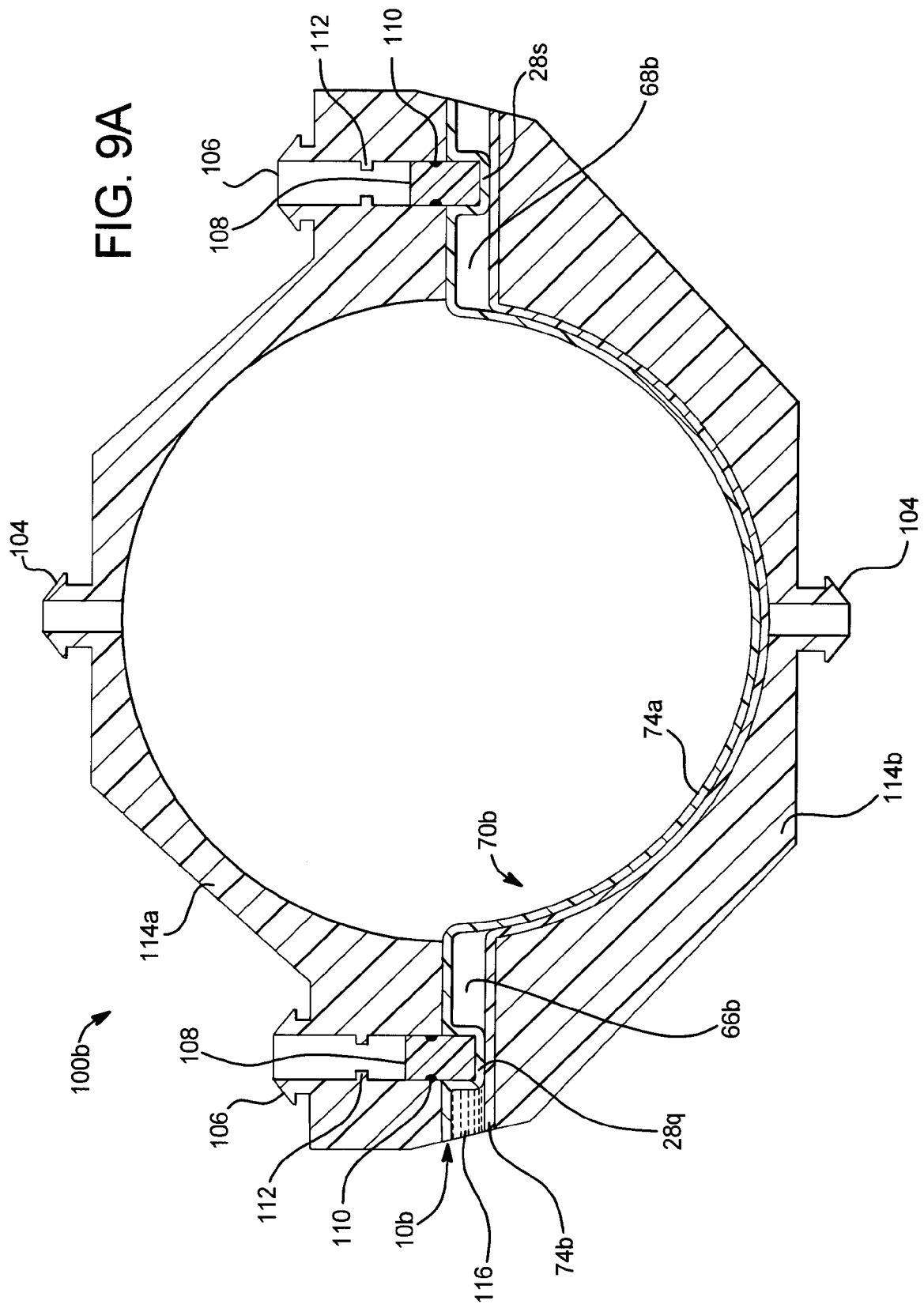

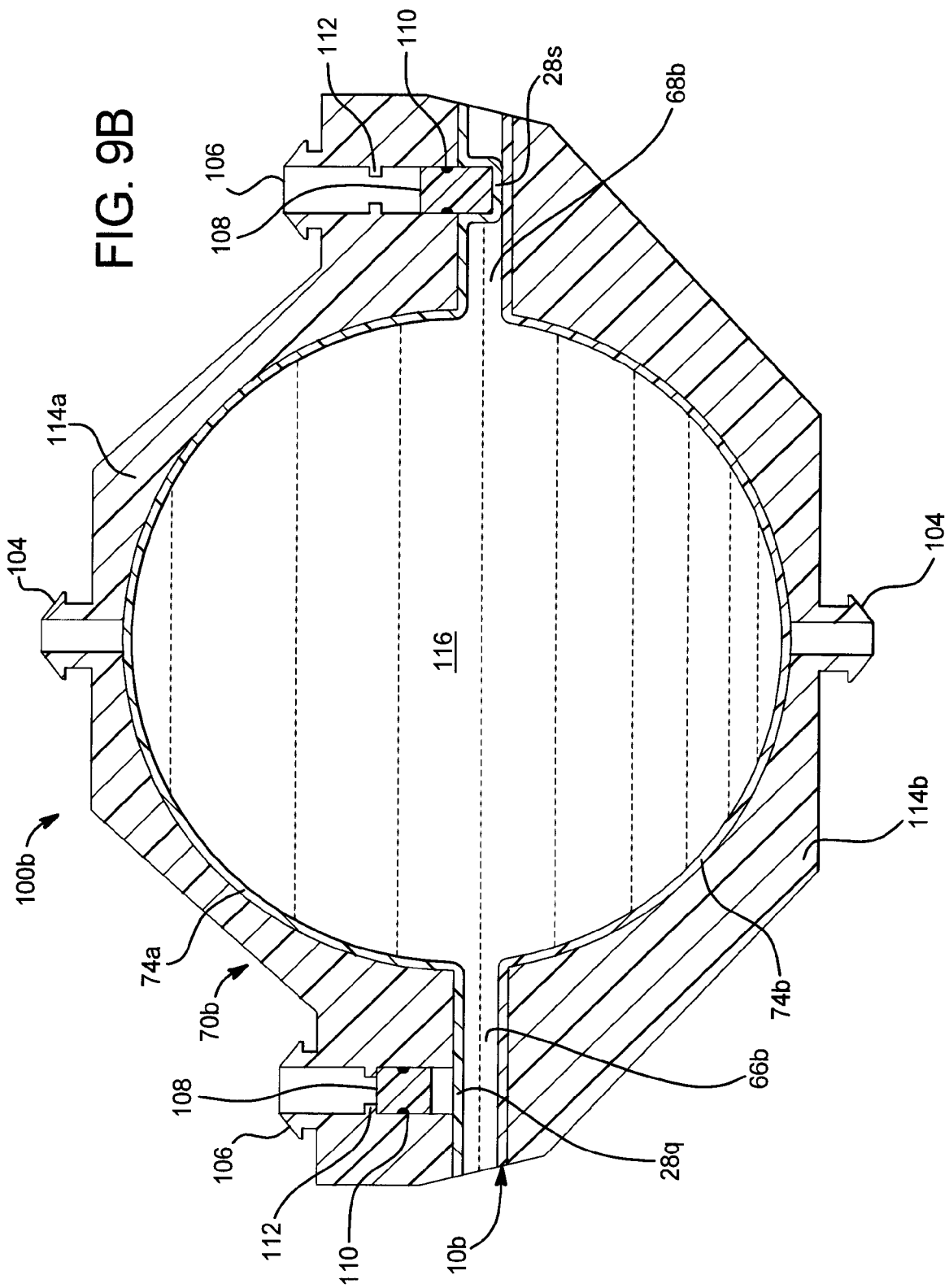

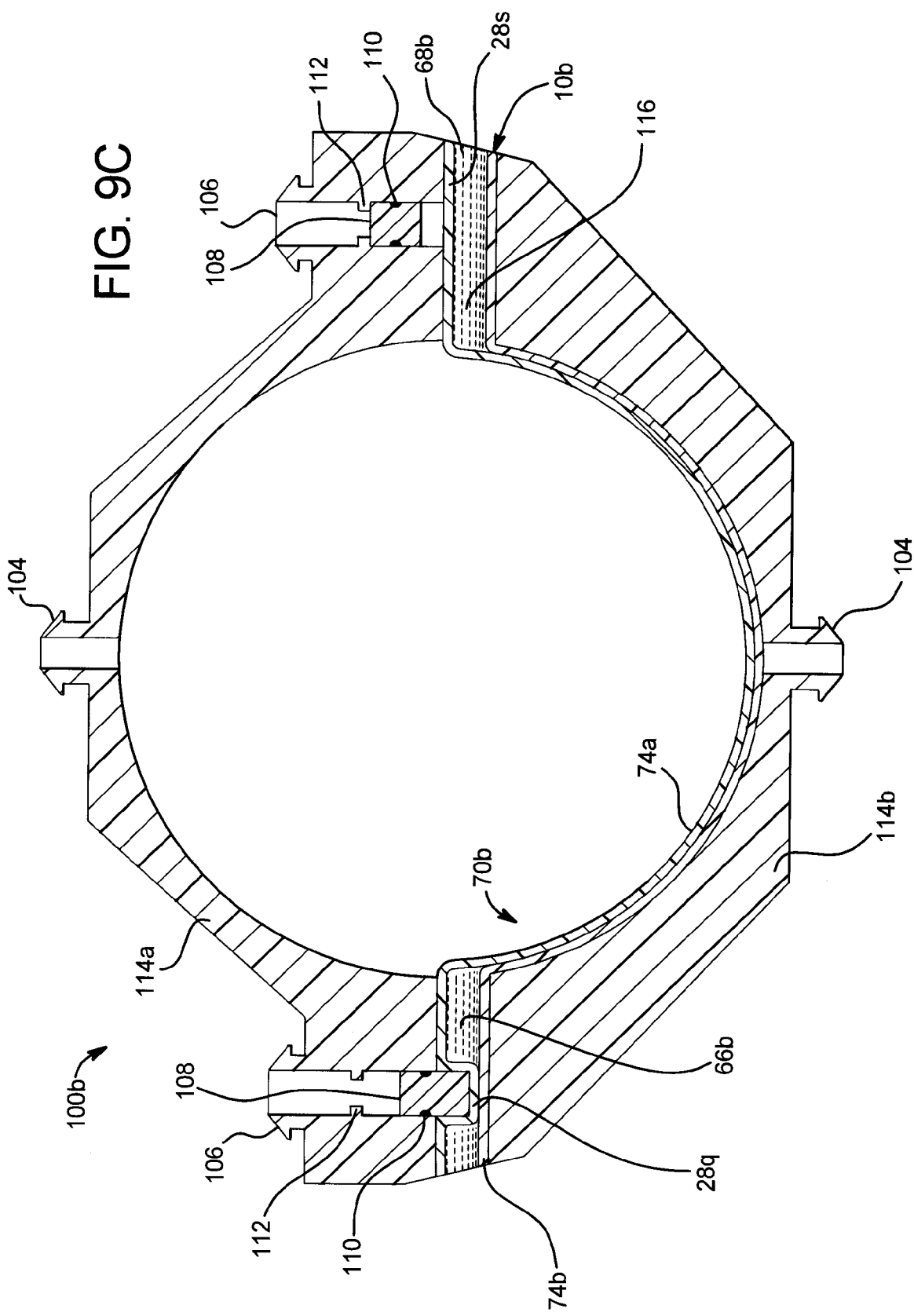

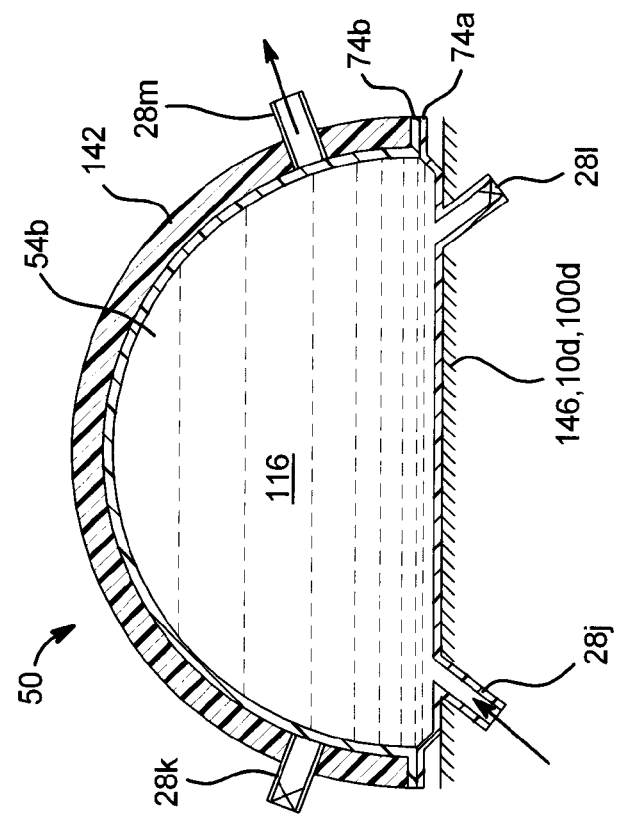
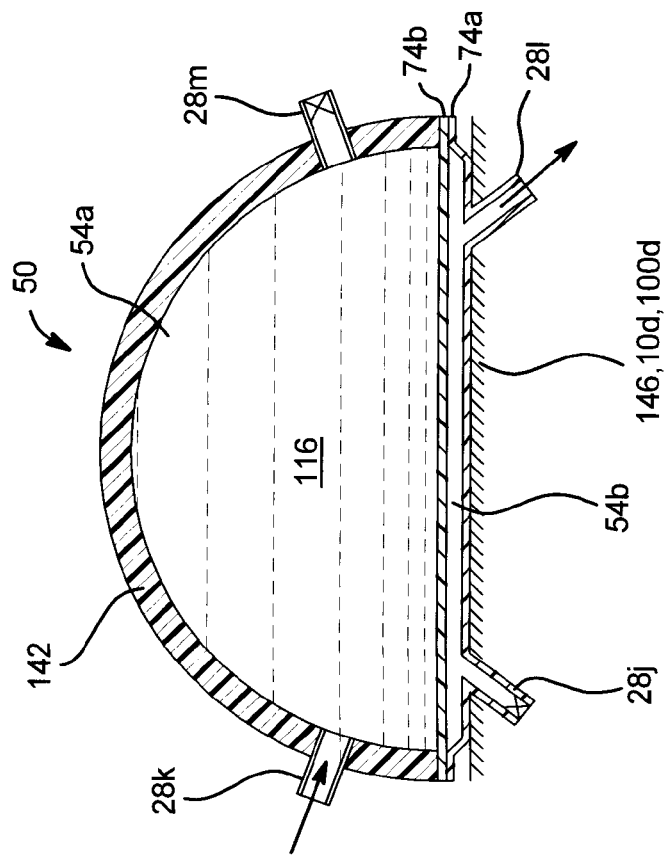
FIG. 19A
FIG. 19B

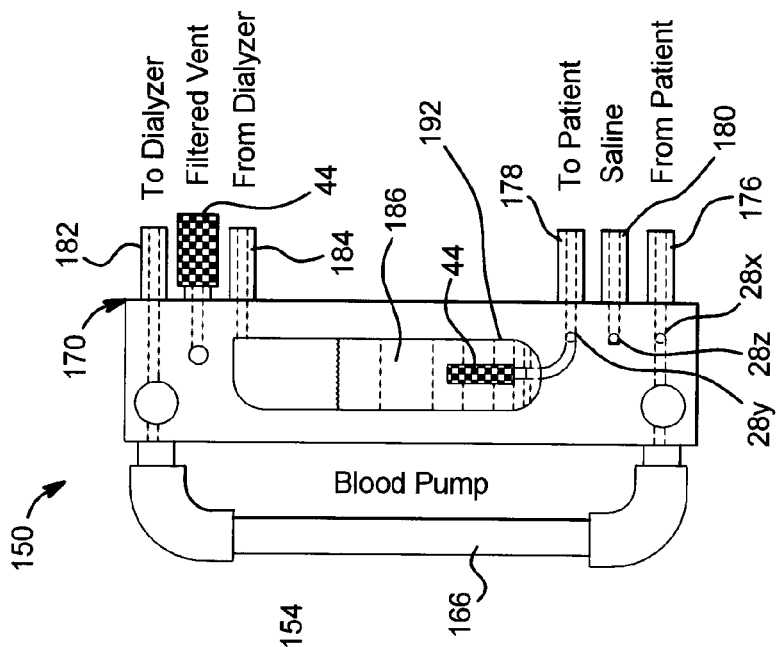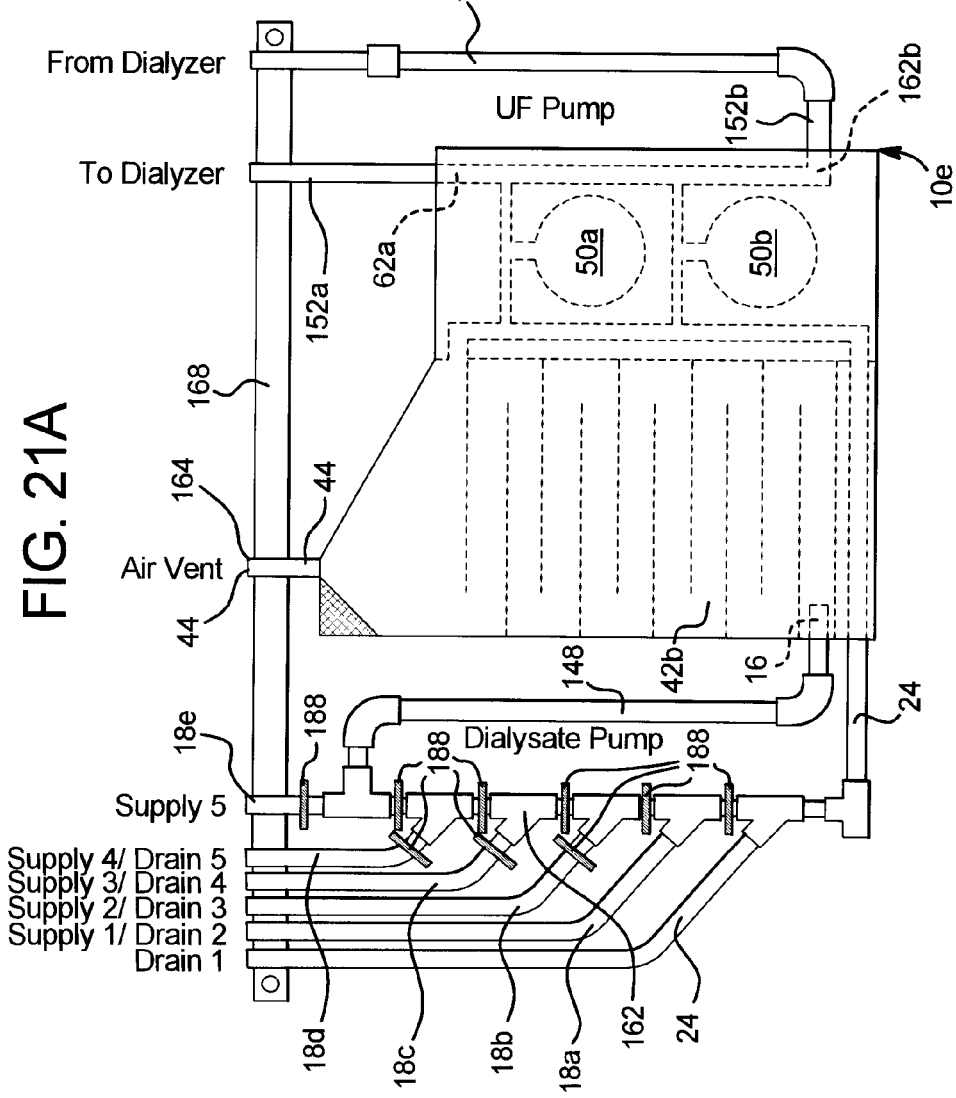

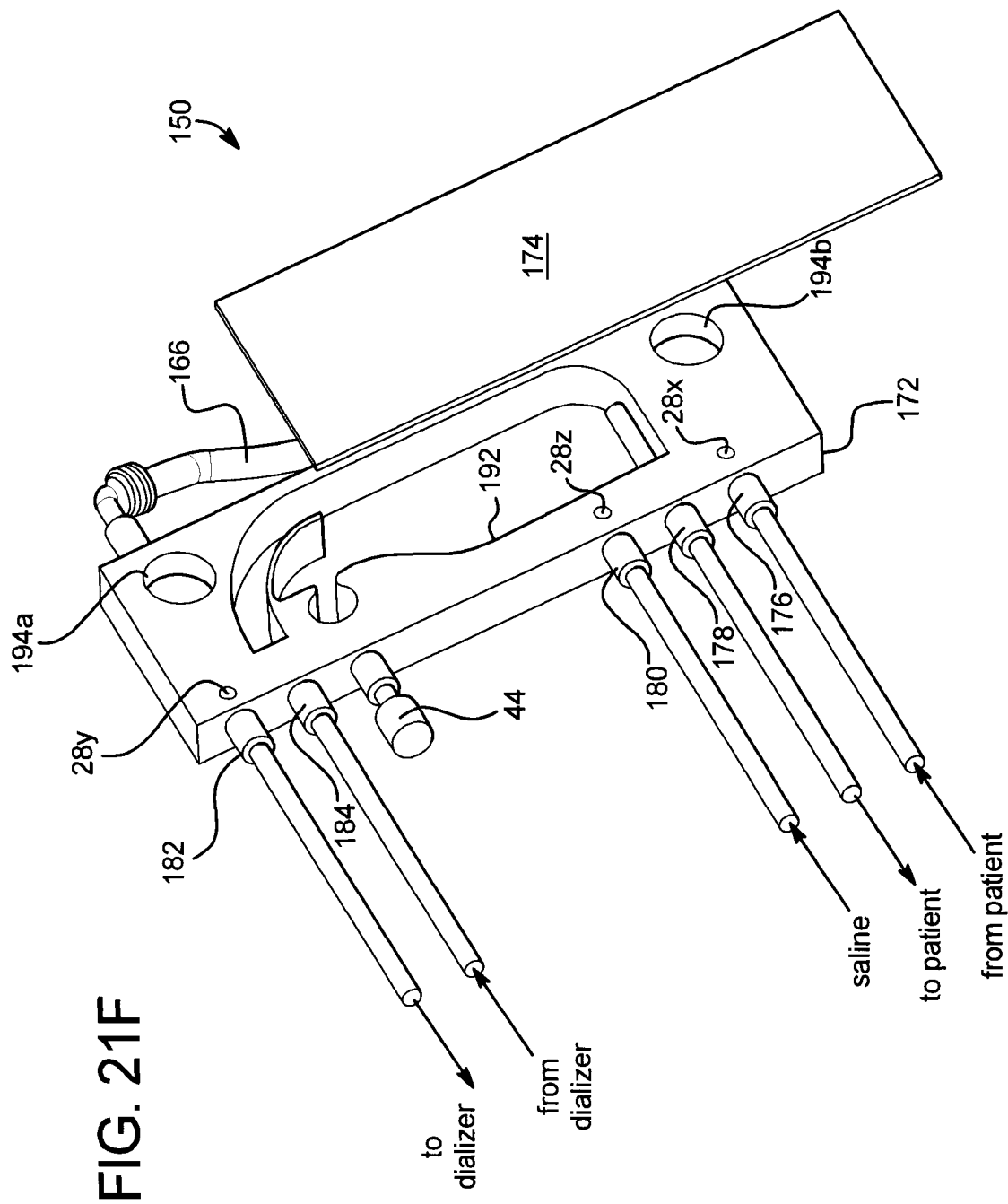

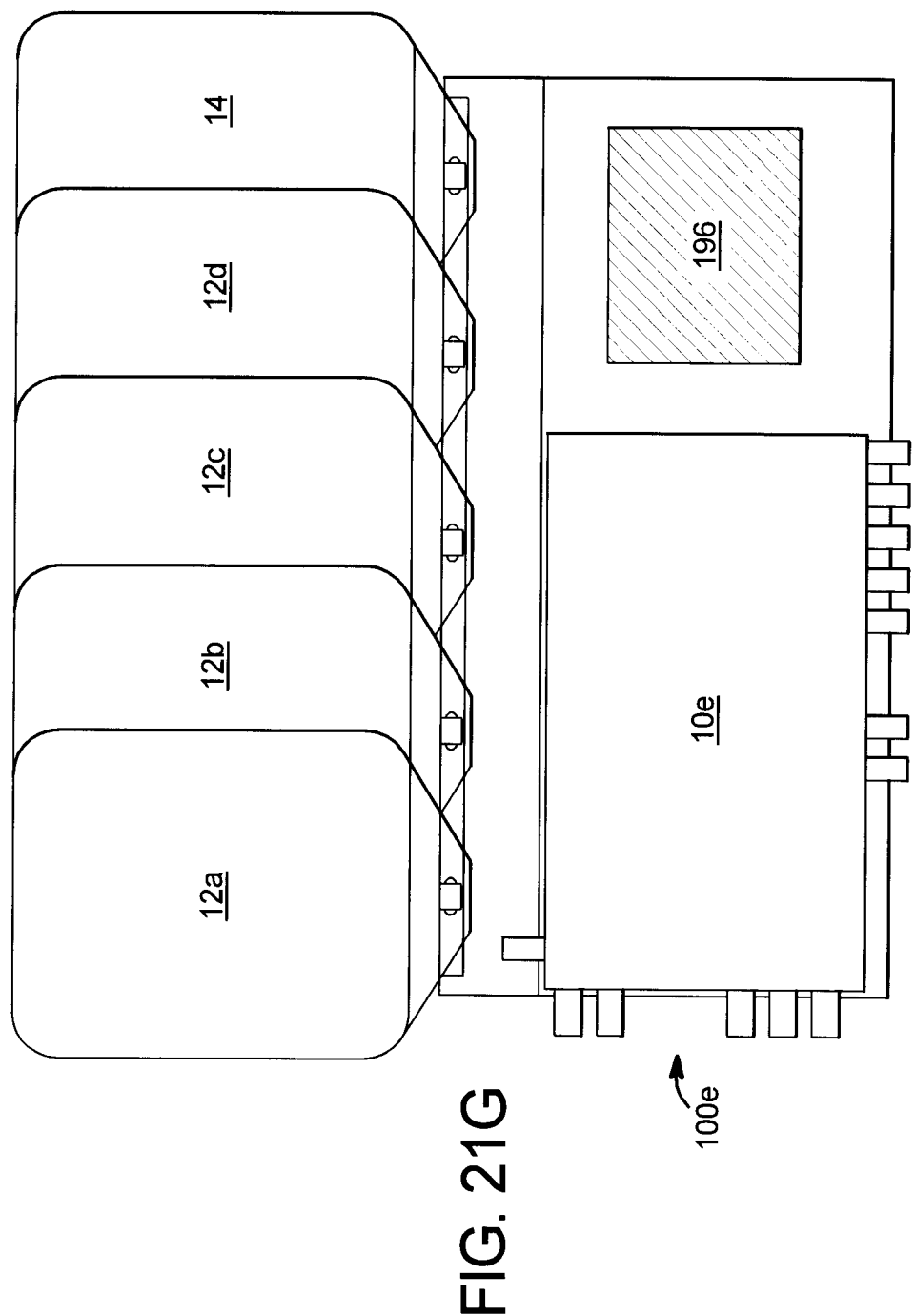

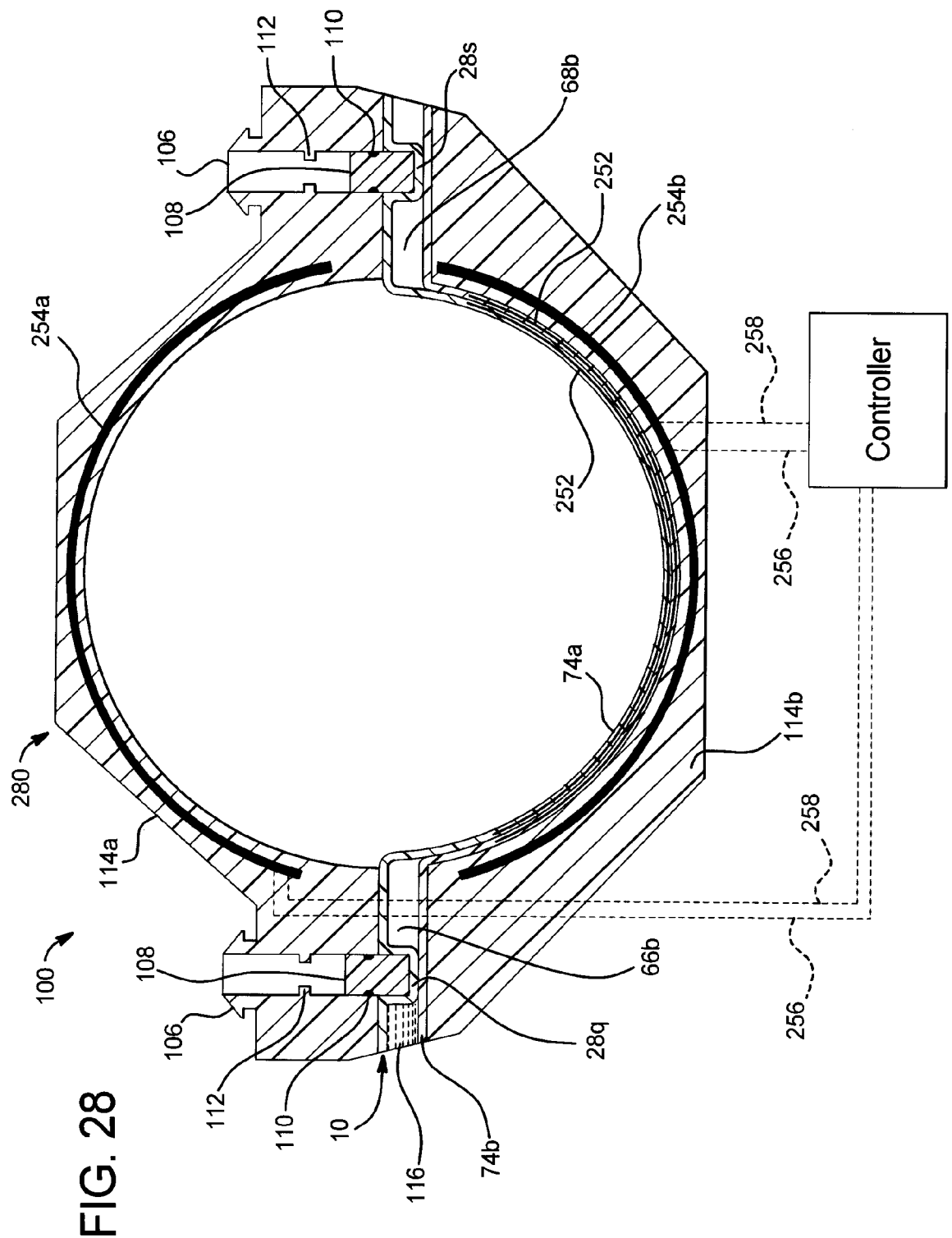

HEMODIALYSIS SYSTEM WITH CASSETTE-BASED BLOOD AND DIALYSTE PUMPING

PRIORITY CLAIM

This application claims priority to and the benefit as a continuation of U.S. patent application Ser. No. 11/530,842, entitled "Medical Fluid System With Flexible Sheeting Disposable Unit", filed Sep. 11, 2006, which is a continuation-in-part of U.S. patent application Ser. No. 10/982,170. entitled "High Convection Home Hemodialysis/Hemofiltration And Sorbent System", filed Nov. 4, 2004, which claims priority to and the benefit of U.S. Provisional Patent Application No. 60/517,730, filed Nov. 5, 2003, entitled "High Convection Home Hemodialysis/Hemofiltration And Sorbent System", the entire contents of each of which are hereby incorporated by reference and relied upon.

BACKGROUND

The examples discussed below relate generally to medical fluid delivery. More particularly, the examples disclose systems, methods and apparatuses for the control of fluid flow in kidney failure treatment systems.

Due to various causes, a person's renal system can fail. Renal failure produces several physiological derangements. The balance of water, minerals and the excretion of daily metabolic load is no longer possible and toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

Hemodialysis and peritoneal dialysis are two types of dialysis therapies used commonly to treat loss of kidney function. A hemodialysis ("HD") treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 120 liters, is consumed to dialyze the blood during a single hemodialysis therapy. Hemodialysis treatment lasts several hours and is generally performed in a treatment center about three or four times per week.

Another form of kidney failure treatment involving blood is hemofiltration ("HF"), which is an alternative kidney failure therapy that relies on a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules waste products.

Hemodiafiltration ("HDF") is another blood treatment modality that combines convective and diffusive clearances. HDF uses dialysate to flow through a dialyzer, similar to standard hemodialysis, providing diffusive clearance. In addition, substitution solution is provided directly to the extracorporeal circuit, providing convective clearance.

Peritoneal dialysis uses a dialysis solution, also called dialysate, which is infused into a patient's peritoneal cavity via a catheter. The dialysate contacts the peritoneal membrane of the peritoneal cavity. Waste, toxins and excess water pass from the patient's bloodstream, through the peritoneal membrane, and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow APD and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from the dialysate source, through the catheter, into the patient's peritoneal cavity, and allow the dialysate to dwell within the cavity, causing the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during APD. A "last fill" occurs at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. The systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

In each of the kidney failure treatment systems discussed above, it is important to control ultrafiltration, which is the process by which water (with electrolytes) moves across a membrane, such as a dialyzer or peritoneal membrane. For example, ultrafiltration in HD is a result of transmembrane and osmotic pressure differences between blood and dialysate across a dialyzer membrane. For a given osmotic pressure, the greater the transmembrane pressure the more rapid the ultrafiltration.

Many of the above-described dialysis systems employ a pumping cassette. The pumping cassette typically includes a flexible membrane that is moved mechanically to push and pull dialysis fluid out of and into, respectively, the cassette. Certain known systems include flexible sheeting on one side of the cassette, while others include sheeting on both sides of the cassette. Positive and/or negative pressure can be used to operate the pumping cassettes.

The pumping cassettes have many design concerns. For example, one problem with the pumping cassettes is leakage. If the flexible membranes experience a pinhole or tear, fluid and air can move from one side of the membrane to the other. Movement of fluid from inside the cassette to the inner workings of the machine can damage the machine. Movement of air from the machine into the cassette can compromise the sterility of the fluid pathways defined by the cassette.

Another problem with cassette-based pumping occurs when the cassette is loaded improperly into the machine. Proper alignment is important because portions of the flexible membrane must match corresponding machine portions, e.g., pump and valve actuators. Improper loading can lead to undue mechanical stress being placed on the cassette, harming potentially the cassette and/or the actuator. Improper cassette loading can also degrade or prohibit performance of the system.

A further dilemma, especially in CFPD, is the coordination of multiple fluid deliveries. Cassette-based peritoneal pumping systems that administer fluids continuously to patients are required to withdraw fluid (ultrafiltrate) from and add fluid (concentrate) to a continuously flowing dialysis fluid loop. The additional fluids have typically necessitated additional dedicated pumps, which make the cassette and dialysis machine larger and noisier. Scheduling the operation of multiple pumps also presents a challenge to system implementers.

Yet another problem associated with cassette-based pumping is the entrapment of air or other gas in the fluid pathways. Air can enter the system via leaking connections, improper priming, faulty tubing and faulty cassettes. Patient therapy also produces various gases that enter the system. Cassette-based pumps are designed to pump fluid, not gas. Moreover, the removal and delivery of fluid from and to the patient needs to be monitored and controlled. For PD-type systems, air and gases upset volume measurement systems that assume no air or gas exists in the fluid pathways. Air and gases can also be uncomfortable for the patient and impede proper waste removal. For HD-type systems, air in the blood stream can be harmful to the patient.

Cost, ease of manufacturing, durability and reliability are additional concerns facing cassette-based dialysis systems. A need therefore exists for improved cassettes for cassette-based dialysis systems, which satisfy the above-described concerns.

SUMMARY

The examples described herein disclose dialysis systems employing a flexible pumping cassette such as: hemodialysis ("HD"), hemofiltration ("HF"), hemodiafiltration ("HDF"), peritoneal dialysis (("PD"), including continuous ambulatory peritoneal dialysis ("CAPD"), automated peritoneal dialysis ("APD"), tidal flow APD and continuous flow peritoneal dialysis ("CFPD") modalities). The systems may also be used in any type of continuous renal replacement therapy ("CRRT"). The examples below include a diffusion membrane or filter, such as a dialyzer, e.g., for HD or HDF, a hemofilter, e.g., for HF or the patient's peritoneum, e.g., for PD. Moreover, each of the systems described herein may be used in clinical or home settings. For example, the systems may be employed in an in-center HD machine, which runs virtually continuously throughout the day. Alternatively, the systems may be used in a home PD machine, which is typically run at night while the patient is sleeping. One particularly suitable therapy for the embodiments described herein is home hemodialysis ("HHD") and in particular high convection home hemodialysis ("HCHD").

The examples below include a dialysate (replacement fluid) supply, which can be multiple bags of dialysate supply that are ganged together and used one after another. Further alternatively, each of the systems shown below can be used with an online dialysate source, such as one or more concentrate pump configured to combine one or more concentrate with water to form dialysate online. Online sources are used commonly with in-center HD systems for example. While the systems are described herein for use with dialysate, it is expressly contemplated to use the flexible sheeting cassettes and other apparatus with other medical fluids, such as saline, lactated ringers, drugs and/or blood.

Various flexible sheeting cassettes are shown and described herein. The flexible sheeting cassettes use a multitude of flexible sheets that are welded, heat sealed, adhered, chemically bonded, folded or otherwise formed together at desired places to produce fluid flow paths, fluid heating pathways, peristaltic pump paths, volumetric pumping areas, balance chambers (matched flow equalizers) and any combination thereof. The different sheets can be formed as separate sheets before attaching them together or be a single sheet that is folded one or more time to produce the different layers. The sheets provide an economical and readily producible alternative to known medical fluid pumping cassettes, which typically include a hard plastic component and one or more flexible sheet sealed to the hard plastic component.

It is expressly contemplated however to provide a cassette in which some components use a hard plastic member and others use flexible sheets only. For example, it may be advantageous to form the valves and certain pathways using a hard plastic piece in combination with one or more flexible sheet and form the pumping portion(s), balance chamber(s) and/or heating fluid pathway using flexible sheets only. Certain embodiments shown below combine flexible sheet cassettes with tubing loops, for example, tubing loops used in combination with a peristaltic pump roller. It is also expressly contemplated to provide a cassette in which the flow paths, heating pathway, pumping portion and volume control portion are each formed using flexible sheeting, but which includes a rigid frame for ease of handling, loading, etc.

In one embodiment a cassette is shown using two or three sheeting layers as needed to provide fluid pathways, a peristaltic pumping portion, a balance chamber portion, which are sealed together and formed with connectors that connect to one or more supply bag, a drain bag and a patient (as used herein, "patient" generally refers to a patient's peritoneum, a dialyzer, a hemofilter, a extracorporeal circuit and any combination thereof). In one implementation, a separate fluid heating pathway is provided and connected fluidly to the flexible sheeting cassette via separate tubes.

In another embodiment, the fluid heating pathway is formed using the same sheets that form other components of the dialysate fluid system, such as volumetric pump portions. The volumetric or membrane pumping portions pump a known volume of fluid with each stroke and therefore preclude the need for separate match flow equalizers or balance chambers.

Any of the flexible sheeting cassettes described herein can have one or more pumping portion. For example, the flexible sheeting cassettes can form multiple peristaltic pumping portions in combination with multiple balance chambers, which operate to produce an at least substantially steady flow of fresh and spent dialysate to the "patient" and drain, respectively. In another example, the flexible sheeting cassettes can form multiple volumetric or membrane pumping portions.

The flexible sheeting membranes also incorporate a vent, which can be located advantageously just down stream of an integrated or separate fluid heating pathway. This configuration enables air or gas generated via the heating to be vented or released to atmosphere. The vent for example can be located at the top of a vertically disposed or positioned cassette to allow for automatic air purging. Or, the cassette can be mounted horizontally in the machine and operate with a valve, which opens when air is detected. The System could vent/release gas/air to other parts of the disposable (such as a solution bag or drain line), not just to the atmosphere.

In an embodiment the flexible sheeting cassettes include connectors that connect the tubes that lead to fluid bags, the patient, a dialyzer, extracorporeal circuit, etc. In an embodiment the connectors include a body, which can be rigid, and which is sealed between two of the flexible sheets. One or both of the flexible sheets can have a thermoformed flow path, which is sealed to the other flexible sheet to form a closed flow path that leads from the connector body to a desired destination within the flexible sheeting cassette. An external end of the connector body can include a luered or ferruled end, which is configured to be sealed tightly to a tube running from the flexible sheeting cassette.

In an embodiment one of the flexible sheets includes a substantially circular thermoformed pathway leading to inlet and outlet pump pathways. A peristaltic pump roller or actuator operates with the substantially circular fluid pathway to form an integral peristaltic pumping portion of the flexible sheeting cassette. As discussed above, one or more such pumping portions may be provided in any single cassette. In such a case, described below are two embodiments for using a single roller to drive two different peristaltic pumping pathways. In one example, the flexible sheeting cassette is folded over a member, causing two inwardly facing peristaltic pumping portions to be coupled operably to a single peristaltic pump roller. In a second example, the peristaltic pumping pathway is a semicircle as opposed to a substantially complete circle, wherein two of the semicircular flow paths operate with the same peristaltic pump roller, to drive two different fluids through two different pathways.

Multiple embodiments for producing match flow equalizers or balance chambers using multiple flexible sheets are also disclosed herein. In one implementation, three sheets are used to create upper and lower balance chamber compartments, namely, one between an upper sheet and a middle sheet and the other compartment between the middle sheet and a lower sheet. Each compartment can have single or multiple fluid pathways leading to and from such compartment. Pumping fluid into a compartment dispenses a like amount of fluid from the other compartment and vise versa. In an embodiment, each compartment includes two pathways connected thereto, wherein one pathway is an inlet pathway to the compartment and the other pathway is an outlet pathway from the compartment. In another implementation, only a single pathway communicates with each of the compartments, causing fluid entering and exiting each compartment to flow through the same single pathway.

In an alternative embodiment, two flexible sheets are formed with a rigid, e.g., spherical plastic chamber to form a balance chamber. Here, one compartment is formed between the rigid chamber and an upper flexible sheet. The second compartment is formed between the two flexible sheets. A rigid plate or backing is abutted against the lower flexible sheet, causing the upper flexible sheet to have only one direction in which to move when the lower compartment is filled. When the lower compartment is filled the upper flexible sheet is moved upwards towards an inner wall of the rigid chamber to dispense fluid from the upper compartment. Next fluid is filled into the upper compartment, pushing the upper sheet down towards the lower sheet to dispense fluid from the lower compartment.

In yet another alternative balance chamber embodiment, a plurality of flexible sheets is formed with a plurality of balance chamber tubes to form the balance chamber. The tubes act as fluid inlets and fluid outlets, which alternatively are formed via thermo-forming one or both of the flexible sheets. Again, each balance chamber compartment can include a single inlet/out tube or multiple dedicated inlet/outlet tubes to produce a single fluid inlet/outlet or separate fluid inlet/outlet.

The balance chambers are generally described herein operating with pumps, such as peristaltic pumps. In an alternative embodiment described below, the balance chamber is placed inside a magnetic field. Hence, the membrane (e.g., inner membrane) of the balance chamber that is driven back and forth within the chamber is doped or otherwise coupled with a ferromagnetic material. For example, a thin carbon layer can be sandwiched between outer flexible layers of air insert medical grade material. The magnetic field is modulated or polarized to move the impregnated membrane. A controller within the dialysis unit powers electromagnets located at either side of the balance chamber sequentially to draw the magnetic inner membrane to one side of the chamber and then the other, dispelling and drawing in fluid with each half-stroke. In this manner, the balance chamber (or dual balance chambers) is itself driven as opposed to being driven by a separate pump, eliminating the need for the second pump. As described below, the balance chamber systems sometimes use an ultrafiltration ("UF") meter, which is also typically passive or non-self driving. The UF meter can also be driven magnetically as described herein. Alternately, one of the magnetically driven balance chambers drives the UF meter. As further discussed below, volumetric pumps may also be modified to be driven magnetically.

As shown below an integrated volumetric or membrane pump can be formed using two flexible sheets and upper and lower chambers defined by the machine in which the cassette is loaded. The machine is configured to pull a vacuum on each of the separate sheets to pull the sheets toward the chamber wall and to provide positive pressure to push the sheet towards the opposing chamber wall as needed to draw in or push out fluid. A fluid-in pathway and fluid-out pathway communicate fluidly with the space between the flexible sheets.

The inlet and outlet pathways are valved to enable fluid to be pulled into the volumetric pump chamber in one step and to be pushed out the volumetric pump chamber in a second step. As shown below, to pull fluid into volumetric pump chamber, positive pressure is removed and negative pressure is applied to the outer surface of one the flexible sheets to pull it from the other flexible sheet (which is under negative pressure from the other side of the chamber) towards its vacuum source, causing the pumping chamber between the sheets to open, create a vacuum and thereby pull fluid into the chamber. Next, positive pressure is applied to one of the sheets, pushing the flexible membranes closed and fluid out the pump outlet pathway.

Multiple embodiments are discussed herein for forming an integrated fluid heating pathway. The pathway can be a thermoformed pathway in one sheet that is bonded to a second sheet. In another embodiment, three sheets are used, wherein upper and lower pathways are formed with a flat middle sheet. In any of the embodiments described herein, the middle sheet includes one or more aperture to enable fluid, for example, to travel from an upper fluid heating pathway to a lower fluid heating pathway. Or with respect to the balance chambers, an aperture in the middle flexible membrane enables fluid exiting one (upper or lower) compartment to be combined with fluid exiting the other compartment in a single flow path.

Various embodiments are described herein for selectively forming the seals between two of three abutting sheets and for sealing three sheets to together. For example, a pattern of curable adhesive can be provided on one or more sides of the middle sheet to enable one or more outer sheets to be selectively adhered and sealed thereto. Alternatively, the energy provided by a heating die can be varied such that the heat generated by the die is set to seal only two of three sheets together or to seal all three sheets together.

As discussed above, any of the flexible sheeting cassettes can include a rigid component, which for example can include flow pathways, valve seats, rigid balance chamber portions, etc. As shown below, that rigid portion can be made to communicate with an all-flexible portion, which forms the remaining components of the cassette.

As discussed above, the peristaltic pumping portions can alternatively be tubes that are connected fluidly to a flexible sheeting cassette, which can include a heater flow path, balance chamber portion(s) and associated flow paths and valve seats.

In one embodiment one flexible sheeting cassette is provided for the dialysate portion of an HD, HF or HDF system, wherein a second blood cassette is provided. Both cassettes are loaded into the same machine in one embodiment. Alternatively, blood and dialysate portions of an HD, HF or HDF system can be formed in the same cassette.

It is therefore an advantage of the present disclosure to provide improved dialysis systems.

It is another advantage of the present disclosure to provide improved dialysis cassettes.

It is a further advantage of the present disclosure to provide improved home dialysis therapies.

It is still another advantage of the present disclosure to incorporate peristaltic pumping portions into a cassette formed from multiple flexible sheets.

It is still a further advantage of the present disclosure to incorporate membrane or volumetric pumping portions into a cassette formed from multiple flexible sheets.

It is a further advantage of the present disclosure to provide multiple ways to form fluid pathways in two or three abutting flexible membranes.

It is yet another advantage of the present disclosure to incorporate balance chamber portions into a cassette formed from multiple flexible sheets.

It is yet a further advantage of the present disclosure to provide a relatively low cost flexible sheeting cassette.

Moreover, it is an advantage of the present disclosure to provide methods for selectively sealing two of three abutting sheets or three of three abutting sheets together, for example.

Still additionally, it is an advantage of the present disclosure to provide a magnetically driven volumetric balancing or pumping device.

Additional features and advantages of the present disclosure will be apparent from, the following Detailed Description of the Invention and the figures.

BRIEF DESCRIPTION OF THE FIGURES

FIGS. 9A to 9C are sectioned elevation views of Detail IX shown in FIG. 2, illustrating different valve states of a pump cycle for a volumetric pumping operating using the flexible sheeting cassettes.

FIGS. 19A and 19B are sectioned elevation views showing another embodiment for a balancing chamber portion using two flexible sheets in combination with a rigid plastic domed component.

FIGS. 21A to 21G are various views of one system employing a flexible sheeting dialysate cassette in combination with a separate blood-side cassette.

FIG. 28 illustrates a volumetric pump driven by a magnetic field.

DETAILED DESCRIPTION

Figure 1:
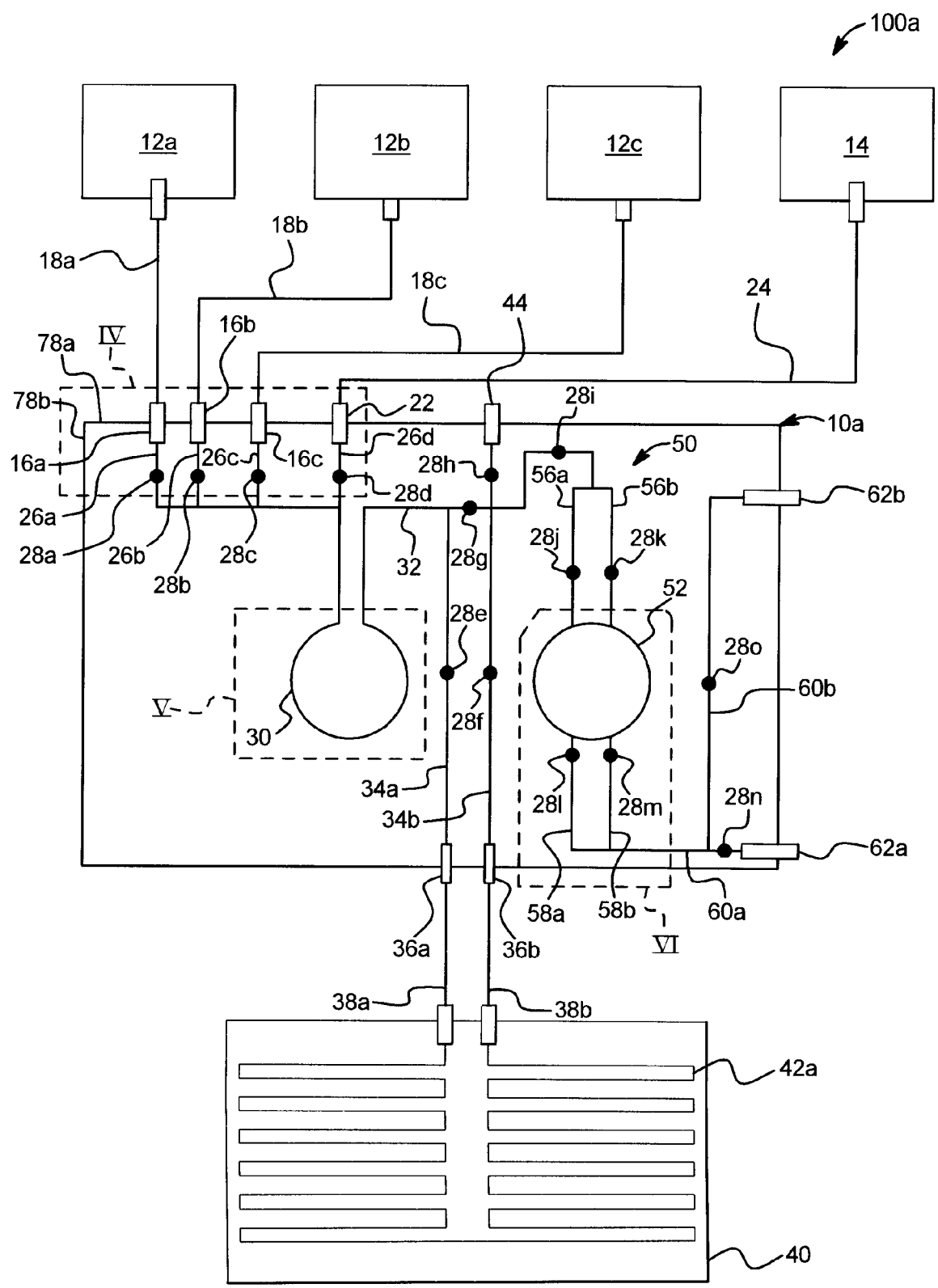
FIG. 1 is a schematic view of one embodiment of a cassette-based dialysis system employing a flexible sheeting cassette having a peristaltic pumping portion, a single balancing chamber volumetric control portion and an external heater bag.

The examples described herein are applicable to any medical fluid (such as dialysate, substitution fluid and blood) therapy system requiring a disposable fluid pumping cassette. The systems are particularly well suited for the control of kidney failure therapies, such as all forms of hemodialysis ("HD") including ("HHD"), hemofiltration ("HF"), hemodiafiltration ("HDF"), peritoneal dialysis ("PD," including continuous ambulatory peritoneal dialysis ("CAPD"), automated peritoneal dialysis ("APD"), tidal flow APD and continuous flow peritoneal dialysis ("CFPD") modalities). The systems may also be used in any type of continuous renal replacement therapy ("CRRT").

The examples below include a diffusion membrane or filter, such as a dialyzer, e.g., for HD or HDF, a hemofilter, e.g., for HF or a peritoneum, e.g., for PD. Certain examples show a cassette with a single patient inlet and outlet, e.g., for batch type CAPD or APD. Dialysate in CAPD and APD is typically delivered to the patient, allowed to dwell for a period, and then pumped from the patient and discarded to drain. Those cycles are then repeated a number of times. The to- and from-patient lines are teed together and valved appropriately, for example, so that dialysate can be delivered and removed at different times via the same single line and connection to and from the patient.

Other systems include a dialysate inlet and a dialysate outlet, e.g., for a dialyzer or hemofilter used with HD, HDF or HF. The systems may each also be modified for use with a single or dual catheter as the case may be. CFPD typically uses a dual lumen catheter and thus requires separate inlets and outlets as well.

Moreover, each of the cassette-based systems described herein may be used in clinical or home settings. For example, the systems may be employed in an in-center HD machine, which runs virtually continuously throughout the day. Alternatively, the systems may be used in a home PD machine, which is typically run at night while the patient is sleeping. Home hemodialysis ("HHD") (including high convection home hemodialysis ("HCHD")) machines are also one preferred type of therapy machine for use with the embodiments described herein.

The examples below include a dialysate (or replacement fluid) supply, which for convenience is shown as multiple bags of the fluid. Alternatively, a single bag of dialysate supply is used. Further alternatively, each of the systems shown below can be used with an online dialysate or replacement fluid source, such as one or more concentrate pump configured to combine one or more concentrate with water to form dialysate online. For example, online sources are used commonly with HD systems.

Each of the systems shown herein operates with a heater that heats the dialysate or replacement fluid to a desired temperature. The heaters can be inline heaters located upstream or downstream of the fresh supply pump. The systems may alternatively operate with a batch type heater and/or a heater located upstream of the pump.

The systems also include a cassette with an inline air removal device (e.g., hydrophobic vent). Alternatively, a batch-type air removal device, such as an air trap is used. The air removal device can be located at or near the heating pathway to capture air that has egressed from the solution due to heating.

The flow schematics shown herein mainly involve the dialysate or replacement fluid portion of the kidney failure machine. HD, HF and HDF machines also include blood pumping systems. Various examples of blood cassettes are also discussed below.

HD, HF and HDF also include dialysate proportioning systems, mentioned above, which are also known and need not be described here. U.S. Pat. No. 5,247,434 ("the '434 Patent"), assigned to the assignee of the present application, the entire contents of which are incorporated expressly herein by reference, describes one example of a suitable proportioning system.

Referring now to the drawings and in particular to FIG. 1, one embodiment of a system employing a flexible sheeting cassette 10a is illustrated by system 10. System 100a is advantageous in one respect because it employs a peristaltic pump 30 in combination with a volumetric balancing device or balance chamber. Peristaltic pumps, such as pump 30, are typically used to pump clean or sterile fluids, such as dialysate or replacement fluid, because the pump hardware does not contact and thus contaminate the fluid. The only part of the pump in contact with the dialysate/replacement fluid is the peristaltic pumping path or tube segments, which are sterilized before therapy. Also, because peristaltic pumps include no moving parts in contact with the dialysate/replacement fluid, the pumps are relatively inexpensive. Peristaltic pumps also lack the valves, seals and glands used in other types of pumps, which makes pump 30 for example, comparatively inexpensive and easy to maintain.

The volumetric balancing of system 100a uses first and second chambers of substantially equal volume in one embodiment. Each chamber includes two compartments, one termed a "pre-dialyzer" compartment and the other a "post-dialyzer" compartment. Each opposing "pre" and "post" compartment of a chamber is separated by a flexible diaphragm. Solenoid-actuated valves control the filling and emptying of each compartment. In general, each compartment is completely filled before its contents are discharged. Also, the "pre" compartments are alternately filled and discharged and the "post" compartments are alternately filled and discharged. Filling a "pre" compartment causes a discharge of a corresponding and opposing "post" compartment, respectively. Filling a "post" compartment causes a discharge of a corresponding and opposing "post" compartment.

Since the volumes of opposing "pre" and "post" compartments of the two chambers are equal, the system volumetrically balances the flow of dialysate to and from the dialyzer. One benefit of this volumetrically controlled system is that dialysate flow to the dialyzer can be accurately measured over a wide range of flowrates.

System 100a includes a plurality of supply bags 12a to 12c. The dialysate supply to system 100a is alternatively any of the systems described above, such as an online supply. System 100a also includes an initial drain bag 14 in the illustrated embodiment. With PD for example the patient's peritoneum is full of spent dialysate at the beginning of therapy. That spent dialysate is from a last-fill from the previous night's therapy. The first step in the treatment in PD is therefore to drain the spent dialysate to drain bag 14. Thereafter, supply dialysate is pumped from supply bags 12a to 12c through cassette 10a to the patient (as used herein, "patient" refers to a dialyzer, an extracorporeal circuit, a patient's peritoneum or a combination thereof depending on the therapy involved). Those supply bags then double as drain bags over the different cycles of treatment, e.g., after the dialysate has dwelled inside the patient's peritoneum for a designated amount of time and is thereafter pumped back through the cassette to the drain bag. For example, dialysate could be pumped initially from supply bag 12a, through cassette 10a, to the patient. After a preset dwell period, the spent dialysate is then pumped from the patient, through cassette 10a to bag 12a, which is now a drain bag. Afterwards, system 100a in a next cycle pumps fresh dialysate from supply bag 12b to the patient, and so on.

Supply bags 12a to 12c are connected fluidly to supply connectors 16a to 16c via supply tubes 18a to 18c, respectively. Supply connectors 16a to 16c are connected sealingly to flexible sheeting cassette 10a as illustrated in more detail below in connection with FIG. 4. Drain bag 14 is connected fluidly to drain connector 22 via drainline 24. Drain connector 22 is connected sealingly to flexible sheeting cassette 10a in the same manner that supply connectors 16a to 16c are connected sealingly to flexible sheeting cassette 10a as shown in more detail below in connection with FIG. 4.

Flexible sheeting cassette 10a defines or includes flow paths 26a to 26d that enable fluid flowing through lines or tubes 18a to 18c and 24 to communicate fluidly with a peristaltic pumping portion 30, which flexible sheeting cassette 10a also defines or includes. Peristaltic pumping portion 30 is shown in more detail below in connection with FIG. 5. Peristaltic pump portion 30 operates with a peristaltic pump actuator located in the dialysis machine. Each of the flow paths 26a to 26d defined by flexible sheeting cassette 10a includes or defines a valve contact portion 28a to 28d, respectively. Flow paths 26a to 26d and respective valve contact portions 28a to 28d are shown in more detail below in connection with FIG. 4.

In system 100a, fluid from one of the supply bags 12a to 12c is pumped through peristaltic pump portion 30, through a pump outlet pathway 32, through a to-heater pathway 34a, through a to-heater connector 36a, through an external to-heater tube 38a and finally to an external inline heater 40, which includes a fluid heating pathway 42a. To- and from-heater connectors 36a and 36b are sealed to flexible sheeting cassette 10a in the same manner in one embodiment as are connectors 16a to 16c and 22 shown in detail below in connection with FIG. 4.

Figure 2:
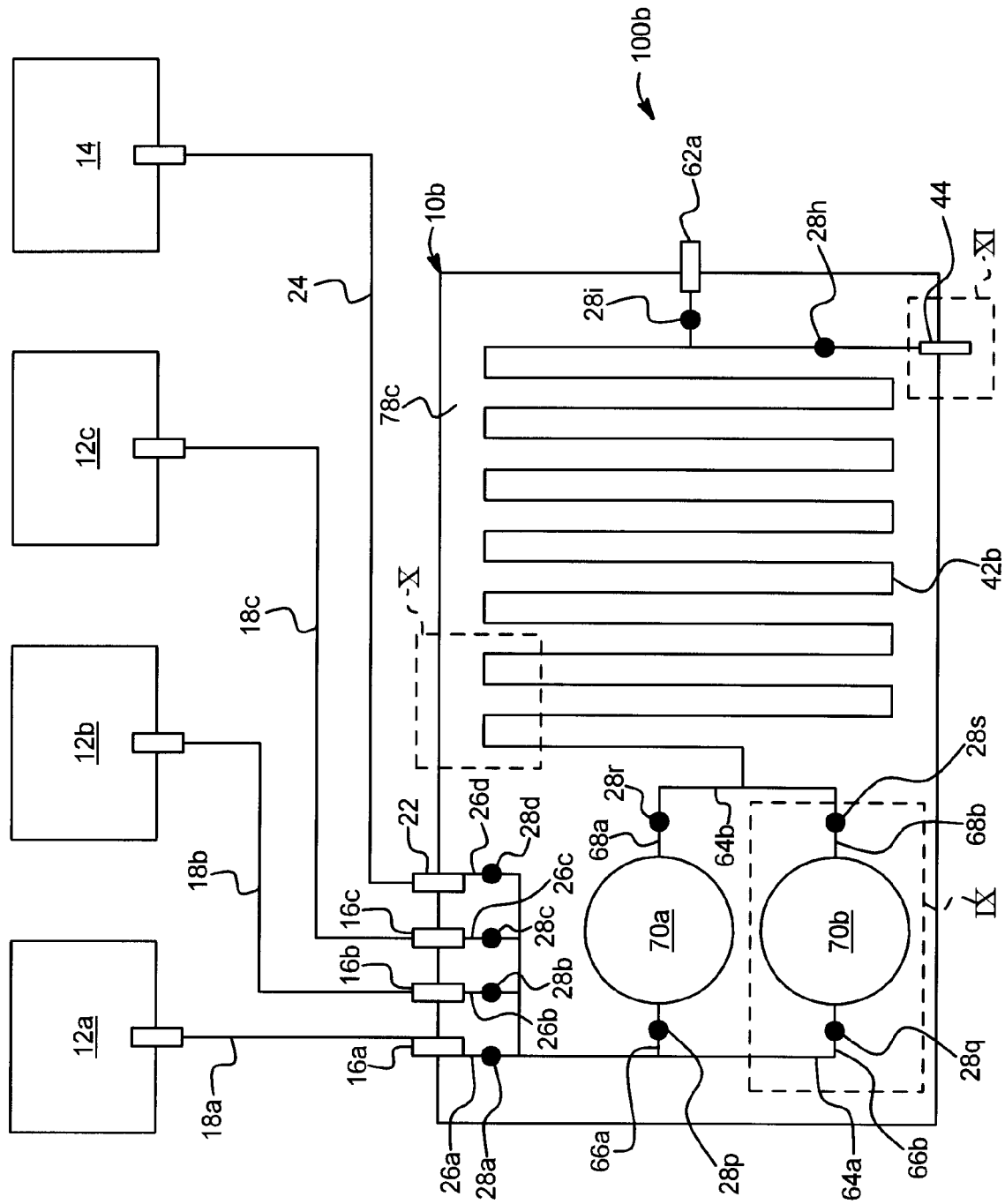
FIG. 2 is a schematic view of one embodiment of a cassette-based dialysis system employing a flexible sheeting cassette having a volumetric or membrane pumping portion and an inline heating portion.

External heater bag 40 defines a serpentine fluid heating pathway 42a, through which the fluid or dialysate travels. As the fluid or dialysate travels through the fluid heating pathway 42a, a plate, convective, radiant, inductive or other type of heater is used alone or in combination to heat the fluid. The heater heating the fluid flowing through heating pathway 42a can be located external to the dialysis machine that houses flexible sheeting cassette 10a or can be integrated into such machine. As seen in FIG. 2, a fluid heating pathway 42b is integrated alternatively into a flexible sheeting cassette 10b. One example of a fluid heating pathway is shown in more detail below in connection with FIG. 10A. FIG. 10B shows a two sided fluid heating pathway operating with a fluid heater.

Heated dialysate fluid flows from inline heater 40, through an external from-heater line or tube 38b, through a from-heater connector 36b of cassette 10a, through a from-heater pathway 34b defined by flexible sheeting cassette 10a, and to the volumetric control portion of cassette 10a, which is described in more detail below. To- and from-heating pathways 34a and 34b each define or include a valve contact portion 28e and 28f, respectively. Examples of valve contact portions are shown in more detail below by valve contact portions 28a to 28d of FIG. 4.

It should be appreciated that valve contact portions 28e and 28f are open when fluid is pumped to the patient, so that such fluid or dialysate can be heated. When fluid is pulled from the patient and pumped to drain, associated valve actuators close lines 34a and 34b at valve contact portions 28e and 28f. In the drain cycle, a valve actuator operates with valve contact portion 28g defined by or included in pump outlet pathway 32 to open pathway 32. In this manner, the heater and associated pathways and lines are bypassed during drain.

The materials used for supply bags 12a to 12c and drain bag 14 can be any suitable medical grade material, such as polyvinyl chloride ("PVC"), e.g., monolayer PVC films, non-DEHP PVC monolayer film, multilayer non-PVC films (wherein different layers are chosen to provide strength, weldability, abrasion resistance and minimal "sticktion" to other materials such as rigid cassette materials), polypropylene/polyethylene blend, polypropylene or Kraton blend, coextruded or laminated, with or without gas barrier, polyester, polyolefin, ULDPE. The materials used for external lines or tubes 18a to 18c, 24, 38a and 38b can be any suitable medical grade tubing material, such as PVC, non-DEHP PVC, polybutadiene ("PB"), ethylene vinyl acetate ("EVA"), polypropylene ("PP") blend, polyethylene ("PE") blend, Kraton blend and polyolefin blends. The materials used for external fluid heater bag 40 including fluid pathway 42*a* include PVC, PP/kraton blend.

The dialysis unit or machine (examples shown below in connection with FIGS. 21G and 22A) operating with flexible membrane cassette 10*a* includes an apparatus configured to detect air in the dialysate flow path. One highly suitable place to detect air or other gas bubbles in the system is at a point in the flow path just downstream of fluid heater 40. The heat from the heater causes air or other gas to egress from solution. Accordingly, an air detection sensor is positioned to operate with from-heater pathway 34*b* in one embodiment. Suitable air detectors are disclosed in the parent application of the present disclosure.

Valve actuators of cassettes 10*a* with valve contact portions 28*h* and 28*i* enable dialysate to be directed desirably and alternatively to either an inline vent 44 or to a volumetric balancing device or balancing chamber 50. If air is detected in the system, the valve actuator operating with valve contact portion 28*i* is closed, while the valve actuator operating with valve contact portion 28*h* is opened, allowing the fluid to reach vent 44, so that any air entrained in the fluid can escape from system 100*a*. One embodiment for vent 44 is shown in more detail below in connection with FIG. 11. Once the air is purged from flexible sheet 10*a*, the valve actuator operating with valve contact portion 28*h* is closed, while the valve actuator operating in combination with valve contact portion 28*i* is opened, allowing the purged dialysate to flow to balance chamber 50.

In an alternative embodiment cassette 10*a* is mounted vertically in the machine with vent 44 located at the top of the mounted cassette, such that any air in from-heater pathway 34*b* escapes automatically from vent 44. Here, separate valve actuators and valve seats 28*h* and 28*i* are not needed. Further if, vent 44 is pointed upwardly, separate valve actuators and valve seats 28*h* and 28*i* are not needed even if cassette 10*a* is mounted horizontally in the machine.

In an alternative embodiment, air in flexible sheeting cassette 10*a* is pumped to heater bag 40 or to drain bag 14. For example, air can be allowed to collect at the top of heater bag 40, which is laid horizontally on a heater plate in one implementation. If air is detected downstream of heater bag 40, appropriate valve seats 28 are switched so that the fluid is pumped to drain until no more air is detected.

Balance chamber 50 of the flexible sheeting cassette 10*a* (and other components discussed herein) includes three plies or flexible sheets in one embodiment. One embodiment of balance chamber 50 is shown below in connection with FIGS. 6 to 8, which will be discussed in more detail below. The three plies are sealed in a circular arrangement 52 in one embodiment to form upper and lower fluid compartments 54*a* and 54*b* (seen best in FIG. 7). Fluid pumped through pump outlet pathway 32 flows eventually through balance chamber inlet pathways 56*a* or 56*b* as determined selectively by valve actuators operating with valve contact portions 28*j* or 28*k*, respectively. In the embodiment illustrated in connection with FIGS. 6 to 8, balance chamber inlet pathway 56*a* is in fluid communication with upper compartment 54*a* of balance chamber 50, while balance chamber inlet pathway 56*b* is in fluid communication with lower balance chamber compartment 54*b*. As described in more detail below, fluid flows from compartments 54*a* and 54*b*, through balance chamber outlet pathways 58*a* and 58*b* as determined selectively by actuators operating with valve contact portions 28*l* and 28*m*, respectively.

Figure 6:
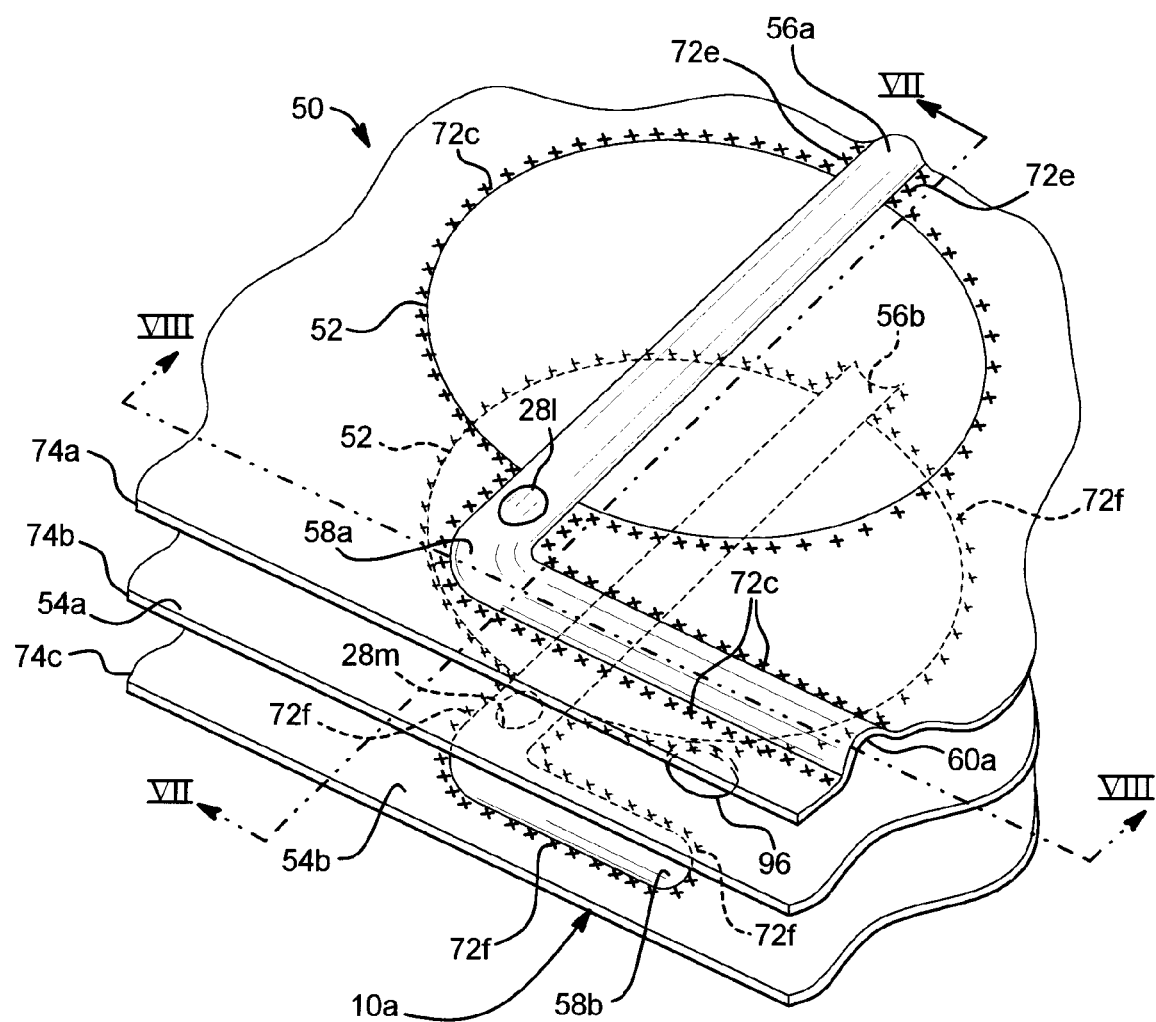
FIG. 6 is a sectioned perspective view of Detail VI shown in FIG. 1, which highlights one embodiment of a balancing chamber portion for the flexible sheeting cassettes.
Figure 8:
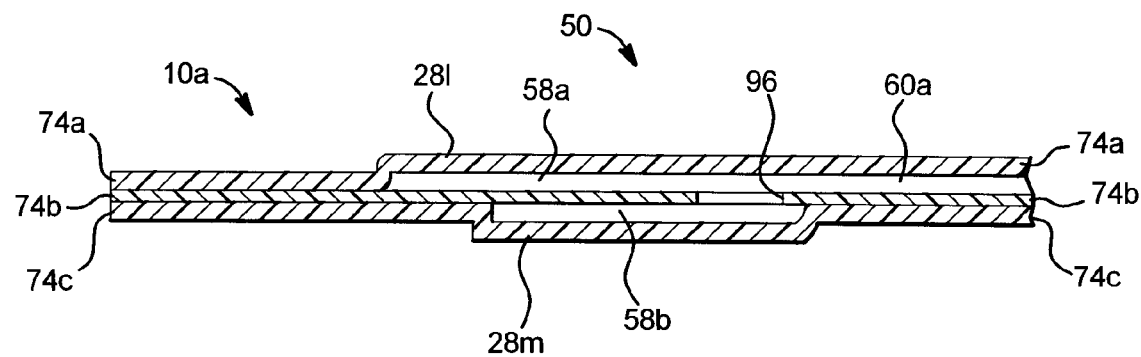
FIG. 8 is a sectioned view taken along line VIII-VIII of FIG. 6, which shows upper and lower fluid pathways leading to the balancing chamber portion of the flexible sheeting cassette shown in FIG. 6.

Fluid that flows through balance chamber outlet pathways 58*a* or 58*b* flows into a to-patient pathway 60*a* as seen in FIG. 1. FIGS. 6 and 8 show one embodiment for how fluid flowing through separate balance chamber outlet pathways 58*a* and 58*b* eventually tees together into a single to-patient pathway 60*a*.

The illustrated system 100*a* of FIG. 1 can be used with APD, tidal flow PD, or CAPD, for example, which typically uses a single connection to the patient for batch-type fill and drain cycles. In such a case, to-patient pathway 60*a* also serves as a from-patient pathway that communicates with connector 62*a*. To perform a drain cycle, connector 62*a* becomes a from-patient connector, to-patient pathway 60*a* becomes a from-patient pathway, outlet pathways 58*a* and 58*b* to the balance chamber compartments become inlets, and the previously described inlets 56*a* and 56*b* at the balance chamber compartments become balance chamber outlets. The peristaltic pump operating with peristaltic pump portion 30 of cassette 10*a* is run in reverse, pulling spent dialysate from the patient's peritoneum, through balance chamber 50 and associated pathways and thereafter pushing the spent dialysate to a drain bag, house drain or other appropriate drain.

It is, however, possible to use system 100*a* in a hemodialysis treatment, which typically includes a dialyzer having a dialysate inlet and a dialysate outlet (not illustrated). Or system 100*a* could also be used with a PD system employing a dual lumen catheter. Here, a separate from-patient pathway 60*b* is teed into to-patient pathway 60*a*. A separate from-patient connector 62*b* is provided and placed in fluid communication with from-patient pathway 60*b*. Connectors 62*a* and 62*b* are fixed to flexible sheeting cassette 10*a* via the same apparatus and technique shown for example with connectors 16*a* to 16*c* and 22 in FIG. 4. Valve actuators are configured to operate with valve contact portions 28*n* and 28*o* to selectively allow fluid to flow either out to-patient connector 62*a* or in through from-patient connector 62*b*, respectively. To pump fluid out of cassette 10*a* to the patient or dialyzer, the valve actuator operating with valve contact portion 28*o* is closed, while the valve actuator operating with valve contact portion 28*n* is opened. To pump fluid into cassette 28*a*, the valve actuator operating with valve contact portion 28*n* is closed, while the valve actuator operating with contact portion 28*o* is opened.

Whether a single connector 62*a* is provided or dual connectors 62*a* and 62*b* are provided, system 100*a* is configured to pump fluid to and from a dialyzer using a desired sequence of pump-to dialyzer strokes and pump-from dialyzer strokes. For example, a peristaltic pump operating with peristaltic pump portion 30 could operate in a pump-to direction to stroke balance chamber 50 ten times, each time delivering a known volume of fluid out connector 62*a* to the dialyzer. Afterward, the peristaltic pump is reversed for a period of time causing for example twelve strokes of balance chamber 50 to occur, each time pulling a known amount of fluid from the dialyzer through connector 62*b*, through cassette 10*a*, to one of the drain bags. The additional number of stokes pulling fluid from the dialyzer constitutes an amount of ultrafiltrate removed from the patient. Alternatively balance chamber 50 is driven magnetically as described below in connection with FIGS. 26A and 26B.

It should be appreciated that system 100*a* could also be used to perform hemofiltration. Here, to-patient connector 62*a* is connected to the extracorporeal circuit directly, such that injectable quality replacement fluid can be introduced upstream or downstream (or both) of the hemofilter. The port of the hemofilter is connected to from-patient port 62*b* in a dual port configuration or to single port 62*a*, wherein the sequential stroke manner just described is used in either case.

In a similar matter, hemodiafiltration could be performed, wherein the line connected to to-patient connector 62*a* is connected to both the extracorporeal circuit directly and an inlet of the dialyzer. Again, the outlet of the dialyzer in HDF can be connected to from-patient port 62*b* or the single port 62*a* depending on the configuration of cassette 10*a* used.

Referring now to FIG. 2, an alternative system 100*b* employs an alternative flexible sheeting cassette 10*b*. System 100*b* includes many of the same components that system 100*a* includes. For example, system 100*b* includes supply containers 12*a* to 12*c* and drain container 14. As before, supply containers 12*a* to 12*c* are connected fluidly to cassette 10*b* via supply connectors 16*a* to 16*c* via supply lines 18*a* to 18*c*, respectively. Also, drain bag 14 is connected fluidly to drain connector 22 via drainline 24. Connectors 16*a* to 16*c* and 22 are each connected to flow paths 26*a* to 26*d*, wherein each of the flow paths has a valve contact portion 28*a* to 28*d*, respectively. Flow paths 26*a* to 26*d* all feed into a pump inlet manifold pathway 64*a*.

One primary difference between system 100*b* and system 100*a* is that system 100*b* uses volumetric or membrane pumps rather than peristaltic pumps. Here, an inlet manifold pathway 64*a* communicates fluidly with pump inlet pathways 66*a* and 66*b*, which each lead fluidly to a respective volumetric or membrane pumping portion 70*a* and 70*b*. Valve actuators operating with valve contact portions 28*p* and 28*q* enable fluid to be pumped selectively through either volumetric pump portion 70*a* or 70*b* as desired. Volumetric pump portions 70*a* and 70*b* operate with a pneumatic and/or mechanical pump actuator located within the dialysis machine as described in more detail below in connection with FIGS. 9A to 9C. Alternatively, the volumetric pump portions are actuated magnetically as shown below in connection with FIG. 28.

In FIG. 2, pump outlet pathways 68*a* and 68*b* extend from the outlet side of pump portions 70*a* and 70*b*, respectively, and feed into a pump outlet manifold pathway 64*b*. Fluid leaves the pump outlet manifold pathway 64*b* then enters an alternative integral inline fluid heating pathway 42*b* Inline, integral fluid heating pathway 42*b* is shown in more detail operating with a fluid heater in connection with FIG. 10A. Any air that escapes from the dialysate or other medical fluid (including blood) during heating within fluid heating pathway 42*b* can be selectively removed from the system via inline vent 44. One embodiment for vent 44 is shown in detail below in connection with FIG. 11. Air is alternatively pumped to drain or left in fluid heating pathway 42*b*. Cassette 10*b* can be mounted in machine vertically with vent 44 pointing upwardly to allow air to escape cassette 10*b* automatically and without valve actuator and valve seat 28*h* for such actuator. Further vent 44 can be pointed upwardly when cassette 10*b* is loaded such that valve actuator and valve seat 28*h* can be eliminated even if cassette 10*b* is loaded horizontally.

If no air is detected, heated dialysate is allowed via valve actuators operating with contact portions 28*i* and 28*h* to be pumped to the patient (dialyzer or hemofilter, etc.) via to-patient connector 62*a*. As described above in connection with system 100*a*, system 100*b* can alternatively include a from-patient connector 62*b* (not illustrated here). In either configuration, system 100*b* can perform sequential HD (including HHD), HF or HDF as described above.

In the illustrated configuration of system 100, flexible sheeting cassette 10*b* is configured to perform PD, such as CAPD, tidal flow PD and APD. Here, as described above, after dialysate has been allowed to dwell within the patient's peritoneum for a prescribed period of time, to-patient connector 62*a* becomes a from-patient connector, which receives spent dialysate from the patient. In the illustrated embodiment, spent fluid is pulled back through fluid heating pathway 42*b* via pumps 70*a* and 70*b*, which push the spent dialysate to a suitable drain bag or drain. In an alternative embodiment (not illustrated), cassette 10*b* provides a suitable bypass pathway and corresponding valve contact portions to enable returning spent fluid to bypass fluid heating pathway 42*b*.

As shown, one primary difference between system 100*b* and system 100*a* is the incorporation of fluid heating pathway 42*b* into the flexible sheeting cassette 10*b*. Here, the corresponding heater is placed in the same machine housing as the pump actuator and valve actuators. As discussed above, the separate inline heater bag 40 of system 100*a* can operate alternatively with a heater housed in the same unit as the pump and valve actuators of system 100*a* or with a heater provided separately from the pump and valve actuator unit. It should be appreciated that the integrated, inline pathway 42*b* of system 100*b* can be used with the peristaltic pump portion 30 and/or balance chamber 50 of system 100*a* of FIG. 1. Further, the separate heater bag 40 of system 100*a* can alternatively be used with the volumetric pump portions 70*a* and 70*b* of FIG. 2.

As discussed, one primary difference between system 100*b* and system 100*a* is the use of volumetric or membrane pump portions 70*a* and 70*b* as opposed to the peristaltic type pump used above for system 100*a*. Volumetric pump actuators operating with portions 70*a* and 70*b* pump a known amount or volume of dialysate with each pump stroke. The total volume pumped by volumetric or membrane pump portions 70*a* and 70*b* is determined by counting the number of pump strokes. The advantage here is that a separate volumetric control apparatus, such as balance chamber 50, is not needed. Two pump actuators operate out of phase with portions 70*a* and 70*b* to produce an at least substantially continuous flow of dialysate to and from the patient.

All the materials described above for system 100*a* are also applicable to like components of system 100*b*. In operation, one of the supply valves 28*a* to 28*c* is opened to enable fresh dialysate to flow from one of the supply bags 12*a* to 12*c* into one of pump portions 70*a* and 70*b*, via a respective supply pathway 26*a*, 26*b* or 26*c*. Pumped fluid flows through manifold 64*a*, through inlet pathway 66*a* or 66*b* into pump portion 70*a* or 70*b*, respectively. The fluid then flows through respective outlet pathway 68*a* or 68*b*, through outlet manifold 64*b*, through heating path 42*b* where it is heated, through to-patient fluid connector 62*a* into the patient.

Volumetric pump portions 70*a* and 70*b* can pump fluid to or from the patient using different valve sequencing. For example, to pump fluid to the patient the pump through portion 70*a* and to pull fluid into pump portion 70*a* the valve actuator operable with valve contact portion 28*p* is opened, while the valve actuator operable with valve contact portion 28*r* is closed. Next, the valves are switched to pump the volume out of portion 70*a*, through heating pathway 42*b* to the patient. To run in reverse, e.g., drain the patient, the above-described valve states are reversed to pull spent fluid into pump portion 70*a* and then to pump the spent fluid from pump portion 70*a* to a suitable drain.

Figure 3:
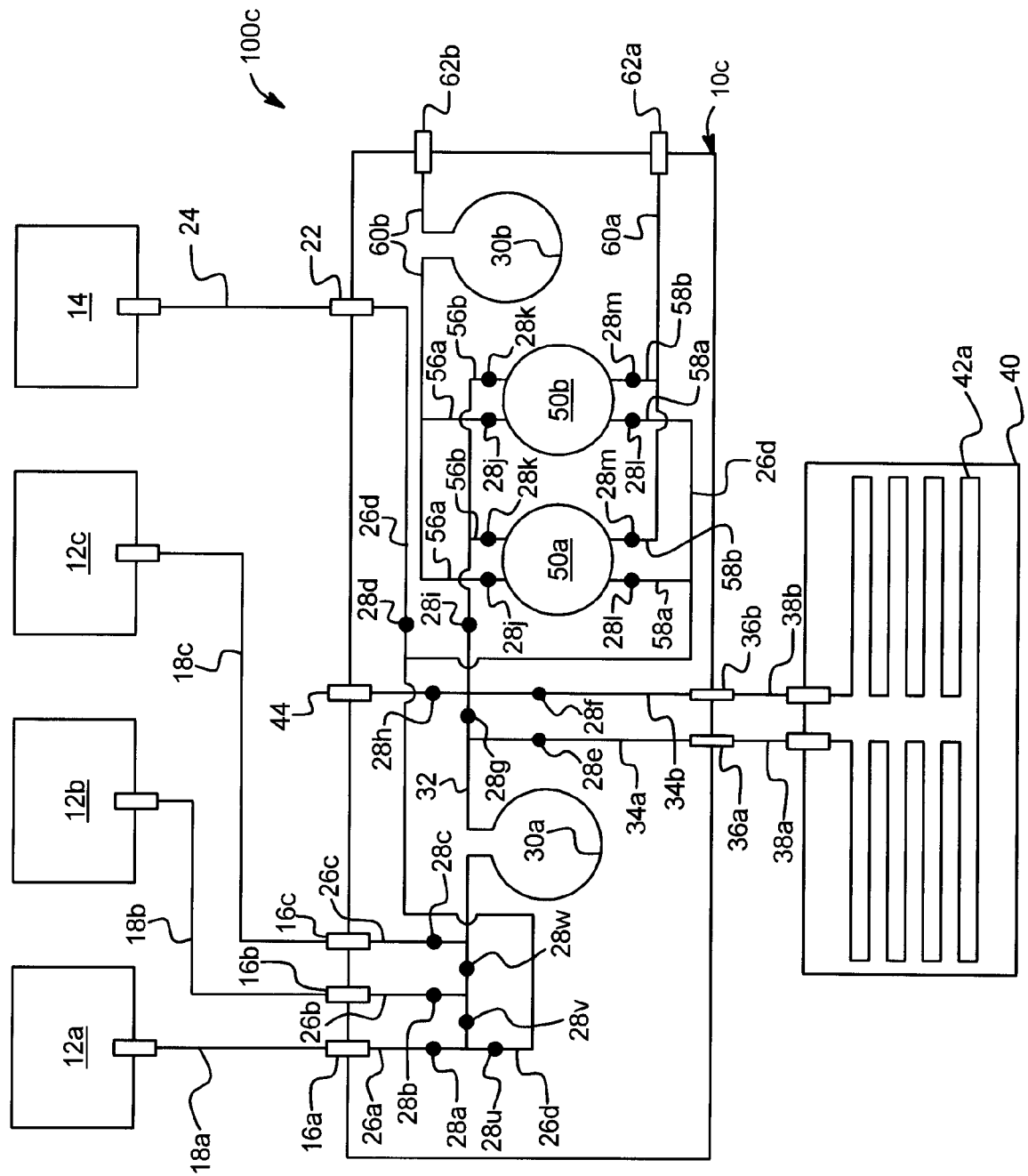
FIG. 3 is a schematic view of one embodiment of a cassette-based dialysis system employing a flexible sheeting cassette having dual peristaltic pumping portions, dual balancing chamber portions and an external heater bag.

Referring now to FIG. 3, a system 100*c* employing a third flexible sheeting cassette 10*c* is illustrated. System 100*c* is similar to system 100*a* of FIG. 1 and includes many of the same components, such as supply bags 12*a* to 12*c*, drain bag 14, supply connectors 16*a* to 16*c*, drain connector 22, and lines 18*a* to 18*c* connecting the supply bags to inlets connectors 16*a* to 16*c*, respectively. System 100*c* also includes a line 24 leading from drain connector 22 to drain bag 14. Flexible sheeting cassette 10*c* includes the same valve contact portions 28a to 28h as discussed above for system 100a. System 100c operates with a separate heater bag 40 having a fluid heating pathway 42a coupled to heater lines 38a and 38b and connectors 36a and 36b. The operation of vent 44 is as described above. Air is alternatively pumped to drain bag 14 or left in heater bag 40.

One primary difference between system 100c and system 100a is that it uses two separate peristaltic pump actuators operable with separate peristaltic pumping portions 30a and 30b. The illustrated configuration for the pumping portions is upstream of the fresh and spent inlets of the dual balance chambers 50a and 50b. This configuration allows for simultaneous, two-way pumping as discussed below.

System 100c provides dual balance chambers 50a and 50b. As seen, each balance chamber 50a and 50e operates with balance chamber inlet pathways 56a and 56b and balance chamber outlet pathways 58a and 58b. Each of those pathways includes a respective valve contact portion 28j, 28k, 28l or 28m, respectively.

Simultaneous, two-way pumping requires a to-patient pathway 60a connected fluidly to a to-patient connector 62a and a from-patient pathway 60b connected fluidly to a from-patient connector 62b. From-patient pathway 60b is connected fluidly to spent pump portion 30b and to balance chamber inlet pathways 56a leading to balance chambers 50a and 50b. Thus balance chamber inlet pathways 56a are spent fluid inlets and the spent fluid is driven by a pump actuator operating with peristaltic pump portion 30b.

Fluid inlet pathways 56b on the other hand are connected fluidly to pump outlet pathway 32 leading from supply pump portion 30a. Thus balance chamber inlet pathways 56b are fresh fluid inlets receiving fresh fluid driven by a pump actuator operating with peristaltic pump portion 30a. As shown below however, balance chambers 50a and 50b operate as secondary pumps, which accept a volume of fresh or spent fluid from fresh supply pumping portion 30a or from spent supply pumping portion 30b, respectively, and expel a like amount of spent or fresh fluid, respectively.

On the outlet side of balance chambers 50a and 50b, to-patient pathway 60a is connected fluidly to outlet pathways 58b. This overall path allows fresh fluid to be delivered from the balance chambers 50 (referring collectively to balance chambers 50a and 50b) to a dialyzer, extracorporeal circuit or the patient's peritoneum depending upon the therapy being used. Outlet pathways 58a are connected fluidly to a drain pathway 26d, which is fed to drain bag 14 or one of supply bags 12 acting as a drain bag, as determined by drain valve contact portions 28d, 28u, 28v and 28w. Alternatively, drain 14 is sized to hold the volumes from each of the supply bags 12a to 12c, eliminating contact portions 28u to 28w and simplifying drain pathway 26d.

In operation, system 100c can simultaneously deliver and remove fluid to and from the patient. To do so, in one half-cycle, for example, valve actuators operating with seats 28k and 28l of balance chamber 50a and valve seats 28j and 28m of balance chamber 50b are in an open-valve state, while valve actuators operating with valve seats 28 and 28m of balance chamber 50a and valve seats 28k and 28l of balance chamber 50b are in a closed-valve state. This configuration allows pump portion 30a to deliver a volume of fresh solution through inlet pathway 56b into balance chamber 50a, which in-turn forces a previously delivered like volume of spent solution to leave balance chamber 50a, through outlet pathway 58a, drain pathway 26d, to drain 14 or one of the supply bags 12a or 12b acting as a drain bag. Simultaneously, pump portion 30b delivers a volume of spent solution through inlet pathway 56a into balance chamber 50b, which in turn forces a previously delivered like volume of fresh solution to leave balance chambers 50b, through outlet 58b and to-patient line 60a to the patient.

Then, in a second half-cycle, valve seats 28k and 28l of balance chamber 50a and valve seats 28j and 28m of balance chamber 50b are closed, while valve seats 28j and 28m of balance chamber 50a and valve seats 28k and 28l of balance chamber 50b are opened. This configuration allows pump portion 30a to deliver a volume of fresh solution through inlet pathway 56b into balance chamber 50b, which in turn forces a previously delivered like volume of spent solution to leave balance chamber 50b, through outlet pathway 58a and drain pathway 26d, to drain or one of the supply bags 12a or 12b. Simultaneously, pump portion 30b delivers a volume of spent solution through from-patient line 60b and inlet pathway 58a into balance chamber 50a, which in turn forces a previously delivered like volume of fresh dialysate from balance chamber 50a through outlet pathway 58b, to-patient line 60a and to the patient.

As shown and described, balance chambers 50a and 50b ensure that a like volume of fresh and spent dialysate is delivered to and removed from the patient in each half-cycle. System 100c can remove excess fluid or ultrafiltrate in a number of ways. In one embodiment, both balance chambers 50a and 50b are filled with spent fluid. Next, valve contact portions 28l, 28k and 28n are opened and the pump actuator operating with pump portion 30a is run in reverse, pulling fluid from the patient through to-patient line 62a in the reverse direction. This action causes spent fluid to be pushed out drain pathway 26d to a drain via the spent fluid pulled in via pumping portion 30a. Now, both fresh compartments of balance chambers 50 are full of spent fluid and pump portion 30b causes spent fluid again to fill both spent compartments of chambers 50a and 50b with spent fluid. This causes a delivery of spent fluid from both fresh compartments of chambers 50 to the patient. A net fluid loss occurs because this volume came from the patient instead of the source. Alternatively, a valved bypass line is provided (not illustrated) leading from the to-patient line 60a to drain pathway 26d, so that the spent fluid is sent alternatively to a drain. The valved bypass line increases the UF efficiency but adds extra valves and flow paths. Either way, the above-described valve sequence is repeated as needed to remove a necessary amount of ultrafiltrate.

The above-described UF embodiments are administered intermittently. That is, they occur in some sequence with the non-UF or balanced strokes. For example, the control unit operating the pump and valve actuators could sequence system 100c to administer twelve balanced strokes and then three UF strokes. By the end of therapy, the cumulative volume of the UF strokes achieves the target UF volume, which is the volume of fluid that needs to be removed to return the patient to his or her "dry weight" as that term is known in the art.

In an alternative embodiment, system 100c provides a third peristaltic pump operating with a third UF peristaltic pumping portion (not illustrated but configured and valved at least substantially the same as pumping portions 30a and 30b) and a third UF balance chamber (not illustrated but configured and valved at least substantially the same as balance chambers 50a and 50b). In one embodiment, the inlet of the UF pumping portion tees into from-patient line 60b or connects separately to a from-patient tube extending from to the patient to from-patient connector 62b.

The outlet of the UF pump portion feeds into both compartments of the UF balance chamber. Valves are provided to allow the UF pump portion to fill a first compartment of the UF balance chamber with spent fluid, thus emptying the second compartment of the UF balance chamber of spent fluid. Next, the second compartment is filled, emptying the first compartment of spent fluid to complete a full cycle. In each cycle a known amount of spent fluid is removed as UF. Fluid emptied from the UF balance chamber is sent via drain pathway 26*d* to drain 14 or one of the supply bags 12 acting as a drain bag as described above.

The UF cycle is repeated as necessary to achieve the target UF removal volume. Importantly, this can be done while pumping portions 30*a* and 30*b* and balance chambers 50*a* and 50*b* deliver/remove a matched volume of fresh/spent fluid to/from the patient. It may be beneficial to have the ability to run the UF pumping portion and the UF balance chamber continuously, e.g., at a constant rate or at a varying rate according to a patient profile over the course of therapy. To do so, the valves controlling the UF balance chamber are switched at greater or lesser frequencies. The UF balance chamber may be sized differently, e.g., smaller than balance chambers 50*a* and 50*b* for finer control of UF.

Figure 12A:
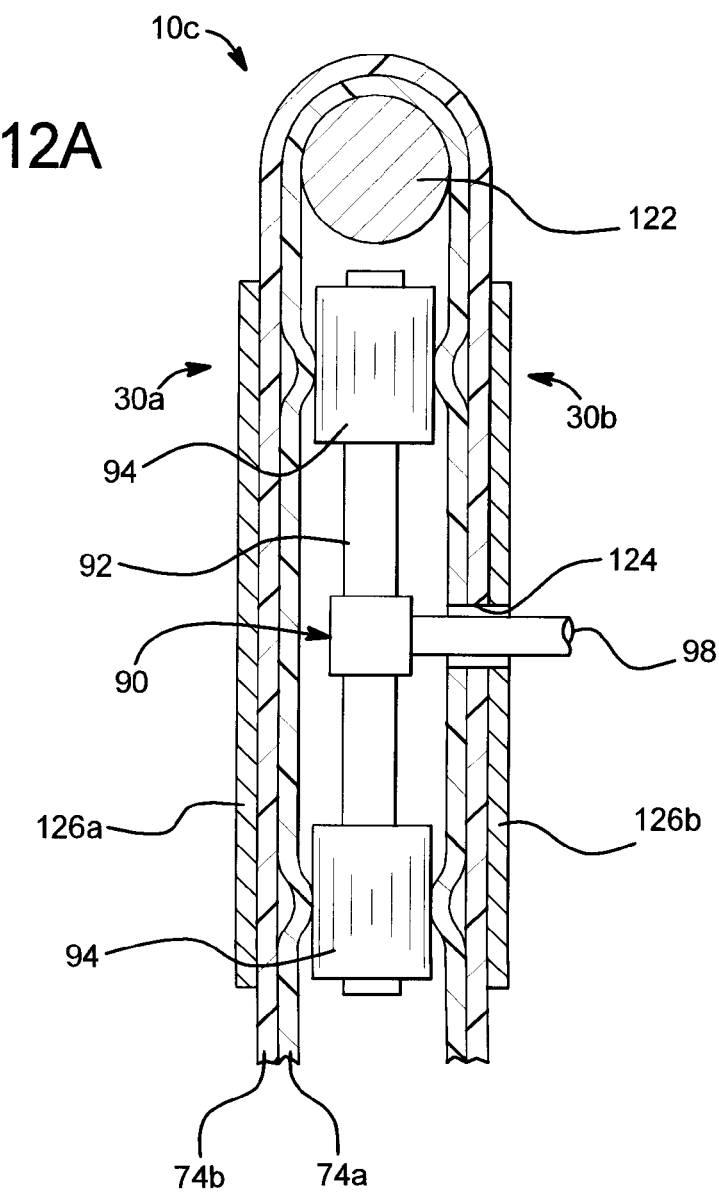
FIG. 12A is a sectioned elevation view illustrating one embodiment for configuring a single peristaltic pump actuator to drive fluid through two different flow paths of the flexible sheeting cassettes.
Figure 12B:
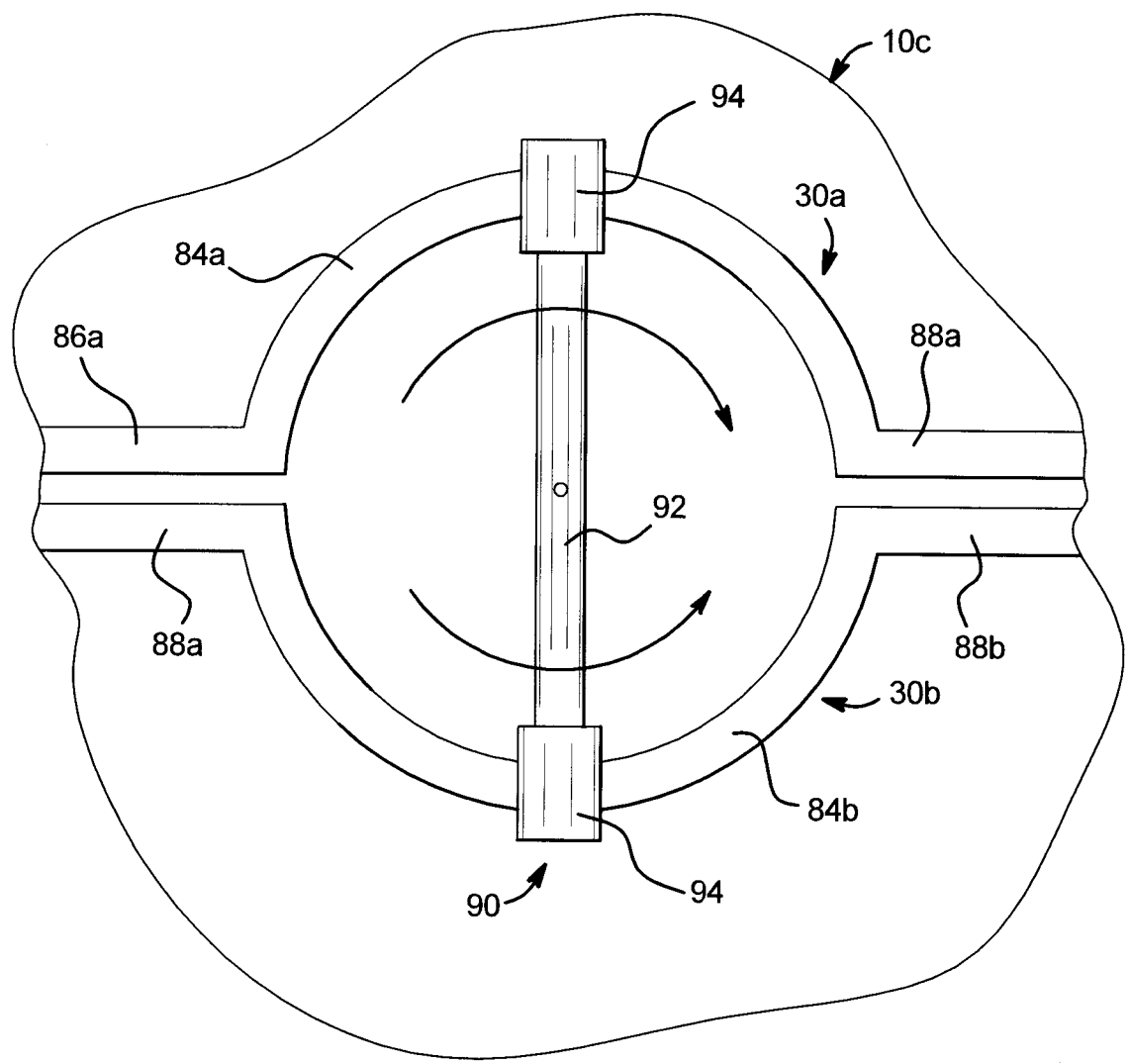
FIG. 12B is a plan view illustrating another embodiment for configuring a single peristaltic pump actuator to drive fluid through two different flow paths of the flexible sheeting cassettes.

The third pump operating with the UF pumping portion can be run at any desired speed relative to the pumps operating with balanced pumping portions 30*a* and 30*b*. FIGS. 12A and 12B show peristaltic pump embodiments in which a single roller drives two flexible sheeting cassette pumping portions. Given the above need for varying UF pump speed, the two pumping portions driven by the same roller (and thus at the same speed) would be matched flow portions 30*a* and 30*b* in one embodiment. The UF pumping portion would then operate with its own roller.

In a further alternative embodiment, the third UF balance chamber is provided but a third pumping portion is not. Here, the spent fluid pumping portion 30*b* drives the UF balance chamber off of the return pathway 60*b* (downstream of spent fluid pumping portion 30*b*) in addition to balance chambers 50*a* and 50*c*. That is, the first and second compartments of the UF balance chamber are connected fluidly with the return pathway 60*b* downstream of spent fluid pumping portion 30*b*. The valves controlling the UF balance chamber are again switched at greater or lesser frequencies to control UF rate.

It should be appreciated that separate UF pumping portions and volumetric control devices can also be provided for systems 100*a* and 100*b* of FIGS. 1 and 2. For example, a separate peristaltic pumping portion and balance chamber can be provided for system 100*a* of FIG. 1. A third volumetric UF pump can be provided for system 100*b* of FIG. 2. Such configurations allow for simultaneous balanced and UF strokes. In any of the above-described configurations, any of the balancing chambers and/or UF pumping portion can be driven alternatively magnetically as shown below in connection with FIGS. 26A, 26B, and 27.

Figure 4:
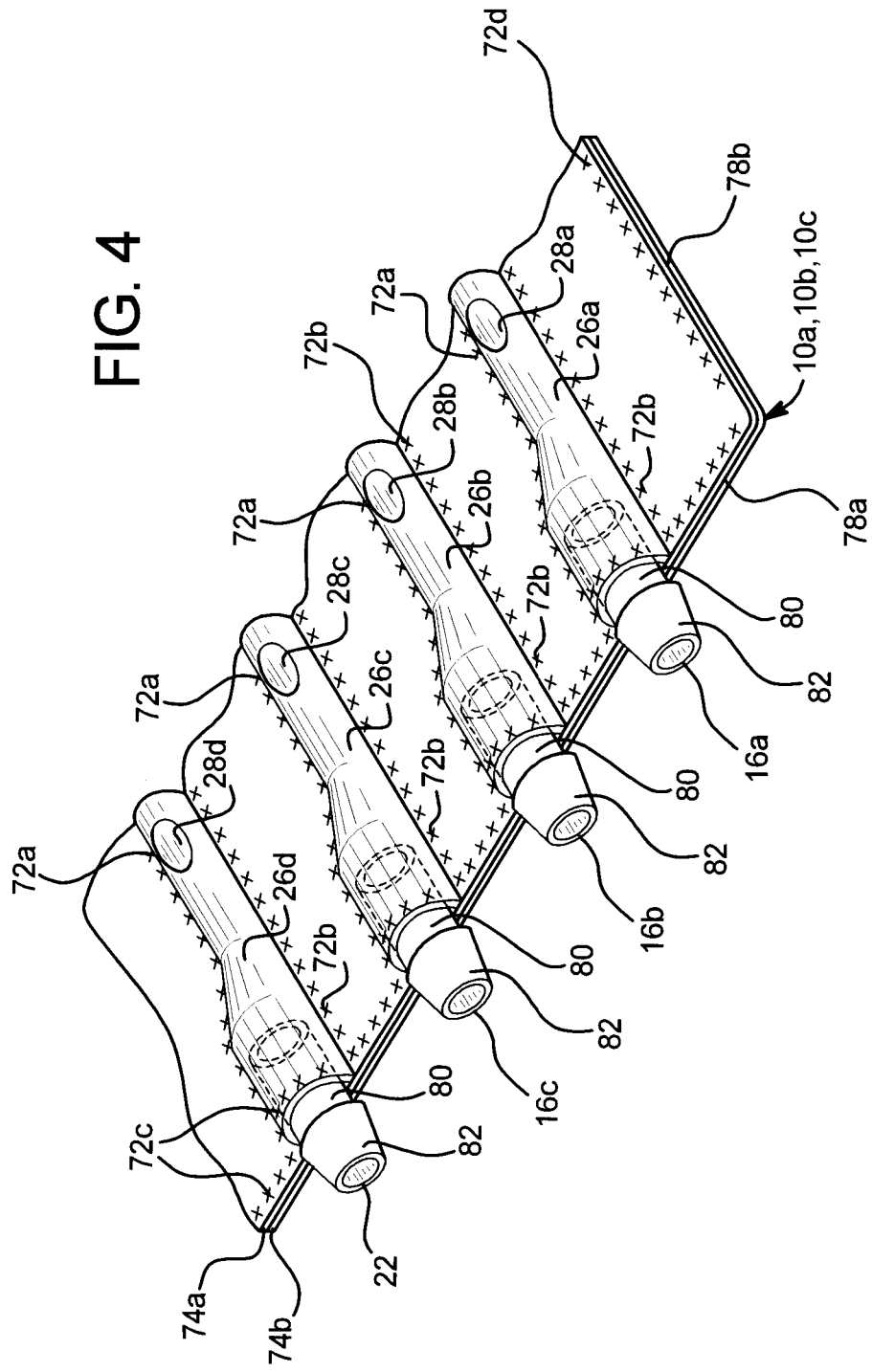
FIG. 4 is a sectioned perspective view of Detail IV shown in FIG. 1, which highlights one embodiment of an inlet/outlet connector portion of the flexible sheeting cassettes.

Referring now to FIG. 4, Detail IV of FIG. 1 is shown in detail and in perspective view. FIG. 4 shows one embodiment for sealing connectors, such as supply connectors 16*a* to 16*c* and drain connector 22 between two plies or sheets 74*a* and 74*b* (which may be separate sheets or folded from the same piece of material) of flexible sheeting cassette 10*a*. It should be appreciated however that the teachings of FIG. 4 apply to any of the sheeting cassettes 10 (referring collectively to flexible sheeting cassettes 10*a*, 10*b*, 10*c*, etc.) and also to any type of connector, such as to- and from-heater connectors 36*a* and 36*b* and to- and from-patient connectors 62*a* and 62*b*.

In the illustrated embodiment, connectors 16 (referring to 16*a* to 16*c* collectively) and 22 each include a connector body 80, which can be semi-rigid or rigid. Suitable materials for body 80 include semi-rigid or rigid polymers or plastics, such as, Acrylic and Cyclic Olefin Copolymer ("COC"). Body 80 includes or defines a sealing apparatus 82, such as a luer fitting, ferreled fitting, other type of press-fit or threaded seal. In one embodiment, supply lines 18 and drainline 24 (not shown) are removeably or permanently sealed around fitting 82. The seal can rely on press-fit alone or be aided by a medically suitable adhesive, chemical bond or weld, such as an ultra-sonic, heat or other type of weld.

In one alternative embodiment, lines 18 (referring to 18*a* and 18*c* of FIG. 1 collectively) and 24 fit sealingly and removeably or permanently to body 80. A permanent seal can include any of the bonding techniques discussed above, such as adhesive, heat energy, etc. In another alternative embodiment (not illustrated) one or both of first and second plies 74*a* and 74*b* is thermo-formed to form a male port that extends outwardly from the front edge 78*a*. Supply or drain lines 18 and 24 can then seal removeably or permanently around or inside the thermoformed port via any of the techniques discussed above.

As illustrated by the rows of X's (used throughout the application to illustrate a sealed seam), first ply 74*a* is sealed longitudinally at seals 72*a* and 72*b* to second ply 74*b* on either side of body 80. Seals 72*a* and 72*b* can also include a seal of plies 74*a* and 74*b* to body 80. As seen, seals 72*a* and 72*b* extend inwardly from bodies 80 to seal and form supply flow pathways 26*a* to 26*c* and drain pathway 26*d*.

In the illustrated embodiment, pathways 26 are formed by thermo-forming a longitudinal, at least substantially semi-circular arc in one or both first and second plies or sheets 74*a* and 74*b*. Suitable processes for making such longitudinal arc include thermoforming and injection molding. In an alternative embodiment, the arc is not pre-formed, rather, seals 72*a* and 72*b* define relatively flat flow paths 26 (referring collectively to flow paths 26*a* to 26*d*, etc.) and the pumps are sized and configured to force fluid through the at least substantially flat plies 74*a* and 74*b* forming pathways 26. Further alternatively, one or more temporary tube rod or other template instrument can be laid on sheet 74*a* or 74*b*. Sheet 74*a* or 74*b* is stretched over the tube or template and welded to sheet 74*b* or 74*a*, respectively. The tube or template is removed leaving pathways 26.

A seal 72*c* is made along front edge 78*a* of flexible sheeting cassette 10*a*. Seal 72*c* includes a sheet 74*a* to sheet 74*b* seal in certain places and a circumferential sheet 74*a*/74*b* to body 80 seal at connectors 16 and 22. A seal 72*d* is made along side edge 78*b* of flexible sheeting cassette 10*b*. Seal 72 (referring collectively to seals 72*a*, 72*b*, 72*c*, 72*d*, etc.) can be made via any one or more of the adhesive, chemical or welding embodiments discussed herein. Further, edges 78*b* can be formed alternatively by folding a single piece of material at edge 78*b* to form first and second sheets 74*a* and 74*b*. Still further, edges 78*a* and 78*b* can be welded to a rigid frame that provides structural support for sheeting cassettes 10*a*, 10*b* and 10*c*. The frame aids in the handling and loading of the cassette.

In the illustrated embodiment, bodies 80 of connectors 16 and 22 are at least substantially cylindrical. In an alternative embodiment, bodies 80 are flared or tapered to provide enhanced sealing surfaces for sealing to upper and lower plies 74*a* and 74*b*. One configuration for tapered bodies 80 is shown and described in U.S. patent application Ser. No. 10/155,384, entitled Disposable Medical Fluid Unit Having Rigid Frame, filed May 24, 2002, owned by the assignee of the present application, the entire contents of which are incorporated herein by reference.

Valve contact portions or seals 28*a* to 28*d* in the illustrated embodiment are flat sections or indents formed or made at the appropriate positions along flow paths 26. The flat sections or indents can be formed in the process of forming paths 26 or be made in paths 26 after the paths are formed. The flats or indents tend to increase the contact area with flat headed valve actuators. It is contemplated however that valve contact portions or seals 28 do not have a different configuration from the rest of flow paths 26 and are simply areas at which the valve actuator contacts the flow paths 26. Here, the head configuration and force of the valve actuator is sufficient to close the semi-circular or circular flow paths 26 when called upon to do so. The valve actuator can be pneumatically, mechanically, hydraulically and/or electrically actuated. For example, a fail-safe valve actuator is used in one embodiment, which is closed via a spring force and opened via a vacuum. The valve actuators are opened and closed pneumatically alternatively. Further, the valve actuators can be cams driven by a cam shaft.

Figure 5:
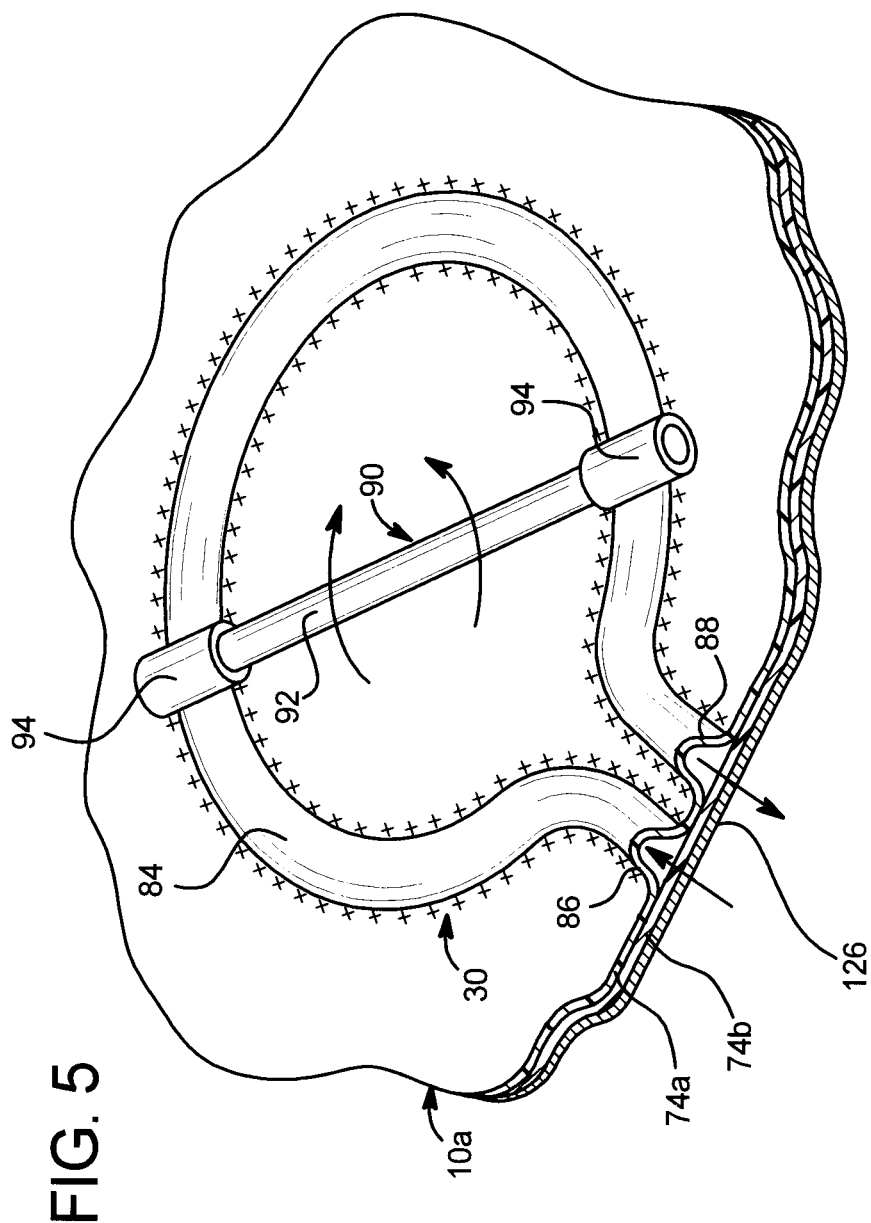
FIG. 5 is a sectioned perspective view of Detail V shown in FIG. 1, which highlights one embodiment of a peristaltic portion for the flexible sheeting cassettes.

Referring now to FIG. 5, Detail V of FIG. 1 is shown in more detail and in perspective view. FIG. 5 shows one embodiment for peristaltic pump portion 30 (including pump portions 30*a*, 30*b*, etc.). Pump portion 30 includes an at least substantially circular flow path 84, which is formed using upper and lower plies 74*a* and 74*b* via any of the methods discussed herein and includes any of the configurations discussed above for fluid pathways 26. Peristaltic pump inlet 86 and peristaltic pump outlet 88 communicate fluidly with peristaltic flow path 84 and with supply pathways 26*a* to 26*c* and pump output pathway 32, respectively, shown above in connection with FIGS. 1 and 3. Inlet 86 and outlet 88 are placed in an at least substantially parallel, adjacent relationship with respect to each other in the illustrated embodiment to maximize the distance or throw of peristaltic pumping pathway 84.

As shown, peristaltic pump portion 30 operates with a peristaltic pump actuator 90. Peristaltic pump actuator 90 generally includes components known to those of skill in the art, such as a drive shaft 92 and at least one roller 94 driven rotatably by drive shaft 92. One difference between the peristaltic configuration of FIG. 5 and that of known peristaltic pumps is that known pumps typically use round tubing that is looped inside of a circular race. That is, the outer circumference of the loop is abutted against the race. The drive shaft rollers contact the inner circumference of the loop and pinch the tube radially against the race. In FIG. 5, on the other hand, a race or press-plate 126 is located behind second sheet 74*b*. The race or press-plate 126 is part of the dialysis machine in one embodiment and, for example, can be part of a door that is closed against flexible sheeting cassette 10*a* or 10*c* after it has been loaded into the machine. Rollers 94 are located within the machine on the opposing side of cassette 10*a* or 10*c*.

Rollers 94 spin in substantially a same plane in which sheets 74*a* and 74*b* reside and press pathway 84 in multiple places against plate 126 to drive fluid from inlet 86 to outlet 88. In particular, shaft 92 spins such that rollers 94 create negative and positive pressure gradients to drive fluid from inlet 86 to outlet 88. The thermo-formed flow paths are configured to withstand, e.g., not collapse or close, forces created by the vacuum or negative peristaltic pressures. As seen via the arrows FIG. 5, shaft 92 can be driven bi-directionally if needed as described above.

Figure 7:
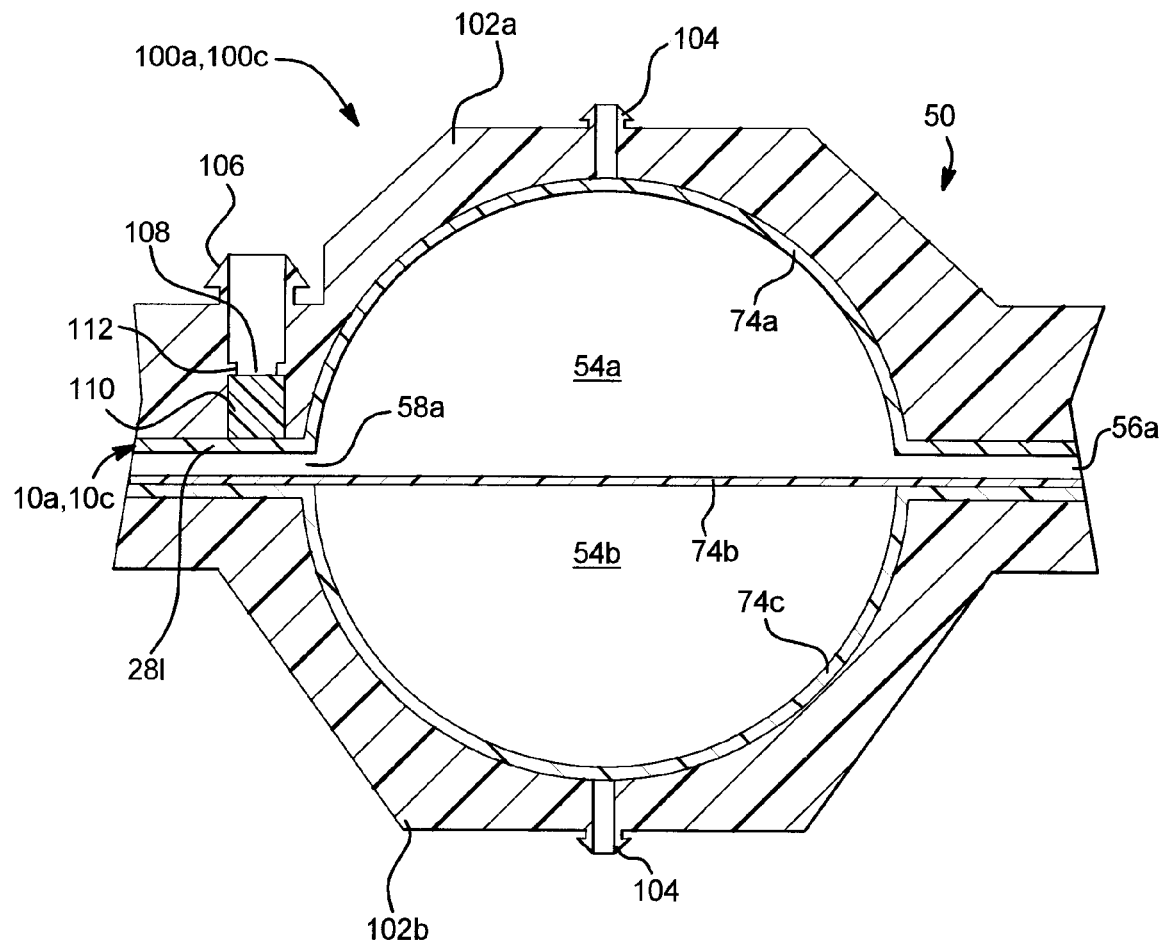
FIG. 7 is a sectioned elevation view taken along line VII-VII of FIG. 6, illustrating the balancing chamber portion of the flexible sheeting cassette in operation with a dialysis machine.

Referring now to FIG. 6, one embodiment for balance chamber 50 (referring generally to balance chambers 50*a*, 50*b*, etc.) used in flexible sheeting cassettes 10*a* and 10*c* is illustrated. FIG. 6 shows Detail VI of FIG. 1 shown in perspective view. FIGS. 7 and 8 are cross-section views of FIG. 6 taken along lines VII-VII and VIII-VIII, respectively, shown in FIG. 6. As seen in FIGS. 6 to 8, balance chamber 50 uses three plies or sheets 74*a* to 74*c* of flexible material. Various embodiments for sealing three separate plies together are discussed herein. Three sheets 74*a* to 74*c* may be completely separate or folded twice from the same piece of material.

As seen in FIG. 6 and discussed above, balance chamber 50 includes a sealed circle 52 formed by a first seal 78*e* shown by the circular axis between first sheet 74*a* and second sheet 74*b*. The chamber formed within the circular seal 72*e* between sheets 74*a* and 74*b*, which form the upper balance chamber compartment 54*a* as seen also in FIG. 7. A second seal 72*f* is shown in phantom in FIG. 6 in which it resides beneath sheet 74*a* and is made about the same sealed circle 52 between second sheet 74*b* and third sheet 74*c*, which form lower balance chamber compartment 54*b*. In an embodiment, seals 72*e* and 72*f* are made at the same time or as the same seal, so that a single sealing process, e.g., a welding or chemical bonding process, forms both seals 72*e* and 72*f* simultaneously and associated comparatively. It is contemplated, however, to form one of seals 72*e* and 72*f* first and thereafter form the second of the two seals 72*e* and 72*f*. Seals 72*e* and 72*f* can be made via any of the methods described herein. Additional seals (not illustrated) are made along the edges of the three sheets 74*a* to 74*c* and elsewhere in cassette 10*a* or 10*c* as discussed herein.

In the illustrated embodiment seal 72*e* extends to form balance chamber inlet 56*a* and balance chamber outlet 58*a*. Enough of balance chamber outlet 58*a* is seen such that valve contact portion or seat 28*l* shown in FIG. 1 is also seen in FIGS. 6 and 7. Seal 72*f* also extends to form balance chamber inlet 56*b* and balance chamber outlet 58*b*. Enough of balance chamber outlet 58*b* is illustrated so that valve seat 28*m* is shown in hidden and in phantom in FIG. 6 and is also seen in FIG. 8. As seen in FIG. 1, balance chamber outlet pathways 58*a* and 58*b* combine into two patient pathway 60*a*. FIGS. 6 and 8 illustrate one embodiment for enabling fluid to travel between two flexible sheeting pairs or levels. As seen, middle flexible sheet 74*b* defines an aperture or opening 96, which is located directly above the distal end of balance chamber outlet 58*b* and is inline with balance chamber outlet 58*a* and the subsequent to-patient pathway 60*a*. In this configuration, fluid exiting lower balance chamber compartment 54*b* travels through balance chamber outlet 58*b*, upwardly through second sheet 74*b* via aperture 96, into balance chamber outlet 58*b* and to patient pathway 60*a*, which are located and defined by flexible sheets 74*a* and 74*b*.

FIG. 8 illustrates a cross section of sealed plies 74*a* to 74*c* from a front view as cassette 10*a* is sectioned through pathways 58*a* and 58*b* shown in FIG. 6. As seen, in FIG. 8 valve seat 28*m* is located laterally offset from valve seat 28*l*, so that cooperating valve actuators can open and close pathways 58*a* and 58*b* independently. That is, a valve actuator can close either valve seat 28*l* or 28*m* without also closing either of flow path 58*b* or 58*a*, respectively. FIG. 8 also shows aperture 96 in cross section, which is formed in sheet 74*b* and which enables fluid communication between paths 58*a* and 58*b*, so that flow from upper and lower compartments 54*a* and 54*b* can be combined into to patient pathway 60*a*. FIG. 8 further shows that pathways 58*a* and 58*b* can be raised via thermoforming or other method to provide a gap between the inner surface of plies 74*a* and 74*c* and the outer surfaces of ply 74*b*.

Referring now to FIG. 7, one apparatus and method for operating balance chamber 50 (referring generally to each of the balance chambers described herein) is illustrated. Balance chamber 50 is shown in operation with a portion of the dialysis machine 100*a* and 100*c* (operating with cassettes 10*a* and 10*c*, respectively). Dialysis machine 100*a* or 100*c* includes or defines first and second chamber forming members 102*a* and 102*b*. For example, one of members of 102*a* or 102*b* is stationary and configured to accept a flexible sheeting cassette, such as cassette 10a or 10c. The other of chamber forming members 102a or 102b is part of a door that is closed onto the opposing side of flexible sheeting cassette 10a and 10c after it has been loaded into dialysis machine 100a or 100c.

Chamber forming members 102a and 102b each define or include a port 104 to which a tube (not illustrated) is releasably or permanently secured via any of the methods and embodiments discussed above in connection with connectors 16 and 22 of FIG. 4. In an embodiment, after cassette 10a or 10c is loaded into machine 100a or 100c, a negative pressure or vacuum is drawn on ports 104, pulling first and third plies or sheets 74a and 74c against the inner at least substantially spherically shaped cavities defined by first and second members 102a and 102b. Although members 102a and 102b are shown defining at least substantially spherical shapes, other suitable cross-sectional shapes maybe used, such as substantially triangular or substantially trapezoidal shapes. Further, although not illustrated, members 102a and 102b can define air channels that extend radially from ports 104 in various directions to help spread the vacuum across a larger surface of plies 74a and 74c. Such channels are shown and described in U.S. Pat. No. 6,814,547, entitled Medical Fluid Pump, assigned to the assignee of the present application. Once sheets 74a and 74c are pulled via vacuum against the inner surface of chamber forming members 102a and 102b, respectively, balance chamber 50 is ready for operation. In an alternative embodiment, negative pressure is not applied against sheets 74a and 74c and thus ports 104 are not needed. Here, the positive pressure of the dialysate or fluid is enough to spread, respectively, sheets 74a and 74c against members 102a and 102b, respectively, and to drive middle sheet 74b between sheets 74a and 74c.

FIG. 7 illustrates a state of operation in which no fluid has been delivered to balance chamber 50. Accordingly, middle or driving sheet 74b is not pushed towards either upper sheet 74a or lower sheet 74c. Section VII-VII taken through the detail of FIG. 6, for FIG. 7 includes valve seat 23l. As seen in FIG. 8, valve seat 28m is not aligned with valve seat 28l with respect to the section plane along line VII-VII of FIG. 6. Accordingly, valve seat 28m is not seen in the sectioned view of FIG. 7 because that view valve seat 28m in that view resides in front of valve seat 28l. Valve seat 28l is shown operating with a valve actuator 106, which is part of machine 100a or 100c. For simplicity, valve actuator 106 is shown as an entirely pneumatically operated valve actuator. Here, positive air pressure is applied to the port of actuator 106 to force a plunger 108 to compress valve seat 28l against second sheet 74b to close balance chamber outlet 58a. Actuator 106 includes an o-ring seal 110, which creates a sliding seal between plunger 108 in the inner, e.g., cylindrical housing of valve actuator 106. To open balance chamber outlet 58a, a negative pressure is applied to port 106, pulling plunger 108 upwards against stop 112, enabling fluid to open seat 28l and flow outwardly from upper balance chamber compartment 54a through balance chamber outlet 58a. FIGS. 6 to 8 do not show valve seats 28j, 28k or 28l which communicate with valve actuators, such as valve actuator 106. These actuators and seats control the inlet of balance chamber 50a and the inlet and outlet of balance chamber 50b of FIG. 1.

In operation, to fill upper balance chamber compartment 54a, plunger 108 is pressurized and closes valve seat 28l and balance chamber outlet 58a. The valve actuator 106 operating with balance chamber inlet 56a is opened, enabling fluid to fill upper balance chamber compartment 54a. If fluid has already filled lower compartment 54b, the fluid entering compartment 54a pushes the fluid from lower balance chamber compartment 54b, through balance chamber outlet 58b to its destination. To do so, a valve actuator 106 operating with balance chamber outlet 58b is opened, while a valve actuator 106 operating with inlet 56b is closed. Because the volume defined by compartments 54a and 54b is fixed and because second sheet 74b is pushed all the way against sheets 74a or 74c in each half stroke, the same volume of fluid is outputted through balance chamber outlets 58a and 58b in each half stroke. Accordingly, flexible sheets 74a and 74c are made of a suitably stretchable, compliant and leak-free material such as one of those materials listed above for sheets 74 (referring collectively to sheets 74a to 74c). As discussed below in connection with FIGS. 26A and 26B, sheet 74b is made alternatively to be magnetic and driven alternatively magnetically.

Referring now to FIGS. 9A to 9C one apparatus and method of operating volumetric pumps 70 is illustrated. The portion of cassette 10b shown in FIG. 2 and marked as Detail IX is shown in front, cross-sectioned view in FIGS. 9A to 9C., which shows volumetric pump 70b. The teachings with respect to 70b are applicable to volumetric pump 70a.

Volumetric pump 70b is shown operating with a dialysis machine 100b, which uses cassette 10b. Machine 100b includes first and second pump chamber forming members 114a and 114b, which define the shape of the volumetric pump 70b. Cassette 10b is configured to be loaded within the machine 100b such that a circular flexible membrane portion of cassette 10b as seen in FIG. 2 is in alignment with the spherically shaped chamber defined by pump chamber forming members 114a and 114b. Also, valve seats 28q and 28s are aligned with valve actuators 106 shown in FIGS. 9A to 9C. Valve actuators 106 operate as described above in connection with FIG. 7 and include a plunger 108, which slides back and forth within the actuator body.

Chamber 70b uses first and second flexible sheets 74a and 74b. First and second pump chamber forming members 114a and 114b each include a port 104 described above in connection with FIG. 7. As discussed below, negative and positive pressure are used to drain sheets 74a and 74b. Alternatively, one of sheets 74a or 74b can be driven mechanically. A suitable hybrid mechanical/pneumatic pump is shown and described in U.S. Pat. No. 6,819,547 listed above. Although the spherical shape shown in FIGS. 9a to 9c is one suitable shape, other shapes could be defined for volumetric pump 70, such as a trapezoidal or triangular shape.

FIG. 9A shows an initial state for volumetric pump 70b. Here, negative pressure is applied to port 104 of chamber forming member 114b, which pulls second flexible sheet 74b to conform with the inner surface of second chamber forming member 114b. At the same time, positive pressure is applied to port 104 of first pump chamber forming member 114a. The positive pressure causes first flexible sheet 74a to be pressed against second flexible sheet 74b. In FIG. 9A, a positive pressure is applied to both valve actuators 106, closing valve seats 28q and 28s. Again, valve actuators 106 can be any combination of pneumatic, mechanical and/or electrically operated. As further seen in FIG. 9A, dialysate or medical fluid (including blood) 116 is pressurized against valve seat 28q, but is precluded from entering into the sealed chamber of volumetric pump 70b.

In FIG. 9B, the negative pressure at port 104 of lower pump chamber forming member 114b is maintained as is the positive pressure applied to valve actuator 106 at valve seat 28s. A negative pressure is applied to valve actuator 106 at valve seat 28q, which pulls and holds plunger 108 to and against stop 112, allowing fluid 116 to flow through pump inlet pathway 66b and into the chamber of volumetric pump 70b. The force of fluid 116, e.g., via gravity may be enough to cause first flexible member 74a to be pushed against inner surface of upper pump chamber forming member 114a. Alternatively, a negative pressure can be applied at port 104 of member 114a to pull first flexible sheet 74a against the inner surface of the member. This action causes a vacuum, which pulls fluid 116 into the pump chamber. As with the peristaltic pump, the thermo-formed flow paths are configured to withstand, e.g., not collapse, under the negative pressure of the membrane pumping. In either case, fluid 116 fills the at least substantially spherical cavity between sheets 74a and 74b and stops against valve seat 28s, which is still in its closed position.

In FIG. 9C, valve seat 28q is closed, while valve seat 28s is opened. Negative pressure is maintained at lower port 104, so that sheet 74b is pulled against member 114b. Here, a positive pressure is applied to port 104, closing first flexible sheet 74a against second flexible sheet 74b, causing fluid 116 to be pushed out of the at least substantially spherical chamber of volumetric pump 70b, through pump outlet pathway 68b, to its desired destination. First and second membranes 74a and 74b are now at the position showed in FIG. 9A, so that pump 70b is able to repeat the above described cycle as soon as valve seat 28s is closed. As shown below in connection with FIG. 28, membranes 74a and 74b are made alternatively to be magnetic and driven alternatively magnetically.

The pump out and fill strokes of pumps 70a and 70b in FIG. 2 can be staggered such that the flow of dialysate or medical fluid (including blood) through cassette 10b is at least substantially continuous. Because the volume formed by the chamber of members 114a and 114b is known and because first flexible sheet 74a is moved repeatedly to the upper and lower surfaces of the chambers, the volume of fluid pumped with each stroke is known and repeatable. Accordingly, a separate volumetric control apparatus, such as balance chamber 50, is not needed. The total volume of fluid pumped is equal to the volume of each stroke multiplied by the number of strokes. UF is controlled via one of the methods discussed above.

Figure 25A:
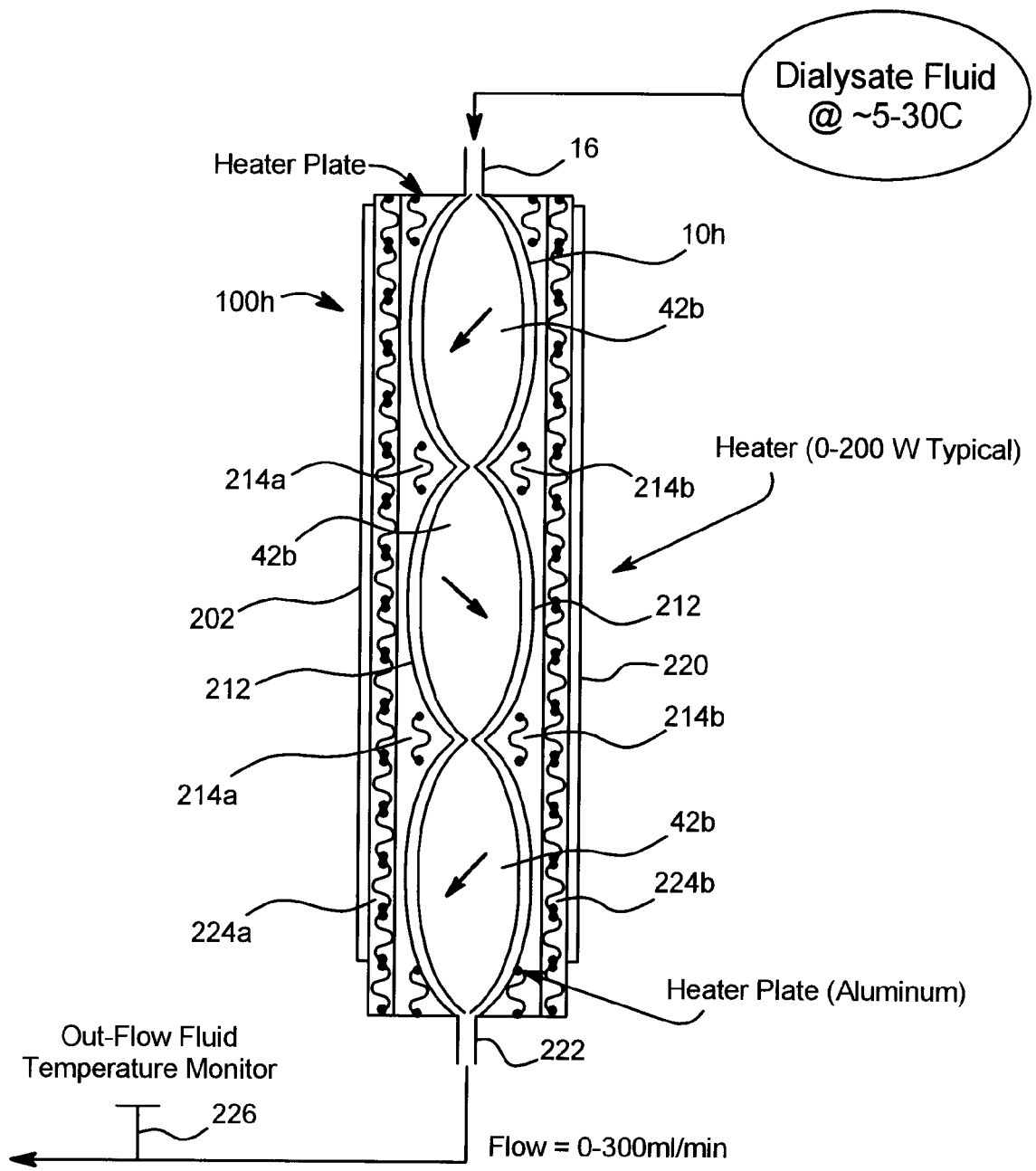
FIG. 25A is a schematic view of a fluid heating pathway formed via compressive clamping and a fluid heater operable with the compressed fluid heating pathway.
Figure 25B:
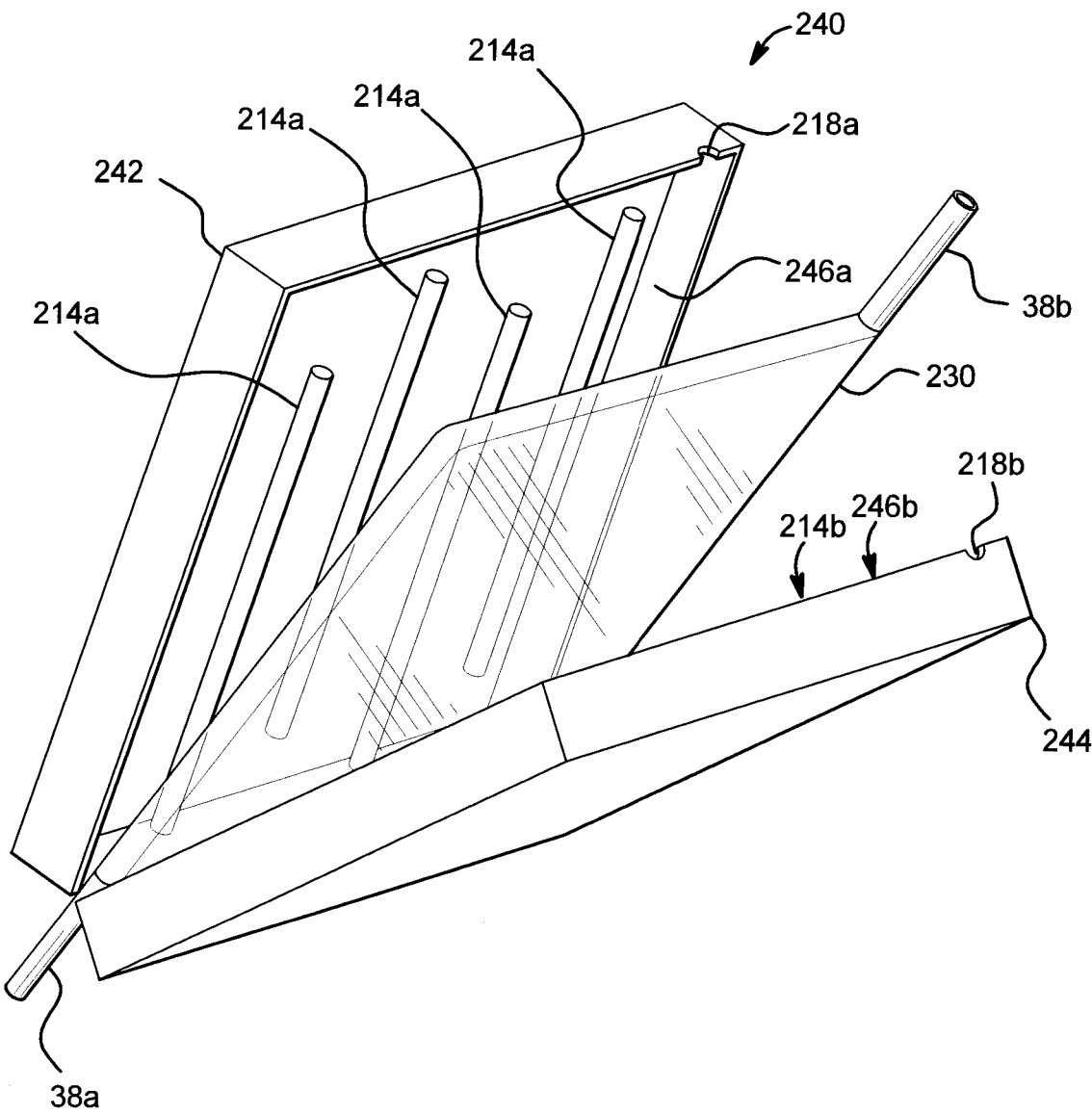
FIG. 25B is a perspective view of a separate heater bag with a fluid heating pathway formed via mechanical compression and a separate heater for the heater bag.
Figure 26A:
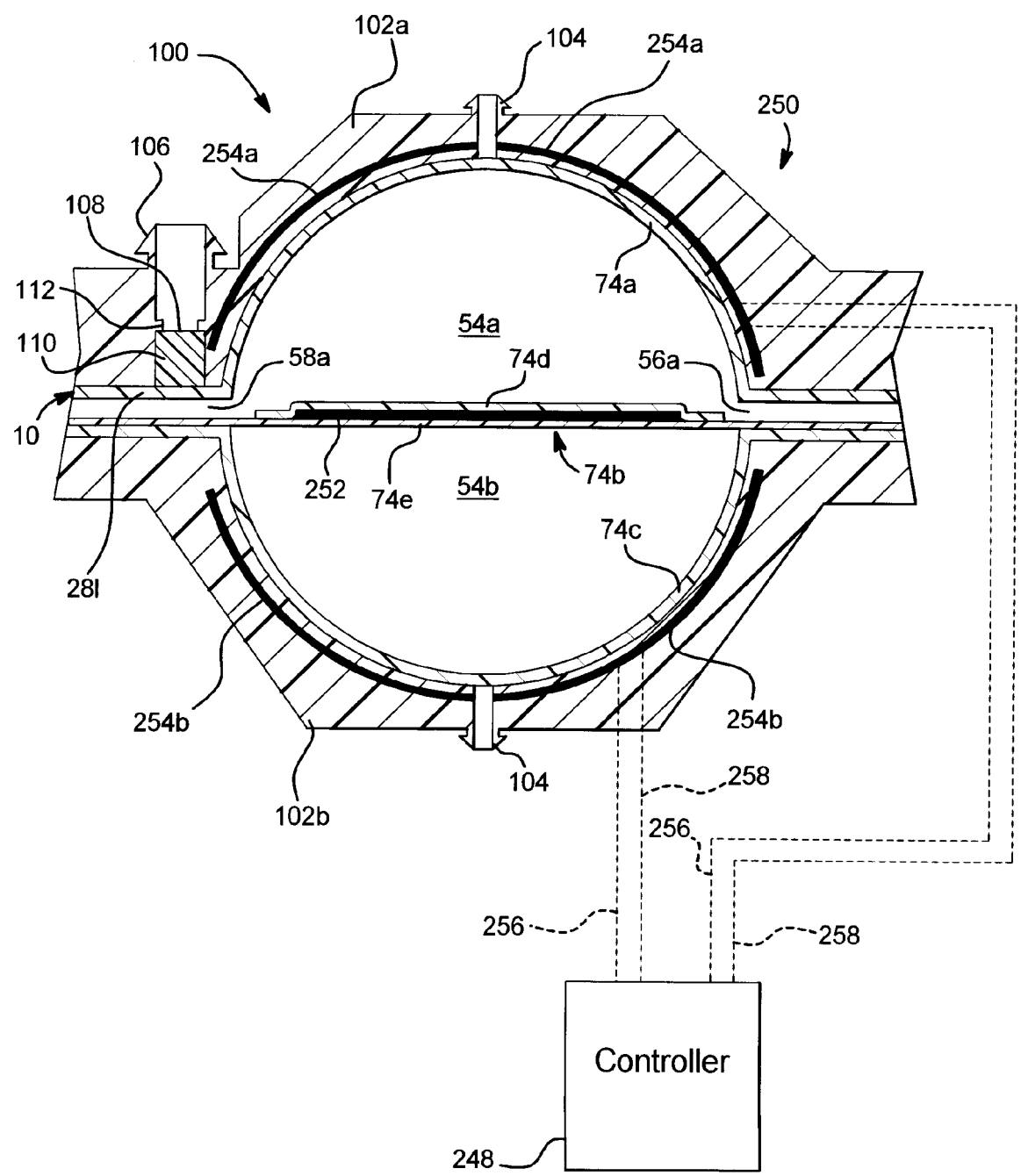
FIGS. 26A and 26B show a balance chamber portion of the disposable cassette formed via mechanical clamping and also illustrate a magnetic field that is used to drive the balance chamber.
Figure 26B:
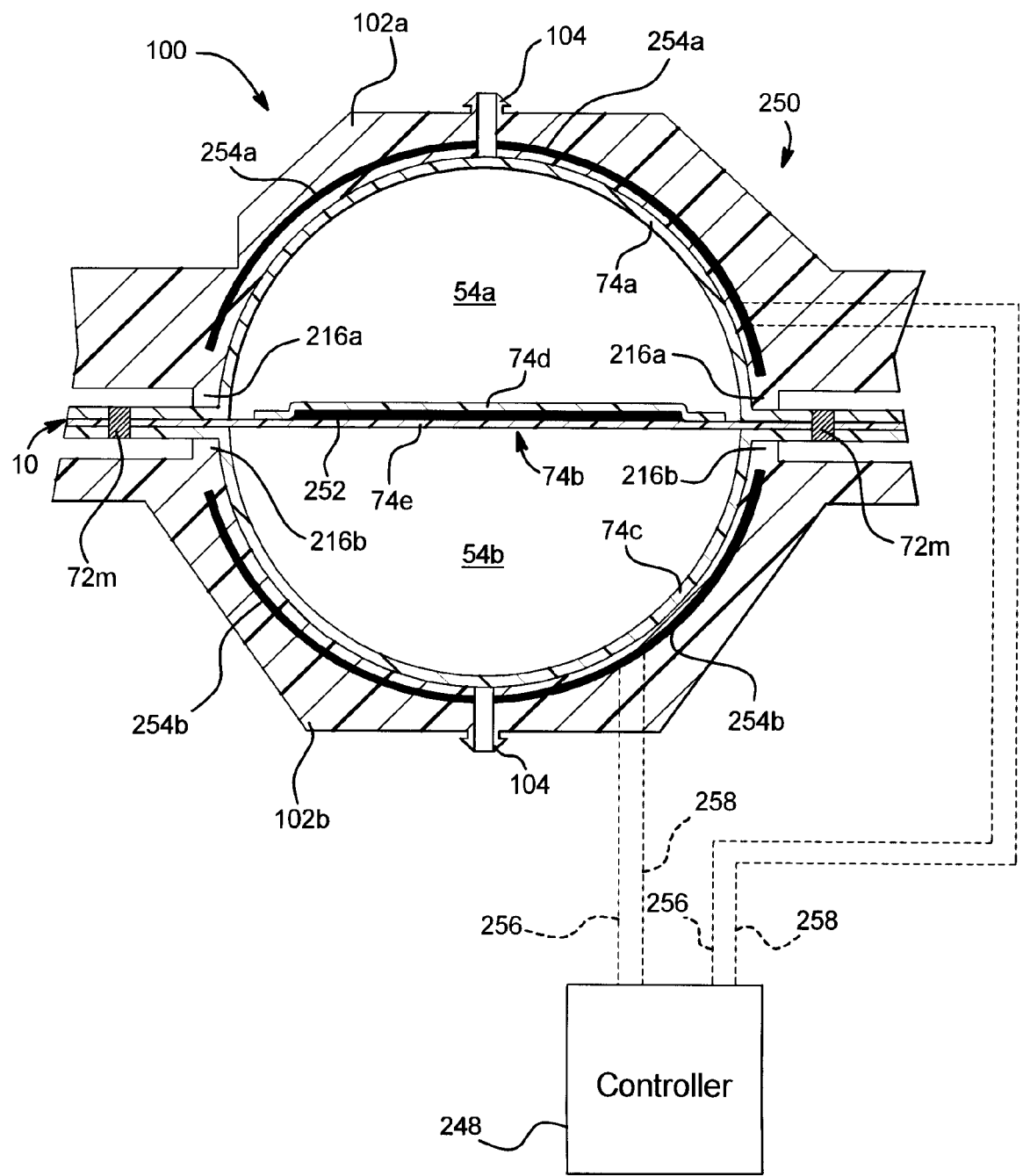

The volumetrically controlled chambers of balance chamber 50 and volumetric pumps 70 are formed in an embodiment via the respective circular seals. In an alternative embodiment, the respective seals are made larger in diameter than needed to achieve the desired volume. Here, a seal between the sheets 74 is created by the pressure of the door pressing against the machine, or a first machine part pressing against a second machine. As shown and discussed in connection with FIGS. 24A and 24B, the machine seal is sized to form the proper diameter sphere to achieve the desired volume. The mechanical clamping seal lessens alignment constraints. The machine to machine seal can be secured manually, e.g., via a lever or lock, clamps, cam-action press-fit, etc. or secured additionally or alternatively formed with the help of pneumatic or electromechanical pressure. FIGS. 25A and 25B discussed below show embodiments for fluid heating pathways formed via mechanical clamping and a heater operable with such fluid heating pathway. FIGS. 26A, 26B and 28 discussed below show embodiments of balance chamber and volumetric pump portions of the flexible sheeting cassette, respectively, formed via mechanical clamping and one embodiment for driving the membranes within the balance and pump chambers.

Figure 10A:
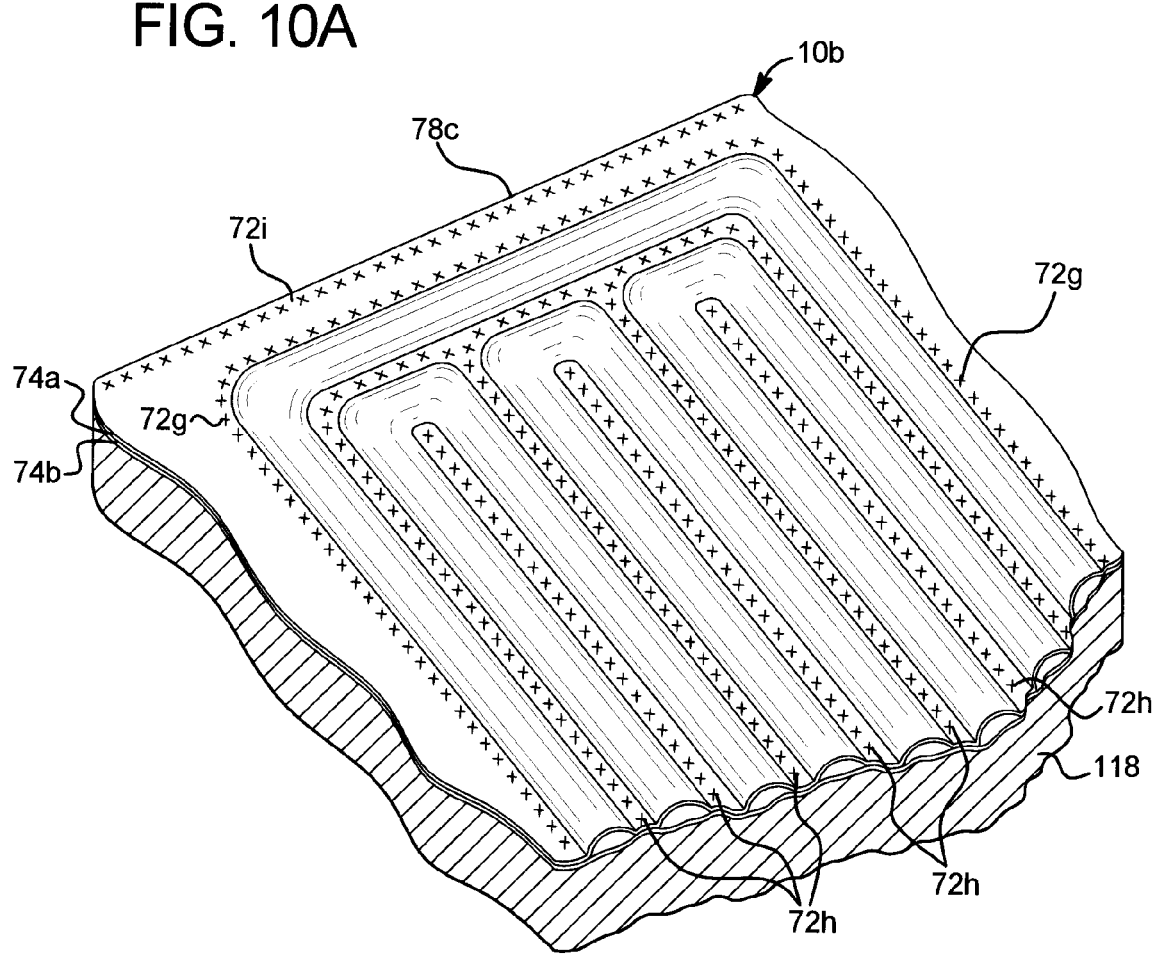
FIG. 10A is a sectioned perspective view of Detail X shown in FIG. 2, which highlights one embodiment for an inline heater portion of the flexible sheeting cassettes.
Figure 10B:
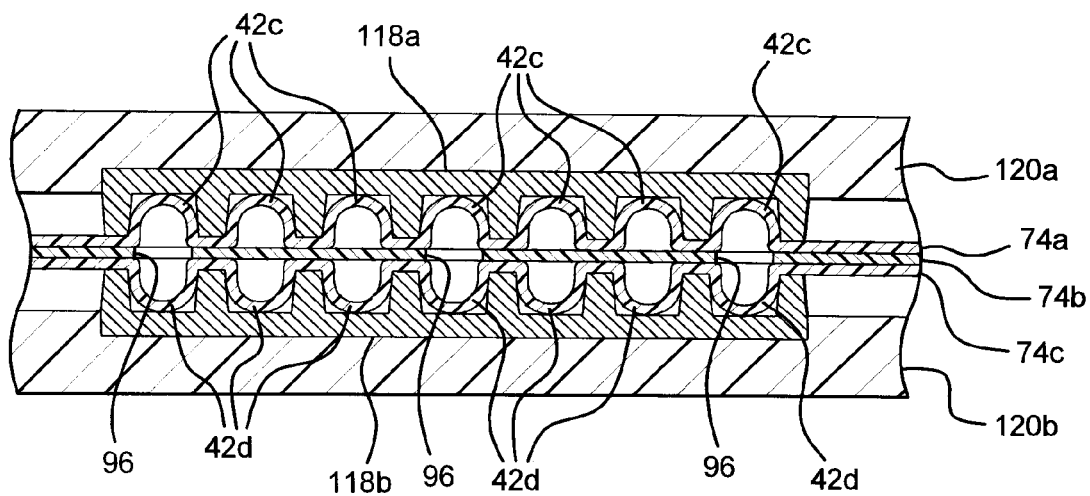
FIG. 10B is a sectioned elevation view of a bi-level inline heater portion in operation with a dialysate fluid heater.

Referring now to FIGS. 10A and 10B, two different embodiments for an integrated heater path for the flexible sheeting cassettes discussed herein are illustrated. FIG. 10A illustrates Detail X of flexible sheeting cassette 10b shown in FIG. 2. FIG. 10B shows an alternative three-layer, dual-sided heater path portion. FIG. 10A shows heater or heater plates 118, while FIG. 10B shows dual heaters or heater plates 118a and 118b. Heaters or heater plates 118 (referring collectively to heater 118 of FIG. 10A and heater plates 118a and 118b of FIG. 10B) can perform any suitable mode of heat transfer, such as electric resistance, inductive, radiant, convective and any combination thereof. As shown in FIG. 10A, heater 118 is continuous beneath fluid heating pathway 42b. In FIG. 10B, heater elements 118a and 118b are localized around the fluid pathways 42c and 42d of the flexible sheeting cassette.

In FIG. 10A, fluid heating pathway 42b is made of first and second sheets 74a and 74b. A semi-circular or other suitable cross-sectional shaped serpentine pathway is formed in sheet 74a via any of the apparatuses and methods discussed above in connection with FIG. 4. Alternatively, both sheets 74a and 74b can form semi-circular halves, which together form a circular whole. If so, heater 118 can be formed or tailored with a semi-circular indented heating pathway to increase surface contact. A continuous outer seal 72g is made around the outside of the loops or serpentine twists of fluid heating pathway 42b. A continuous inner seal 72h is made along the inner curve of pathway 42b. Seals 72g and 72h are made via any of the methods discussed above. Edge seal 72i is also made along edge 78c as seen in FIG. 10A. Alternatively, edge 78c is made via a fold. In operation, dialysate or fluid flows through pathway 42b and is heated via heat energy from heater 118.

In FIG. 10A, flexible sheeting cassette 10b is loaded on top of or is abutted vertically against heater 118. In FIG. 10B, the flexible sheeting cassette is loaded between two insulative housings 120a and 120b. Heater elements 118a are fixed within insulative heater housing 120a. Heater elements 118b are likewise fixed in insulative heater housing 120b. Housings 120a and 120b may be part of the dialysis machine or part of a separate heater.

The fluid heating pathways 42b and 42c of FIG. 10B are formed from three sheets 74a, 74b and 74c. Second sheet 74b serves as a backing to the thermally formed pathways 42c and 42d in sheets 74a to 74c. Sheets 74a and 74c are sealed at once or at different times to middle sheet 74b via any of the sealing methods discussed above. As seen additionally in FIG. 10B, apertures 96 are made in second sheet 74b to enable dialysate to flow from the lower fluid heating pathway 42d of third sheet 74c into the upper fluid heating pathway 42c of sheet 74a or vice versa. FIG. 10B therefore provides an efficient fluid heating apparatus, which in essence doubles the heating capacity for the same surface area versus the flexible sheeting cassette shown in FIG. 10A. Dual pathways such as the pathway 42d could also be made with a separate heater bag 40 of FIGS. 1 and 3.

Figure 11:
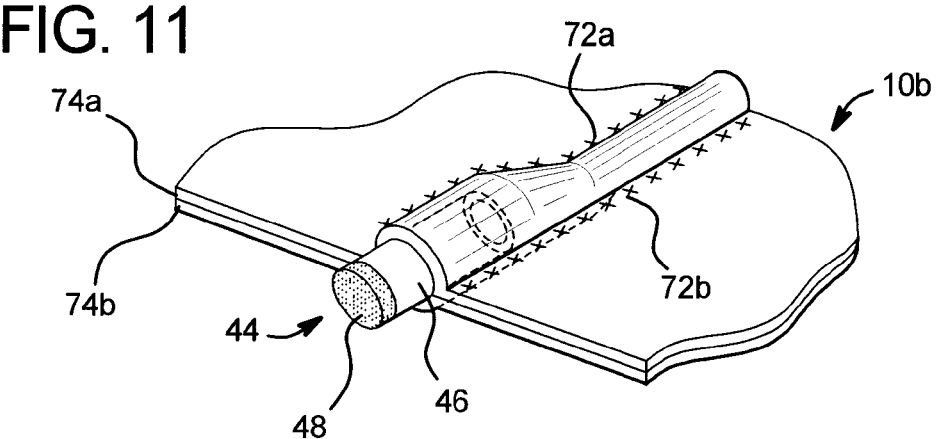
FIG. 11 is a perspective view of Detail XI shown in FIG. 2, illustrating one embodiment of an inline air vent portion for the flexible sheeting cassettes.

Referring now to FIG. 11, one embodiment for mounting vent 44 into one of the flexible sheeting cassettes 10 (referring collectively to flexible sheeting cassettes 10a to 10c) is illustrated. In particular, FIG. 11 shows Detail XI of flexible sheeting cassettes 10b of FIG. 11. Flexible sheeting cassette 10b includes first and second flexible sheets 74a and 74b. Those sheets are sealed around vent 44, which includes a vent body 46 and a filter 48. Filter 48 in one embodiment is a hydrophobic membrane or other type of filter that allows air but not fluid or dialysate to pass through such filter. Vent 44 is fixed to sheets 74a and 74b in much the same manner as connectors 16 and 22 of FIG. 4. To that end, seals 72a and 72b are made on either side of body 46 of filter 48 and/or to body 46 itself. Seals 72a and 72b extend to form a fluid pathway, which can be aided by a thermo-formed shape created or in one or both of sheets 74a and 74b.

In operation, if air is detected in heated dialysate, a valve seat 28h as shown in FIGS. 1 to 3 is opened, allowing the fluid to reach vent 44 and push the air through vent 48. Afterwards, the fluid is pumped to its desired destination. Alternatively, as described above, vent 44 is pointed vertically when its associated cassette is mounted, so that a separate valve actuator and seat are not needed.

Referring now to FIG. 12A, one embodiment for driving fluid through two flow paths using a single peristaltic pump actuator 90 is illustrated. Actuator 90 includes a drive shaft 92 and rollers 94 described above in connection with FIG. 5. Flexible sheeting cassette, e.g., two pump cassette 10c, when loaded, is slid horizontally or vertically over a shaft 122, such that a slot 124 in sheets 74a and 74b slides over a shaft 98 of peristaltic pump actuator 90. Rollers 94 drive fluid through both pumping portions 30a and 30b shown for example in cassette 10c of FIG. 3. Cassette 10c is mounted such that second sheet 74b is abutted against race plates 126a and 126b, which provide a rigid surface against which the flow paths of pumping portions 30a and 30b can be compressed by rollers 94, similar to press-plate 126 of FIG. 5. In the illustrated embodiment, rollers 94 drive fluid in the same direction into and out of pumping portions 30a and 30b. As discussed above, one use for the configuration of FIG. 12 is to provide a single peristaltic pump actuator 90 that drives two pumping portions 30a and 30b, which in turn feed the inlets of balance chambers 50a and 50b with fresh or spent fluid.

Referring now to FIG. 12B, a second embodiment for using a single peristaltic pump actuator 90 to drive fluid through two pumping flow paths is illustrated. Here, peristaltic pumping portions 30a and 30b are configured as semi-circles or half-circles. Shaft 92 spins rollers 94 (actuator 90 can have any suitable number of rollers 94) through a full 260 degrees to drive fluid through both fluid pathways of pumping portions 30a and 30b. A suitable race plate (not illustrated), such as race plate 126 of FIG. 5, is mounted behind flexible sheeting cassette 10b to provide a rigid surface against which rollers 94 can compress the raised pathways 84a and 84b of pumping portions 30a and 30b. Unlike the dual pumping embodiment of FIG. 12A, the dual pumping embodiment of FIG. 12B drives fluid in opposite directions as seen by oppositely disposed inlets 86a/86b and outlets 88a/88b. In both the embodiments of FIGS. 12A and 12B, however, shaft 92 can spin in either of two directions as shown by the arrows in FIG. 12B.

Dialysis machine 100 (referring collectively to each of the machines 100a, 100b, etc.) uses many different sensors, such as pressure sensors, flow sensors, temperature sensors, air bubble detectors, solution identification detectors to check for example for peritonitis, composition and pH, conductivity sensors and ultrasound sensors, e.g., for air or blood detection. Those sensors are used typically to sense some parameter of the dialysate or fluid being pumped through one of the flexible sheeting cassettes 10.

Figure 13:
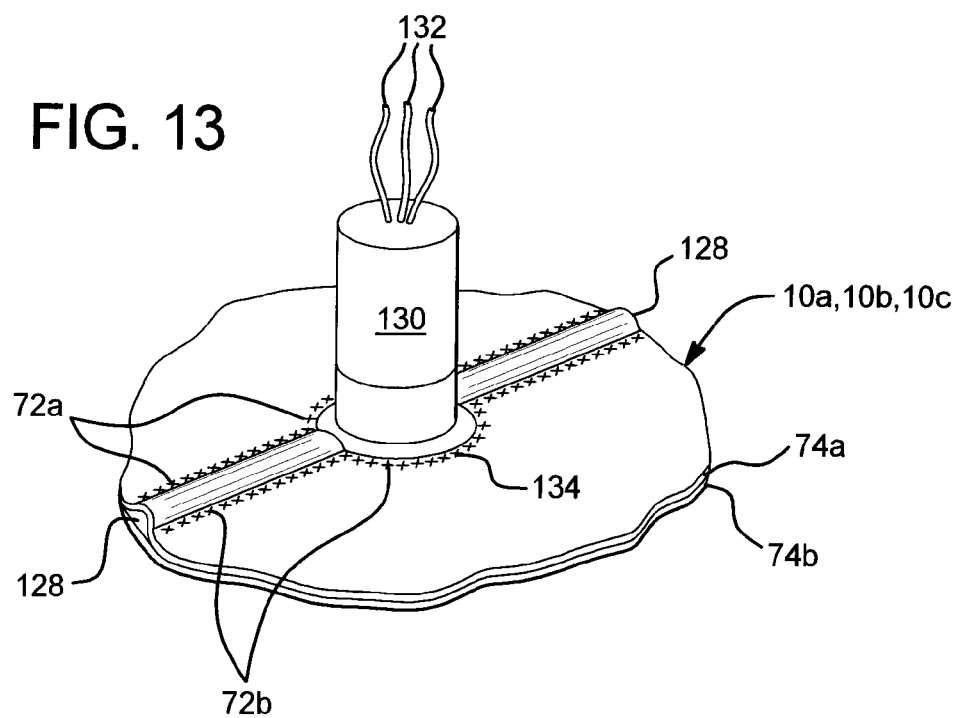
FIG. 13 is a sectioned perspective view illustrating one embodiment of the flexible sheeting cassettes employing a pressure (or other parameter) sensing area in combination with a pressure (or other parameter) sensor.

Referring now to FIG. 13, one embodiment for operating a sensor 130 with any one of the flexible sheeting cassettes 10a to 10c is illustrated. Sensor 130 can be any of the above-described types of sensors and includes leads or wires 132 that lead to a control unit or controller of dialysis machine 100. Sensor 130 senses a parameter of dialysate or medical fluid (including blood) flowing through a flow path 128. Cassette 10 (any cassette herein) is mounted such that a sensing area 134 is aligned with sensor 130. Sensing area 134 is an expanded flow path area defined by seals 72a and 72b, which slows down the flow of fluid, and can increase sensing time and accuracy. Seals 72a and 72b are made via any of the methods and embodiments discussed above. Sensing area 134 is shaped and sized to conform to the head of sensor 130.

Figure 14:
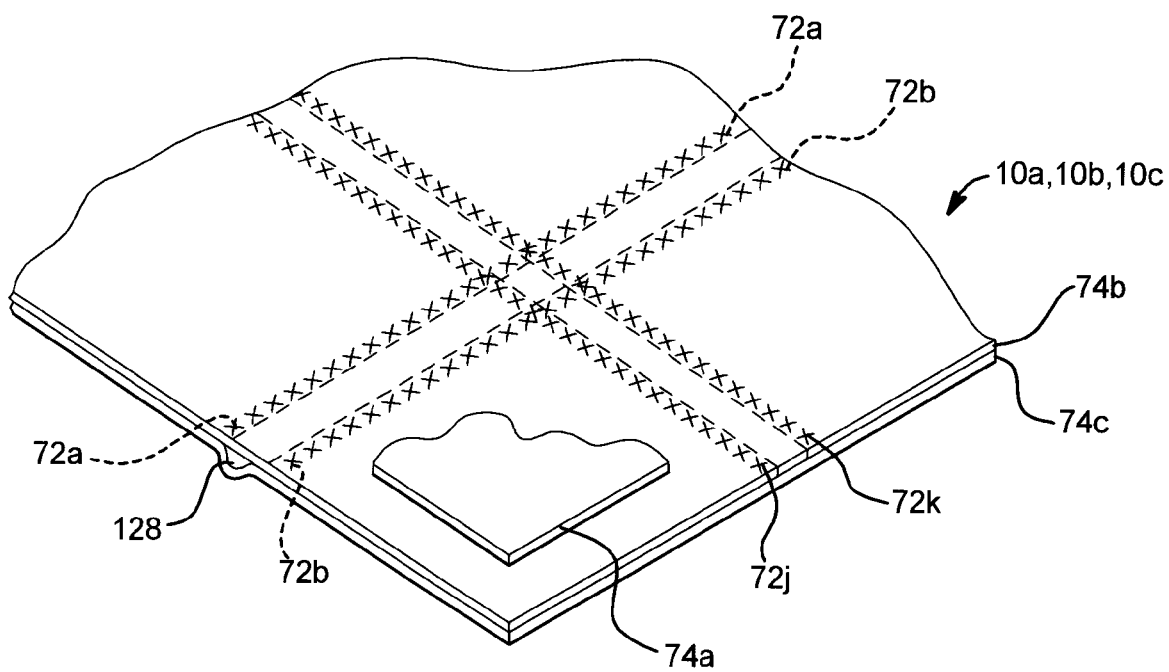
FIG. 14 is a sectioned perspective view of the flexible sheeting cassettes showing one method and resulting apparatus for selectively sealing three flexible sheets together.

Referring now to FIG. 14, one embodiment for making different seals between three sheets 74 of material is illustrated. In FIG. 14, sheets 74b and 74c are illustrated. Sheet 74a (not illustrated) is sealed to the top of sheet 74b. A flow path 128 is made between sheets 74b and 74c. As illustrated, a thermo-formed indent or raised portion is made in sheet 74c, which is then sealed to sheet 74b via any of the different methods discussed above for seals 72a and 72b. Next, a printable adhesive is deposited on the upper surface of sheet 74b along seal lines 72j and 72k. One suitable printable adhesive is cyclohexanone, e.g., for polyvinyl chloride ("PVC") sheeting, or a polyester elastomer for other types of sheeting. Next, sheet or ply 74a is placed as desired onto the top of sheet 74b. Radio frequency ("RF"), ultraviolet ("UV") energy or heat is then applied to adhesive seal lines 72j and 72k to activate the printed adhesive along the applied pattern, sealing sheet 74a to 74b. In this manner, the three sheets 72a to 72c can form any desired seal pattern (same or different) between sheets 74a and 74b and between sheets 74b and 74c.

Figure 15:
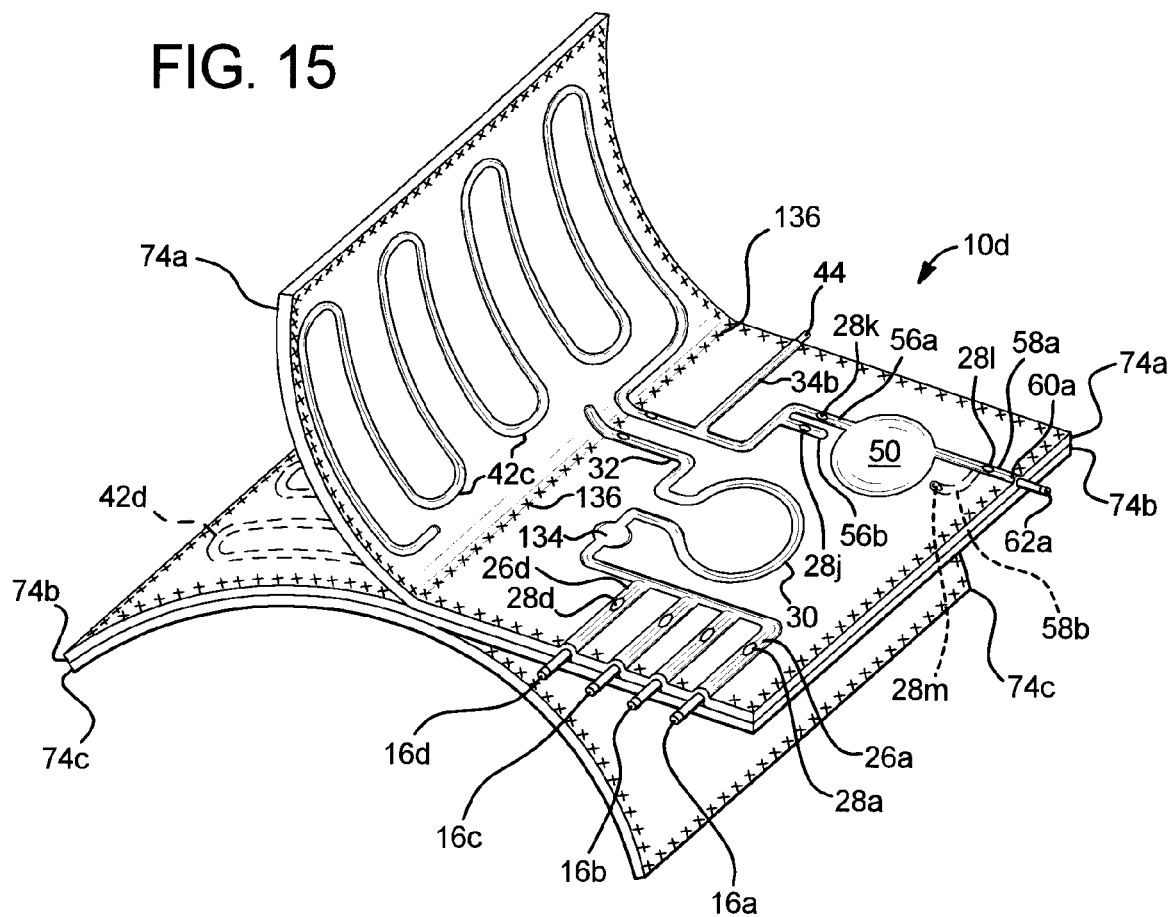
FIG. 15 is a perspective view of an example flexible sheeting cassette showing a second method and resulting apparatus for selectively sealing three flexible sheets together.

Referring now to FIG. 15, another method for selectively sealing three sheets 74a to 74c of flexible material to form a flexible sheeting cassette is illustrated. A sealed seam 136 extends along one length of the cassette 10d, for example at or near the middle of the other length of the cassette. Seam 136 enables the cassette to be maneuvered and folded to make selectable seams in the three different sheets 74a to 74c. This method applies to any flexible sheeting cassettes discussed above. For purposes of illustration, flexible sheeting cassette 10d of FIG. 15 includes the single peristaltic pump 30 and balance chamber 50 of FIG. 1 with an incorporated fluid heating pathway 42b of FIG. 2. As shown above, many features of the flexible sheeting cassette require only two sheets 74a and 74b. Other components such as balance chamber 50 require three sheets 74a to 74c. It is therefore contemplated to provide a cassette 10d, which includes three sheets or plies 74 in areas requiring three sheets and only two sheets 74a and 74b in other areas of cassette 10d requiring only two sheets. In cassette 10d, three sheets 74a to 74c are used alternatively over the whole cassette 10d. Again, sheets 74a to 74c can be separate or formed by folding a single piece of material one or more times.

The left side of cassette 10d is used to make the three layer dual sided heating flow paths 42c and 42d discussed above in connection with FIG. 10B. As illustrated, one of the outwardly facing flow paths, such as flow path 42d is formed first by sealing sheets 74b and 74c together. Next, sheet 74a is sealed to the combination of sheets 74b and 74c. In an embodiment, sheet 74a is sealed to the combination of sheets 74b and 74c via the printable adhesive described above. In another embodiment, enough energy is applied to the outside of sheet 74a and 74c to chemically bond or melt sheets 74a and 74b together. Further alternatively, sheets 74a to 74c can be secured to form fluid heating pathways 42c and 42d simultaneously. Middle sheet 74b defines apertures 96 as discussed above that reside between fluid heating pathways 42c and 42d.

The right side of cassette 10d is used to form balance chamber 50, peristaltic pump 30, pressure sensing area 134, fluid flow pathways 26a to 26d and other flow paths associated with the above-listed components. Here, flexible sheets 74a and 74b are sealed together first, after which sheet 74c is sealed to sheet 74b, e.g., to complete balance chamber 50. Although not illustrated, additional flow paths can be formed between sheets 74b and 74c, with one or more apertures 96 allowing fluid to flow from flow paths or flow apparatuses formed via sheet 74a and 74b and ones formed between sheets 74b and 74c. Sheet 74c can be sealed to sheet 74b via the printable adhesive or alternatively or additionally by applying energy through all three sheets 74a to 74c.

As illustrated, pump output pathway 32 extends from peristaltic pumping portion 30 across seam 136, through mating apertures defined in sheets 74a and 74b, into the lower fluid heating pathway 42d, through its serpentine path, back through another set of mating apertures in sheets 74a and 74b, into and through upper fluid heating pathway 42c, before extending into balance chamber 50 and out to patient connector 62a.

Figure 16:
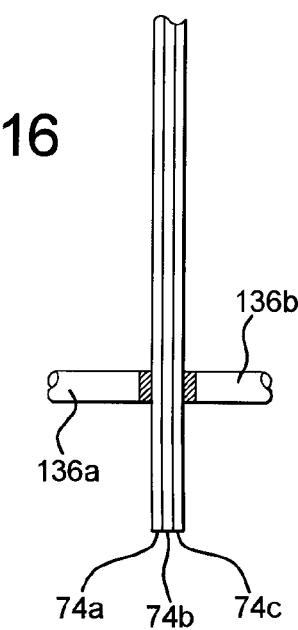
FIG. 16 is an elevation view of a portion of a flexible sheeting cassette illustrating a third method for selectively sealing three flexible sheets together.

Referring now to FIG. 16, another method for sealing three sheets 74a to 74c together is illustrated. In FIG. 16, layers 74a to 74c are sealed using die sealing apparatuses 136a and 136b using machinery built for example by KIEFEL Extrusion GmbH, Cornelius-Heyl-Str.49, 67547 Worms/Germany. Apparatuses 136a and 136b apply heat to sheets 74a to 74c in a predefined die pattern. The die pattern includes areas in which all three sheets 74a to 74c are sealed together and other areas in which only two of sheets 74a and 74b or 74b and 74c are sealed together.

In a conductive die sealing machine, each die apparatus 136a and 136b is controlled to output a desired amount of heat in direct contact with outer sheets 74a and 74c. For example, die apparatus 136a can be set to output more heat than die apparatus 136b. Using this conductive type of heating, if it is desired to seal middle layer 74b only to sheet 74a or 74c, apparatus 136a or 136b on the non-sealing side of either sheet 74a or sheet 74b is set to deliver a lesser amount of heat to prevent sealing between that sheet and middle sheet 74b. The heat of the opposing die apparatus 136a or 136b contacting the sheet 74a or 74c that is to form a seal with sheet 74b is set to output a higher amount of heat, enough to melt the two sheets and seal the sheets in a desired pattern. The temperatures of hot and cold die apparatuses 136a and 136b are set to create a temperature profile that is higher than the melting temperature of middle layer 136b on the side to be sealed and lower on the opposing side of sheet 136b to prevent this side of the middle layer from melting. To this end, it may be that one of die apparatuses is de-energized completely. The die machine is accordingly capable of controlling the heat outputs of each apparatus 136a and 136b independently to heat the different sheets 74a to 74c to the desired temperatures.

In another embodiment, the die sealing machine is of a radio frequency ("RF") type. Here, one of the apparatuses 136a and 136b is positive and the other is negative and direct or indirect contact with sheets 74a and 74c. RF-type sealing is especially well-suited for sealing PVC, e.g., PVC tubing and PVC sheeting, although it can be used to seal other kinds of tubing and sheeting materials listed herein. RF-type sealing can be used in the embodiment of FIG. 15, for example, to seal the three sheets in multiple steps.

Figure 17:
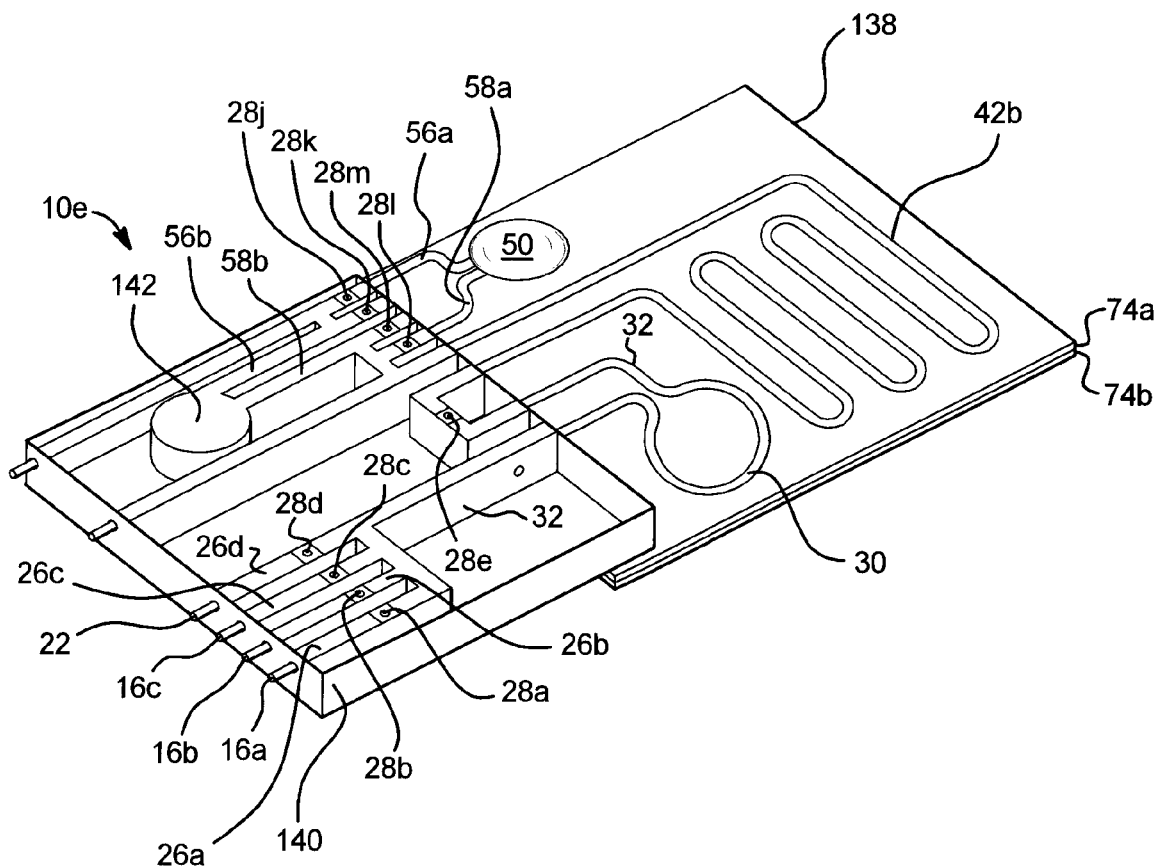
FIG. 17 is a perspective view of one embodiment for an overall cassette which combines path forming flexible sheets with a rigid cassette portion.
Figure 18:
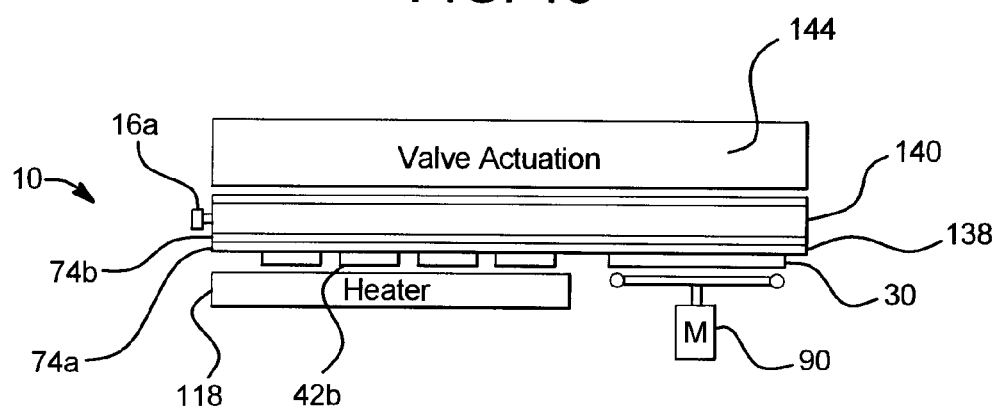
FIG. 18 illustrates one embodiment for configuring a cassette having a flexible sheeting portion and a rigid portion with corresponding valve actuation, pump actuation and heater.

Referring now to FIGS. 17, 18, 19A and 19B, in an alternative embodiment, a cassette 10e includes a flexible portion 138 and a rigid portion 140. Flexible portion 138 includes first sheet 74a and second sheet 74b. Peristaltic pumping portion 30 and inline fluid heating pathway 42b are formed via sheets 74a and 74b in flexible portion 138 in any manner described above. With cassette 10e, however, balance chamber 50 is formed using two sheets 74a and 74b instead of the three sheet version described above. Here, balance chamber 50 is formed partially via a rigid chamber 142 formed in rigid portion 140. As seen in FIG. 18, flexible portion 138 is folded under or otherwise attached to the underside of rigid portion 140. When this occurs, the flexible membrane portion of balance chamber 50 aligns with and is thereafter sealed to rigid chamber 142 of rigid portion 140.

FIG. 18 also shows heater 118 operating with heating pathway 42b and peristaltic pump actuator 90 operating with peristaltic pumping portion 30. Valve actuators, such as actuators 106 discussed above, are provided in valve actuation unit 144. Valve actuation unit 144 resides on the opposing side of cassette 10e from heater 118 and pump actuator 90. In the illustrated embodiment valve actuation unit 144 can be part of a door that presses valve actuators 106, heater 118 and pump actuator 90 in place against the appropriate positions of cassette 10e.

Valve seats, such as seats 28a to 28d, are provided as part of rigid portion 140 of cassette 10e. Rigid flow paths, such as flow paths 26a to 26d, 32, 58a and 58b, communicate with pumping portion 30, balance chamber 50, their associated flow paths and fluid heating pathway 42b of flexible portion 138 via apertures, such as apertures 96 provided in one or more sheets 74b and 74a with the rigid fluid pathways.

Regarding balance chamber 50, flow paths 56a and 58a flow from the flexible portion of balance chamber 50 of flexible portion 138 to rigid pathways defined by rigid portion 140. Valve seats 28j to 28m are located in rigid portion 140. Further, pathways 56b and 58b leading to rigid chamber 142 are also provided in rigid portion 140.

Referring now to FIGS. 19A and 19B, a balance chamber 50 constructed from rigid chamber 142 of rigid portion 140 and two flexible sheets 74a and 74b of flexible portion 138 of cassette 10e is illustrated. While balance chamber 50 of FIGS. 19A and 19B is shown in connection with cassette 10e having rigid portion 140 and flexible portion 138, it is expressly contemplated to provide the balance chamber 50 of FIGS. 19A and 19B with a flexible sheeting cassette in which having a sole rigid portion 142. That is, rigid chamber 142 can be provided independently or separately and is not required to part of a larger rigid portion 140.

As illustrated, sheet 74a butts against a rigid backing member 146. Rigid backing member 146 can be provided with cassette 10d or is alternatively part of dialysis machine 100d operating with cassette 10d. Backing plate 146 constrains lower balance chamber compartment 54b to expand into the cavity formed by rigid chamber 142 when lower balance chamber compartment 54d is filled. Valve seats 28k and 28m are shown figuratively in cooperation with rigid chamber 142. Likewise, valve seats 28j and 28l are shown figuratively in cooperation with sheets 74a and 74b. For purposes of illustration, valve seats are shown with an "X" when in a closed fluid state and without an "X" when in an open or fluid flow state.

In FIG. 19A, the valve actuators operating with valve seats 28j and 28m cause the seats to be closed, while the valve actuators operating with valve seats 28k and 28l cause those seats to be open. In this valve state configuration, upper balance chamber compartment 54a fills with a volume of fluid 116, while lower balance chamber compartment 54b expels a like volume of fluid to a desired destination. In FIG. 19B, the valve actuators operating with valve seats 28k and 28l cause those seats to be closed, while the actuators operating with valve seats 28j and 28m cause those seats to be open. Here, lower balance chamber compartment 54b fills with fluid 116, while a like volume of fluid is dispensed from upper balance chamber compartment 54a, past valve seat 28m, to a desired destination.

The rigid chamber version of balance chamber 50 can be provided singly in a cassette, for example as shown in FIGS. 1 and 17 with cassettes 28a and 28d. Alternatively, two or more rigid chamber versions of balance chamber 50 are provided in a cassette, such as discussed in connection with cassette 10c of FIG. 3. Under normal matched flow circumstances, fresh fluid enters one of the compartments 54a or 54b dispensing spent fluid from the other compartment, and vice versa. Rigid chamber balance chamber 50 can alternatively be used for UF only, in which case spent fluid is delivered to both compartments 54a and 54b.

Referring now to FIGS. 20A to 20D, an alternative embodiment for balance chamber 50 employing the flexible sheet 74a to 74c is illustrated. Balance chamber 50 in FIGS. 20A to 20D incorporates tubes 156a and 156b as balance chamber inlet and tubes 158a and 158b as balance chamber outlets. Tubes 156a, 156b, 158a and 158b can be made of any suitable medical grade material, such as PVC, non-DEHP PVC, polybutadiene ("PB"), ethylene vinyl acetate ("EVA"), polypropylene ("PP") blend, polyethylene ("PE") blend, Kraton blend and polyolefin blends. The tubes are sealed in place along seals 72l. Upper and lower seals 72e and 72f discussed above in connection with FIGS. 6 and 7 are made to form upper balance chamber compartment 54a and lower balance chamber compartment 54b. Inlet tube 156a and outlet tube 158a communicate fluidly with upper balance chamber compartment 54a, while inlet tube 156b and outlet tube 158b communicate fluidly with lower balance chamber compartment 54b.

Inner ends 160 of balance chamber inlet tubes 156a and 156b and balance chamber outlet tubes 158a and 158b are configured to be aligned with the circular chambers formed by seals 72e and 72f, so as to allow first and third sheets 74a and 74c to be pulled apart against respective inner walls of the balance chamber formerly members located inside the dialysis machine, such as chamber walls 102a and 102b shown in FIG. 7. Middle sheet 74b is sealed to the bottom of tubes 156a and 158a so that fluid entering from tube 156a can flow only into upper compartment 54a. Middle sheet 74b is sealed around the top of inner ends 160 of tubes 156b and 158b, so that fluid entering sheet and tube type balance chamber 50 through 156b can enter only into bottom compartment 54b of balance chamber 50. Otherwise, middle sheet 74b is free to move back and forth within outer sheets 74a and 74c when balance chamber 50 is in operation.

Figure 20A:
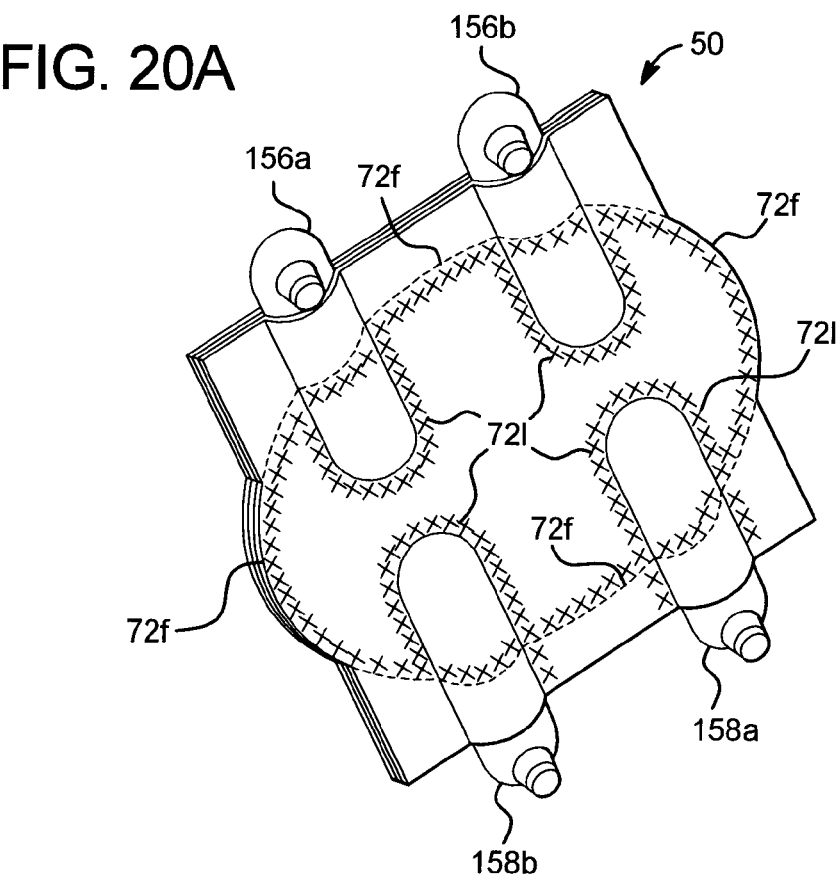
FIGS. 20A to 20D are perspective views in various stages of manufacture of a further alternative embodiment of a balance chamber portion produced via multiple flexible sheets.
Figure 20B:
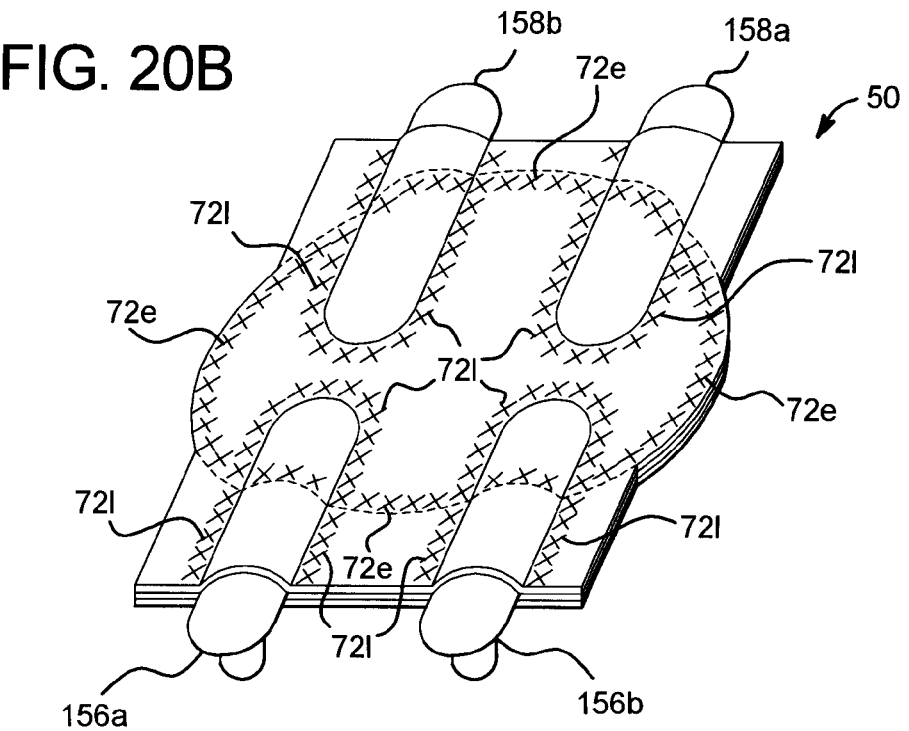
Figure 20C:
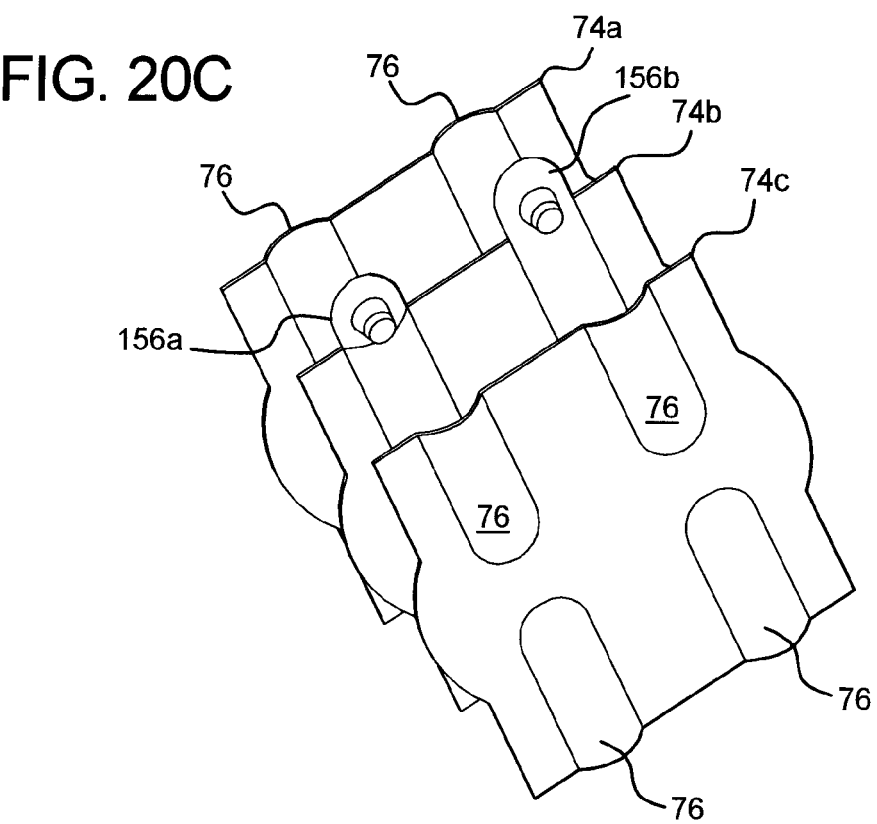
Figure 20D:
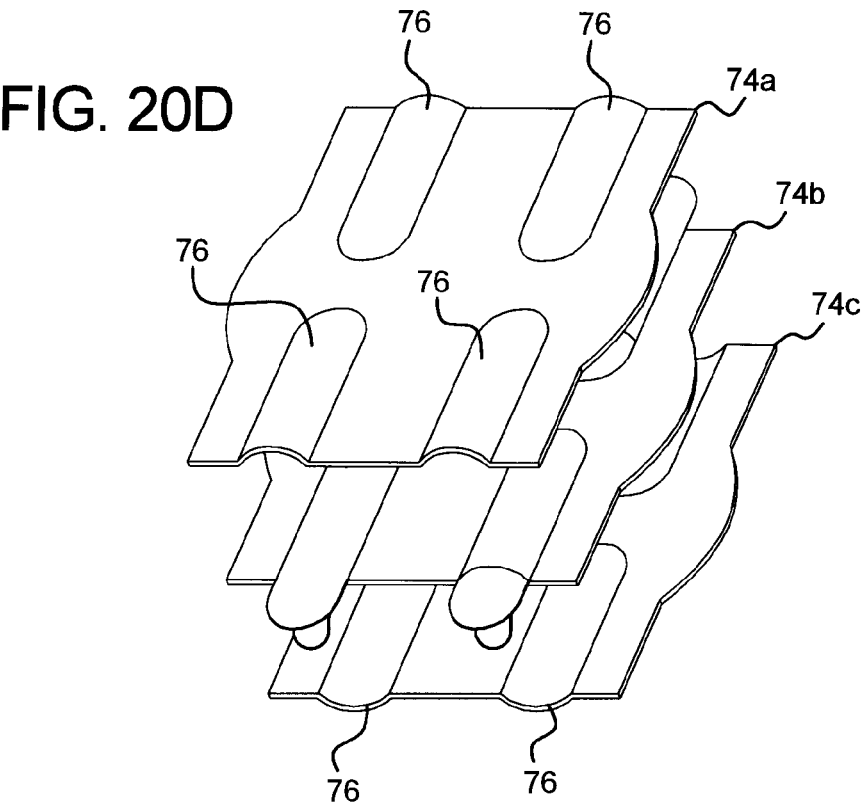

FIGS. 20C and 20D illustrate that sheets 74a to 74c have semicircular bends 76. Bends 76 can be preformed or at least partially preformed, e.g., via thermoforming. Alternatively, bends 76 are formed during the process of sealing sheets 74a to 74c about tubes 156 and 158. Bends 76 are made outwardly in outer sheets 74a and 74c. Bends 76 in middle sheet 74b alternate direction as needed. Depending on which side is being welded, seal 72l may weld two sheets 74a/74b or 74b/74c or one sheet 74a or 74b to tubes 156a or 156b.

In the illustrated embodiment, sheet and tube type balance chamber 50 is provided as a separate apparatus that can be connected fluidly to another part of the disposable unit or the dialysis system. To that end, tubes 156a to 158b can be as long as needed to be connected to the other part of the dialysate circuit. In an alternative embodiment, two or more balance chambers 50 having the configuration of FIGS. 20A to 20D are formed via sheets 74a to 74c and two or more sets of tubes 156a to 158b. Further alternatively, one or more of the balance chambers 50 of FIGS. 20A to 20D is provided in a cassette such as cassettes 10a to 10d, which contain most if not all of the components of the dialysate circuit, notwithstanding the bags, patient connection and associated tubing.

Tubes 156a to 158b can have or include valve seats, such as valve seats 28j to 28l described above in connection with the balance chamber 50 of FIG. 1. Alternatively, automated pinch or tubing clamps are used to clamp a portion of tubes 156a to 158b without needing a modified valve seat area. Balance chamber 50 of FIGS. 20A to 20D can be used in any of the cassettes described herein employing one or more balance chamber.

Figure 21D:
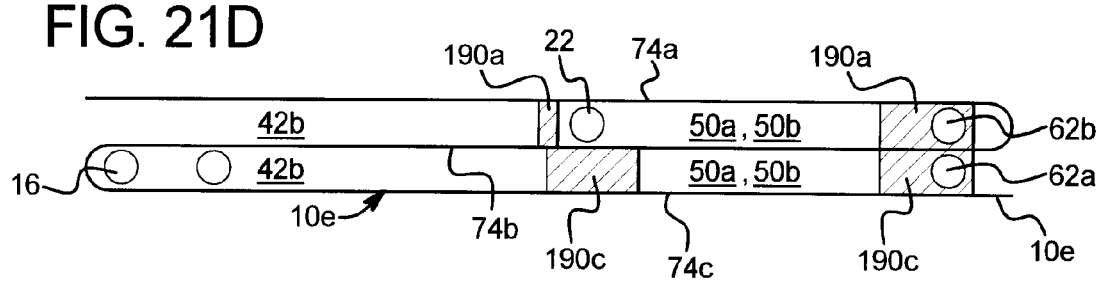

Referring now to FIGS. 21A to 21G, an alternative flexible sheeting cassette 10e is shown in operation with a hemodialysis machine 100e, which in one preferred embodiment is a home hemodialysis ("HHD") machine. Alternatively, cassette 10e can be used with any of the dialysis therapies discussed herein. As discussed in the parent application, hemodialysis typically takes place in a clinic or center, in which the dialysate is made online using a water source and concentrates. In a home setting, a similar type of online dialysate generation unit is also used typically. These units are large and require the dialysis machine to be connected to a source of water. In the embodiment illustrated in FIGS. 21A to 21G and in the parent application, an alternative system is shown, which uses dialysate supplied from one or more supply bag, and which can provide convective clearance in addition to diffusive clearance. Alternatively, the blood disposable is combined with the dialysate disposable. In FIGS. 21B and 21F, a separate blood cassette 150 is provided.

FIGS. 21A and 21C to 21E illustrate flexible sheeting cassette 10e. Cassette 21e differs from the above described cassettes in a number of ways. One difference is that separate peristaltic pumping tubes 148 and 154 are used instead of the flexible sheeting cassette pumping portion 30 shown and described above for example in connection with FIGS. 1, 3 and 5. A second difference is that the manifolding of the different supply and drain bags is done via tubing external to the flexible sheets 74a to 74c of cassette 10e. In FIG. 21A, the peristaltic pump actuators operating with dialysate line 148 and UF line 154 drive fluid to the inlets of balance chambers 50a and 50b. In an HHD therapy fluid exits the valved outlets of balance chambers 50a and 50b to either a dialyzer or the drain as described above. As before, balance chambers 50 operate as intermediate metering devices that meter a like volume of fluid to the drain and the dialyzer. Any of the methods for controlling ultrafiltration described above can be used with flexible sheeting cassette 10e. For example, a number of strokes of balance chamber 50 can be dedicated UF strokes, in which spent fluid is pumped into both halves of balance chambers 50a and 50b. Alternatively, a separate UF balance chamber can be provided.

Figure 21C:
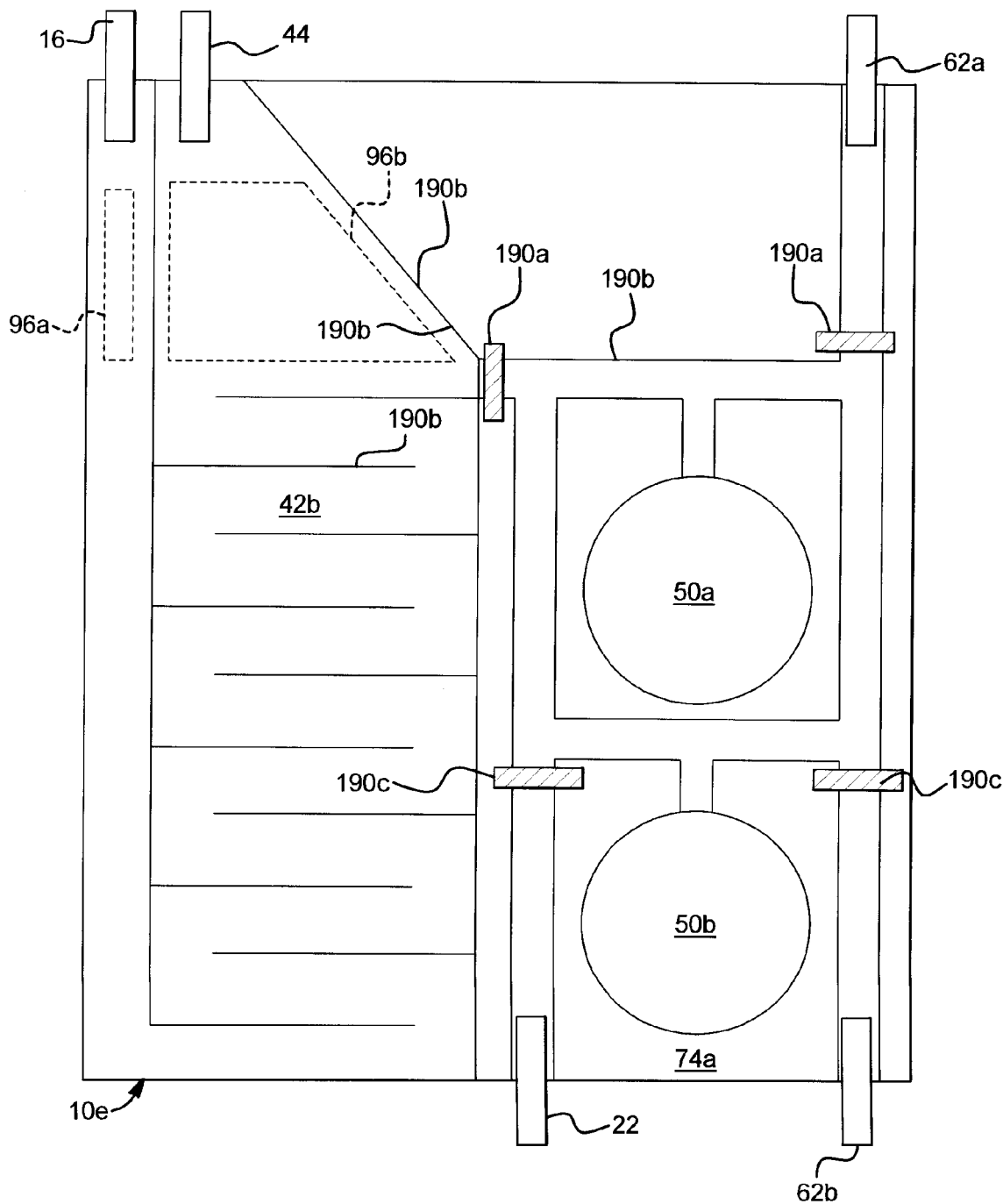
Figure 21E:
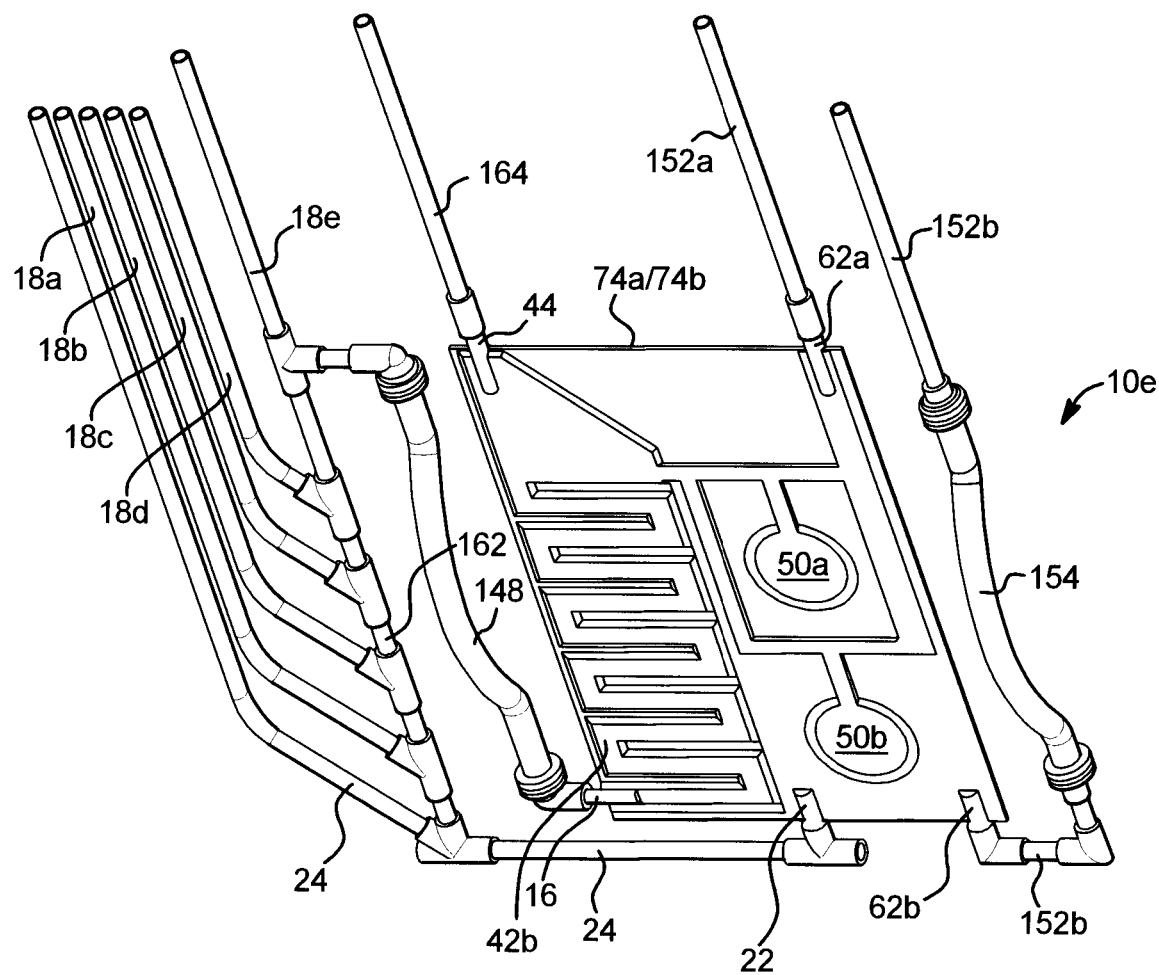

As seen in FIGS. 21A and 21E, fresh dialysate is pumped from one of the supply bags through a respective supply line 18a to 18e, into a manifold 162 and a dialysate pumping tube 148, which operates with a peristaltic dialysate pump actuator. The peristaltic dialysate pump pumps fresh dialysate through inlet connector 16, through integrated inline fluid heating pathway 42b, and into one of the balance chambers 50a or 50b. Any air egressing from the heated solution is allowed to vent through vent 44. In an embodiment, cassette 10e is mounted vertically as shown in FIGS. 21A and 21E, such that air automatically rises to the top of cassette 10e and is released through air vent 44 and vent line 164 (FIG. 21E). This reduces the number valve actuators and seats as discussed above in connection with cassettes 10a to 10c. That is, any air is purged automatically without having to shutdown the normal operation of the machine.

The pumping of fresh dialysate into an inlet compartment of one of balance chambers 50a and 50b causes a like amount of spent fluid already residing in that balance chamber to be pumped via drainline 24 to drain. At the same time, the UF pump actuator operating with UF pump line 154 pumps spent fluid from the dialyzer, through from-patient line 152b, into the inlet compartment of the other of balance chambers 50a and 50b. Such action causes a like volume of fresh fluid to be pumped through patient connector 62a and to-patient line 152a to the dialyzer.

As seen in FIG. 21A, a tubing organizer 168 is provided to hold supply lines 18a to 18e, drainline 24, vent line 164, to-dialyzer line 152a and from-dialyzer line 152b in an organized manner and enable cassette 10e and associated tubes to be mounted readily. FIG. 21A also shows darkened areas 188 cooperating with manifold 162. Darkened areas 188 indicate portions of the associated tubes that are pinched closed to selectively allow fresh dialysate to be pulled from a desired supply bag 12 and spent dialysate to be pumped to drain bag 14 or one of the supply bags 12 being used as a drain bag.

Referring now to FIGS. 21C ad 21D, a number of additional features of flexible sheeting cassette 10e are illustrated. The schematic side view of FIG. 21D illustrates that sheets 74a, 74b and 74c are formed from a single sheet of material, which is folded twice to produce the three layers 74 (referring collectively to layers 24a to 24c). This allows the number of outer edge seams or seals to be reduced and also helps with the alignment of separate layers 74a to 74c. It should be appreciated that any of the flexible sheeting cassettes described herein can be formed using a single folded sheet, two sheets with one fold or three separate sheets, etc.

FIGS. 21C and 21D also show first weld areas 190a in which only first sheet 74a is welded to or otherwise fixed to sheet 74b. Weld areas 190b are also shown in which all three sheets 74a to 74c are welded or adhered together. FIG. 21C also shows third areas 190c in which only the second layer 74b is welded to or otherwise fixed to third layer 74c. This selective welding enables cassette 10e to be made efficiently. Welding of three sheets does not have to be made in areas in which only two sheets need to be welded together. However, the three sheets can be welded or otherwise attached in areas in which it is required to do so. In general, two layer welds or glue joints 190a and 190c are required when flow in one layer is desired but not in another layer. In an alternative embodiment, three layer welds 190b (except for periphery three layer welds and three layer welds for inlet and outlet ports) are eliminated and replaced with the compression seals described below in connection with FIGS. 24A, 24B, 25A, 25B, 26A, 26B and 28.

In FIG. 21C, selective welding occurs in areas associated with balance chambers 50a and 50b. FIG. 6 provides further information on how three sheeted balance chambers 50 can be welded together. Serpentine pathway 42b is formed from a three sheet weld. This enables fluid heating pathway 42b to extend spatially efficiently between sheets 74a and 74b and sheets 74b and 74c.

FIGS. 21C and 21D illustrate that the fluid travels between different layers or sheeting pairs using apertures 96 made in desired places in middle sheet 74b. Fluid for example enters single supply connector 16 in a first pathway between sheets 74b and 74c. An aperture 96a enables the fluid to travel into a portion of fluid heating pathway 42b located between sheets 74a and 74b, in which it is heated a first time. Next, the fluid moves through an aperture 96b into a second portion of fluid heating pathway 42b located between sheets 74b and 74c. Any air egressing the heater solution is vented through the top of cassette 10e via event 44. Next, the heated fluid enters the balance chamber area, which uses all three sheets 74a to 74c in one embodiment. The fresh fluid leaves through a balance chamber compartment located between sheet 74b and 74c to the dialyzer through two patient connector 62a. Spent fluid returns from the dialyzer to cassette 10e via from patient connector 62b into a balance chamber compartment located between sheets 74a and 74b. The spent fluid is sent to drain via drain connector 22 located between sheets 74a and 74b.

Referring now to FIGS. 21B and 21F, one embodiment of a blood cassette 150 used with HD, HHD and HF is illustrated. Blood cassette 150 is also mounted vertically as illustrated in one embodiment. Cassette 150 includes a rigid portion 170 having a rigid housing 172 and a flexible membrane 174 made of any of the materials discussed above attached to housing 172. Rigid portion 170 is made from a suitable material, such as polyvinyl chloride ("PVC"), acrylic, ABS, polycarbonate, polyolefin blends. Housing 172 includes or defines a from-patient port 176, a to-patient port 178, a saline port 180, a vent 44, a to-dialyzer port 182 and a from-dialyzer port 184. As seen FIGS. 21B and 21F ports, such as ports 178 and 180, port 184 and vent 44 can be formed in different relative locations along housing 172.

FIG. 21B illustrates valve seats 28x to 28z operating with the from-patient line, to-patient line and the saline line, respectively. A peristaltic pump actuator operates with blood pump line 166 to pump blood from the patient, to cassette 150 to the dialyzer, back to cassette 150 and then back to the patient. Fluid received from the dialyzer enters an air separation chamber 192 before being returned to the patient. Blood 186 collects at the bottom of air separation chamber, while any air in the blood raises to the top of air separation chamber 192. Air separation chamber 192 can further include a vent 44, such as a hydrophobic membrane, which allows air to be purged from cassette 150.

The operation of blood cassette 150 of FIG. 21F is similar to the operation described in connection with FIG. 21B. Here, however, valve seat 28y operates with to-dialyzer line connected to to-dialzyer port 182. Valve seat 28x controls the fluid entering cassette 150 from the patient as shown in FIG. 21B. Valve seat 21z controls the flow of saline into the cassette. Air separation chamber 192 operates as before, in which air at the top of chamber 192 can exit cassette 150 via vent 44. Blood at the bottom of air separation chamber 192 flows to the patient through to-patient port 178. FIG. 21F further illustrates that a flexible sheet 174 is welded or adhered to rigid portion 172 of housing 170. The flexible sheet 174 enables a valve actuator to press valve seats 28x to 28z to open/close a respective fluid flow path. As further illustrated in FIG. 21F, blood cassette 150 includes or provides sensing areas 194a and 194b to sense a parameter of the blood, such as arterial pressure, venous pressure or blood temperature.

Cassette 150 illustrates components associated with a blood cassette used with HD, HHD, HF, HDF and any combination thereof as described in the parent application. As seen, the blood cassette can be provided as a separate cassette 150 installed separately from a dialysate cassette 10a to 10b. Alternatively, the components of the blood cassette are integrated with any one of dialysate cassettes 10 disclosed herein.

Referring now to FIG. 21G, a top view of hemodialysis machine 100e illustrates one embodiment for mounting cassette 10e, the various supply bags 12 and drain bag 14. Cassette 10e can be placed on a angle relative to the top of machine 100e, so as to create at least a slight vertical component to the mounting of cassette 10e for venting purposes discussed above. Supply bags 12 and drain bag 14 are supported by the top of machine 100e and are connected fluidly to cassette 10e before or after the cassette is mounted to machine 100e. Machine 100e includes the user interface 196, which enables the patient or caregiver to begin, control and monitor therapy. User interface 196 can use a touch screen overlay operable with a touch screen controller and/or membrane switches as desired.

Figure 22A:
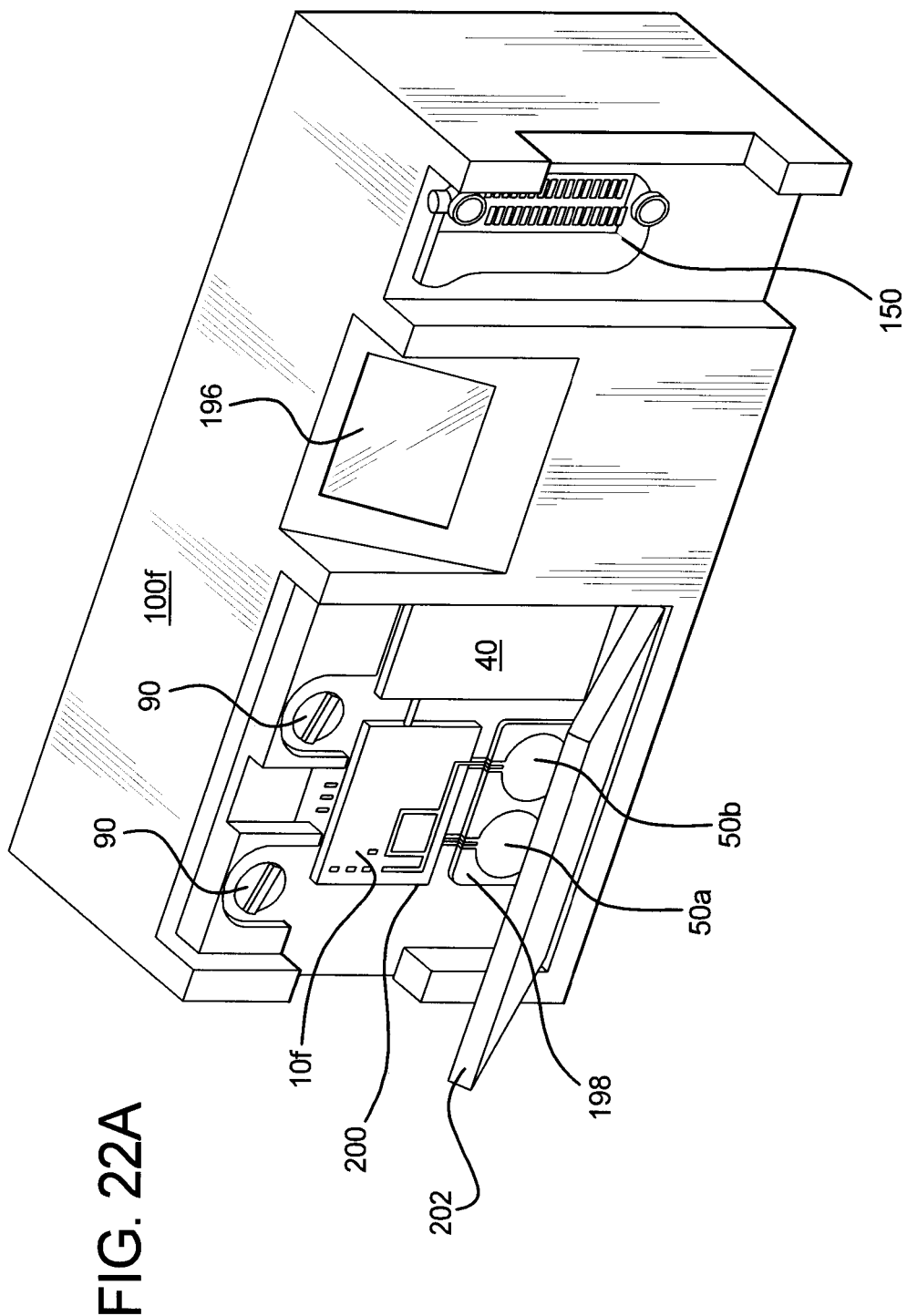
FIGS. 22A to 22D are perspective views of a further alternative system employing a flexible sheeting dialysate cassette in combination with a separate blood-side cassette.

Referring now to FIGS. 22A to 22D, a further alternative system 100f employing an alternative flexible sheeting cassette 10f is illustrated. System 100f is well-suited to perform hemodialysis, such as home hemodialysis. Here, system 100f also uses a second blood cassette, which can be similar to or the same as blood cassette 150 described above. FIG. 22A illustrates one embodiment for loading the cassettes 10f and 150 into machine 100f. Here, the dialysate components are located on one side of user interface 196, while the blood components are located on the other side of user interface 196. This configuration makes loading the cassettes relatively easy for the user and also allows the valve and pump actuators and heater located within machine 100e to be mounted efficiently, reducing the overall size of machine 100f.

In machine 100f, cassette 10f is positioned vertically, which is advantageous for air purging purposes described above. Machine 100f includes two peristaltic pump actuators 90, one of which drives fluid through a dialysate tube, while the other drives fluid through a UF tube, similar to the arrangement described above for cassette 10e. A separate heater bag 40 described above in connection with FIG. 1 extends to the right from a rigid housing portion 200 of cassette 100f. Rigid housing portion 200 as shown in more detail below defines flow paths and associated valve seats. Accordingly, the valve actuators of machine 100f are located behind rigid cassette portion 200 of cassette 10f. A plate heater or other type of heater is located behind heater bag 40. A dual balance chamber flexible membrane component 198 of cassette 10f resides beneath rigid portion 200. As discussed herein, peristaltic pump actuators 90 drive fresh and spent fluid alternatively through the inlet compartments of balance chambers 50a and 50b. A hinged door 202 enables cassette 10f, including its rigid portion 200, balance chamber component 198 and heater bag 40 to be inserted and removed readily from machine 100f.

Figure 22B:
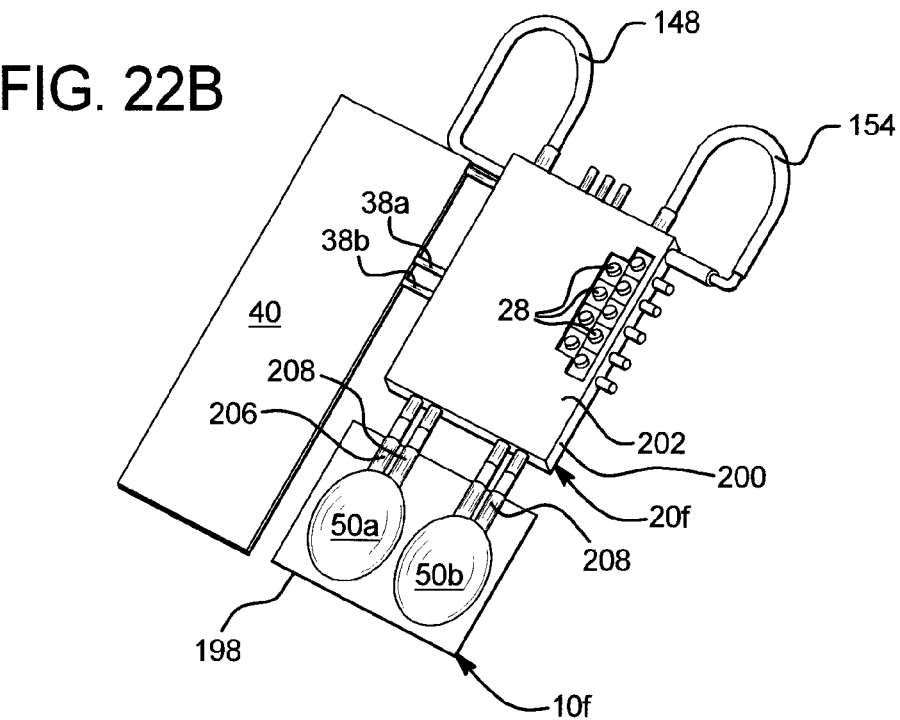

Referring now to FIG. 22B, a more detailed view of cassette 10f is illustrated. As discussed, cassette 10f includes a rigid portion 200 connected fluidly to a separate heater bag 40 and a balance chamber unit 198. Cassette 10f therefore differs from cassette 10e in that the heating and balance chamber functions are done via the flexible sheeting membranes, while valve actuation is performed using a rigid member 200 in combination with a flexible sheet 202. Valve actuators, e.g., spring-loaded closed, pneumatically operated open actuators, operate with valve seats 28 to open and close selected flow paths as desired. Cassette 10f also includes separate peristaltic pumping tubes 148 and 154 described above in connection with cassette 10e. Heater bag 40 includes a serpentine heating pathway (not illustrated) and communicates with rigid member 200 via to-and from-heater lines 38a and 38b, respectively. Balance chamber unit 198 also communicates with rigid valve member 200 via port connectors and tubes as illustrated.

Figure 22C:
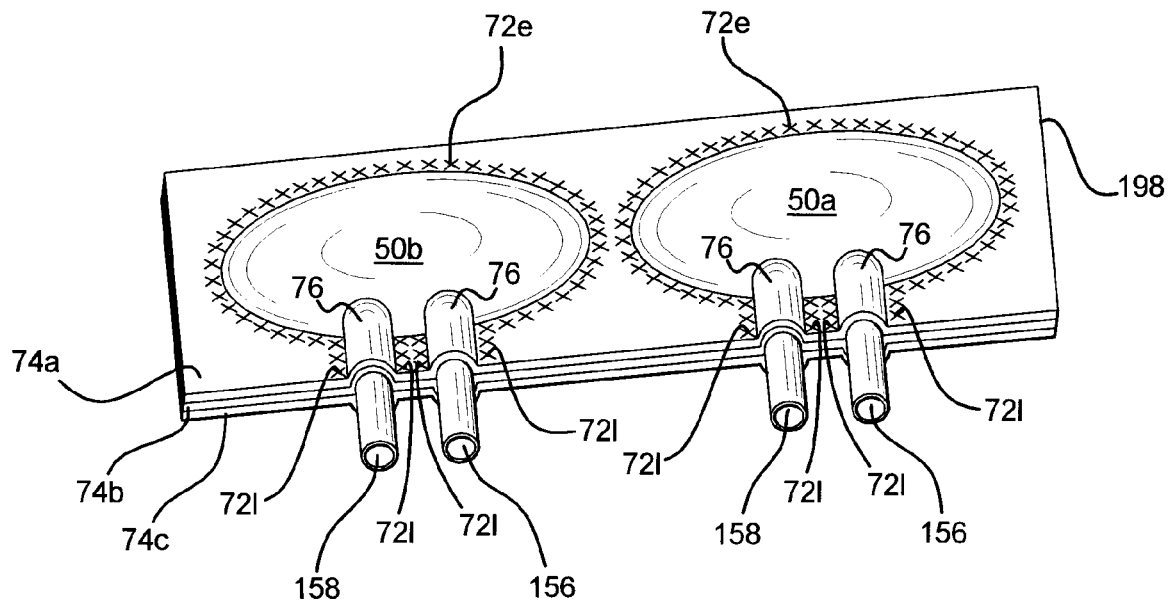
Figure 22D:
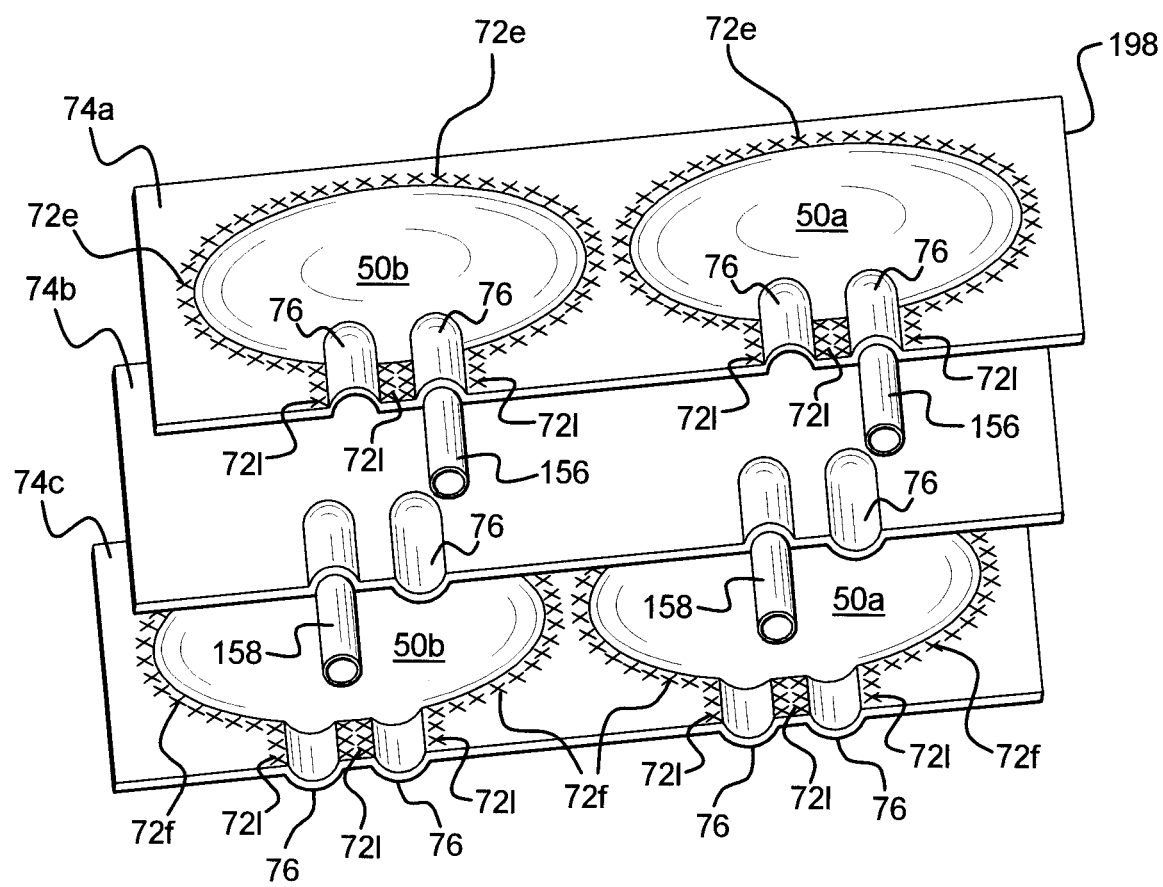

Balance chamber unit 198 is illustrated in more detail in FIGS. 22C and 22D. Balance chamber unit 198 is similar to the flexible sheeting balance chamber 50 described above in connection with FIGS. 20A to 20D. Here, unit 198 provides two balance chambers 50a and 50b, which are made of flexible sheets 74a to 74c, fresh fluid tubes 156 and spend fluid tubes 158. As seen best in FIG. 22D, each compartment of balance chambers 50a and 50b communicates with only one of fresh tube 156 or spent 158. Fresh tube 156 communicates with a first balance chamber compartment located between sheets 74a and 74b, while spent tube 158 communicates fluidly with a second balance chamber compartment located between sheets 74b and 74c. Balance chambers 50a and 50b each include seals 72e, 72f and 72l as described above in connection with FIGS. 20A to 20D.

FIG. 22D illustrates that sheets 74a to 74c have semicircular bends 76, similar to that of balance chamber 50 of FIGS. 20A to 20D. Bends 76 can be preformed or at least partially preformed, e.g., via thermoforming. Alternatively, bends 76 are formed during the process of sealing sheets 74a to 74c about tubes 156 and 158. Bends 76 are made outwardly in outer sheets 74a and 74c. Bends 76 in middle sheet 74b alternate direction for each of balance chambers 50a and 50b. As seen, each tube 156 and 158 has a single sheet 74a or 74c welded on one side and two sheets 74a or 74c in combination with middle sheet 74b welded on its other side. In one embodiment, tubes 156 and 158 are welded to middle sheet 74b first. Outer sheets 74a and 74c are then welded to middle sheet 74b and the exposed parts of tubes 156 and 158.

In operation, fresh fluid enters and leaves through tube 156. Spent fluid enters and leaves through tube 158. That is, there is not a separate inlet and outlet tube for each balance chamber compartment is the case with balance chamber 50 of FIGS. 20A to 20D, which has two fresh tubes 156a and 156b and two spent tubes 158a and 158b. Rather, the same tube acts as the fresh or spent fluid inlet and fluid outlet for its compartment. Valves and flow paths are configured within rigid member 200 to direct the flow into or out of balance chambers 50a and 50b as desired.

Fresh fluid entering the fresh balance chamber compartment between sheets 74a and 74b through tube 156 causes middle sheet 74b to dispel a like amount of spent fluid from spent compartment between sheets 74b and 74c through spent tube 158. While this occurs in one of balance chambers 50a and 50b, spent fluid enters spent compartment between sheets 74b and 74c of the other balance chamber, flexing middle sheet 74b to dispel a like amount of fresh fluid from fresh compartment between sheets 74a and 74b through fresh tube 156. The sequence is then reversed. In this manner, an at least semicontinuous flow of fluid is sent to the patient or dialyzer and to drain.

Figure 23:
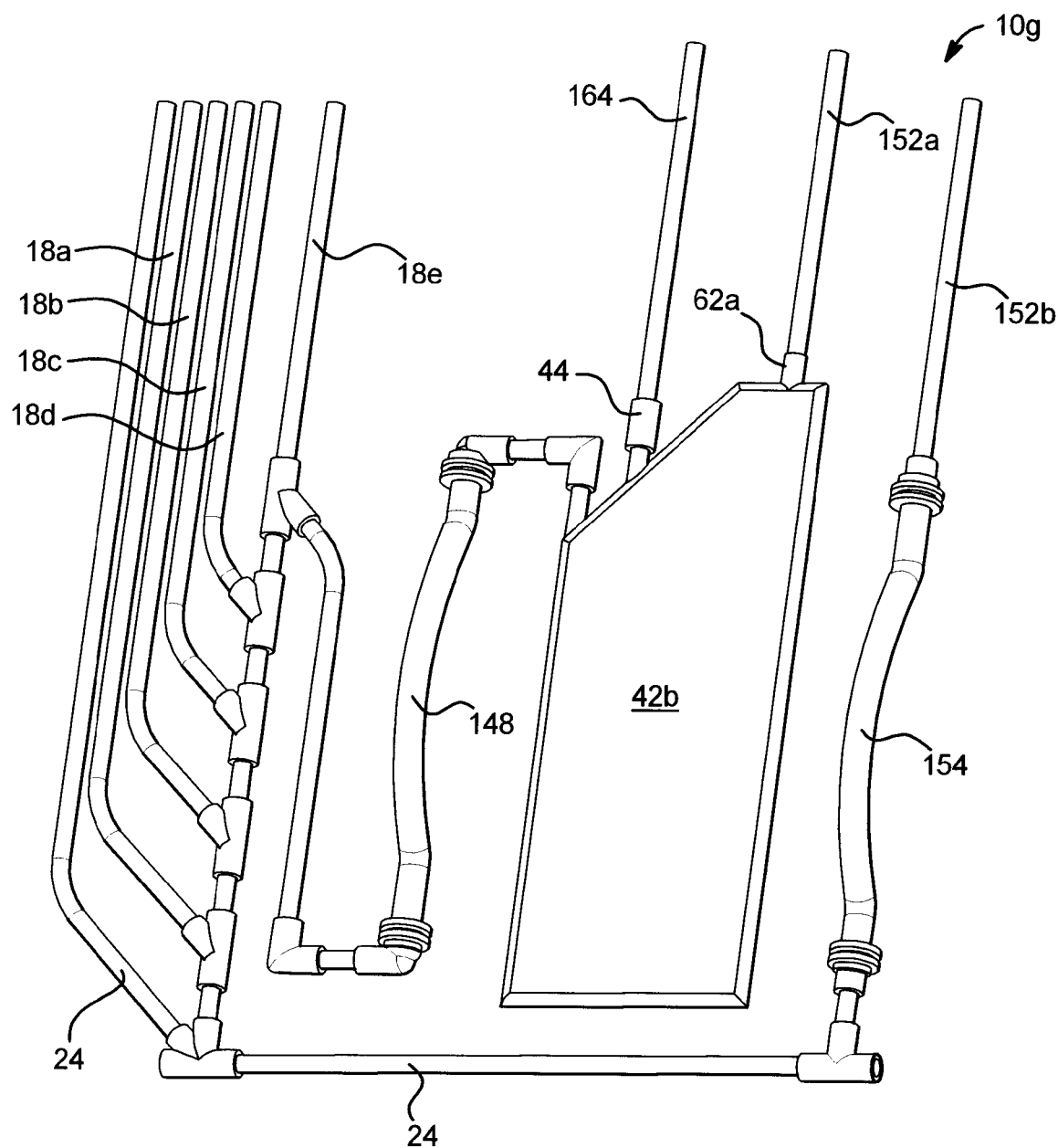
FIG. 23 is a perspective view of yet another alternative medical fluid cassette for use with a system employing a gravimetric volume control methodology.

Referring now to FIG. 23, a further alternative cassette is illustrated by cassette 10g. Cassette 10g is a simplified version of cassette 10e. Cassette 10g includes supply lines 18a to 18e, drainline 24, dialysate pump tube 148, return pump tube 154, inline fluid heating pathway 42b, vent 44, vent line 164, to-patient connector 62a, to-dialyzer line 152a, and from-dialyzer line 152b. The primary difference between cassette 10g and cassette 10e is that balance chambers 50a and 50b used with cassette 10e are not used with cassette 10g. That is, volumetric control of fluid is not performed using matched flow equalizers or balance chambers 50a and 50b with flexible sheeting cassette 10g. Instead, another method is used, such as via gravimetric or weight control of fluid delivered and removed from the patient or via a flow management system ("FMS") used with a HomeChoice® dialysis machine marketed by the assignee of the present application. The body of sheeting cassette 10g can include valve seat and flow paths as needed to direct flow in a desired manner. Alternatively, flow can be controlled by clamping and unclamping the tubes connected to cassette 10g, in which case cassette 10g serves primarily as a fluid heating pathway. The flow paths, valve seats and fluid heating pathway 42b can be provided via two sheets 74a and 74b or three sheets 74a to 74c as has described herein or can have a rigid component, such as rigid frame.

Figure 24A:
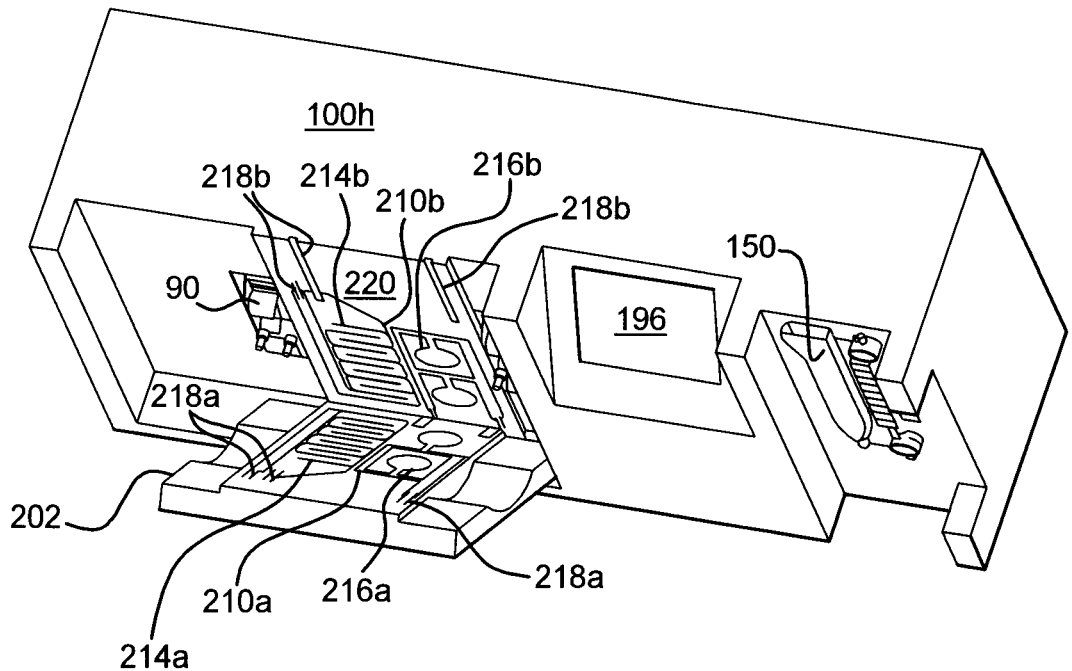
FIGS. 24A and 24B are perspective views of an alternative flexible sheeting cassette system in which the machine includes clamping members that compressively form pump, flow and fluid heating paths.
Figure 24B:
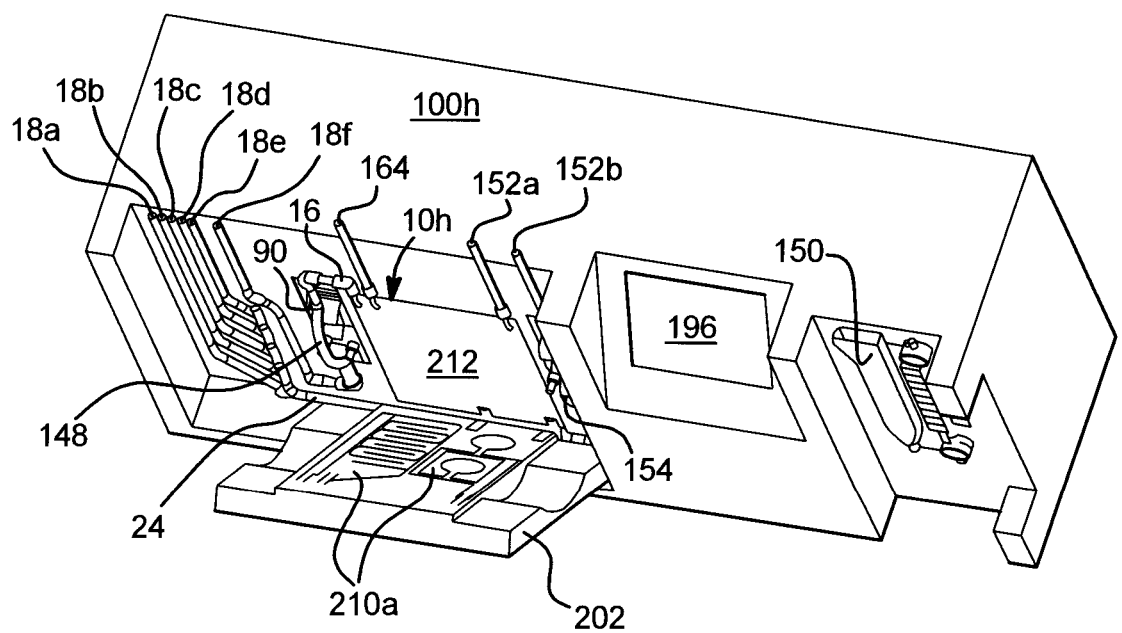

Referring now to FIGS. 24A and 24B, a further alternative system 100h employing flexible membrane cassette 10h is illustrated. System 100h is well-suited to perform hemodialysis, such as home hemodialysis. System 100h uses a blood cassette, such as cassette 150. FIG. 24A shows system 100h without cassette 10h loaded. FIG. 24B shows system 100h with cassette 10h loaded.

Cassette 10h is simplified to a large extent because mating die plates 210a and 210b of machine 100h clamp together around cassette 10h to form the balance chamber portion, fluid heating pathways and other fluid flow paths of the cassette as installed. That is, the balance chamber portion, pathways, etc., do not have to preformed in cassette 10h prior to loading. The closing of door 202 against wall 220 of machine 100h instead forms the fluid-tight passageways mechanically. Cassette 10h is preformed as a pouch 212 as seen in FIG. 25B, which is made of three sheets 74a to 74c or two sheets 74a and 74b as necessary to form the desired components. Pouch 212 is connected fluidly to to-dialyzer line 152a, from-dialyzer line 152b, vent line 164, inlet connector 16, supply lines 18a to 18f and drainline 24 as seen further in FIG. 24b.

Die plate 210a is formed hinged door 202. Matching die plate 210b is formed on wall 220 of machine or system 100h. In the illustrated embodiment, die plate 210a includes heating pathway forming ridges 214a that mate with heating pathway forming ridges 214b of die plate 210b. Die plate 210a includes balance chamber forming ridges 216a that mate with balance chamber forming ridges 216b of die plate 210b. Die plates 210a and 210b also form or include tube/connector accepting grooves 218a and 218b, respectively, which secure tubes 152a, 152b, and 164 in place when door 202 is closed without crimping or closing the tubes. Die plates 210a and 210b alternatively or additionally form any other additional flexible sheeting apparatus discussed herein, such as volumetric pumping portions 70, UF meter portions internal flow paths 26, valve seats 28, etc.

At least one of die plates 210a and 210b is integrated with component activation, such as, a heater, pump actuator, balance chamber actuator and/or valve actuator. Heating is accomplished via electrical resistance plate heating, inductive heating, radiant heating and/or ultrasonic heating. FIG. 25A shows one embodiment of an in-line electrical resistance or plate heater configured to heat a fluid heating pathway formed by mechanical clamping. FIG. 25B shows a separate heater having heating pathway forming clamshell sides, the teachings of which are also applicable to system 100h. FIGS. 26A and 26B show a balance chamber portion of a flexible sheeting cassette formed via mechanical clamshell ridges, which can be activated pneumatically, mechanically, hydraulically or in the illustrated case electromagnetically. FIG. 28 shows a volumetric pump portion of a flexible sheeting cassette formed via mechanical clamshell ridges, which can also be activated pneumatically, mechanically, hydraulically or in the illustrated case electromagnetically. System 100h can integrate any of these technologies into one or more of die plates 210a and 210b.

In the illustrated embodiment, pouch 212 is shown without any inner seams, except those needed to seal to connectors, e.g., connector 16, and/or tubes 152a, 152b and 164. It is contemplated to alternatively provide internal safety seams to mitigate damage due to leaking. For example, a seam could be provided to separate the fluid pathway portion of pouch 212 from the balance chamber portion of the pouch. Another seam could be provided to separate or isolate balance chamber portion 50a from balance chamber portion 50b, and so on. The safety seams can have any desired shape or pattern but can advantageously be simpler than the shape or pattern needed to form the flow component portions outright. Safety seams can be between sheets 74a and 74b, 74b and 74c and between all three sheets 74a to 74c.

It is alternatively expressly contemplated to form the two sheet seals, for instance, between sheets 74a and 74b or 74b and 74c, using the bonding or welding methods described above to form the actual flow components having two-sheet seals. Mechanical clamshell sealing here is used anywhere that a seal between all three sheets 74a to 74c is needed. Here again, the overall number and pattern of the welds or bonds should be lessened and simplified, respectively.

Referring now to FIG. 25A, the heating portion of cassette 10h formed by mechanical clamping heating pathway forming ridges 214a and 214b is illustrated. Cassette 10h as shown in FIG. 25B includes a pouch 212, which receives fresh dialysate via fresh fluid inlet connector 16. Ridges 214a and 214b form an inline fluid heating pathway 42b, which receives the fresh fluid from inlet connector 16. Inline fluid heating pathway 42b serpentines back and forth as shown above to collect heat. Heated dialysate leaves through internal pathway 222, which is also formed via mechanical clamping. Heated fluid through pathway 222 travels to balance chambers 50a and 50b or to a volumetric pump 70 for example.

In the illustrated embodiment clamping ridges 214a and 214g are also heating elements, for example, aluminum plate heating elements. Further elements 224a and 224b are connected to door 202 and machine wall 202, which can also be electrical resistance elements. In one implementation, the heat actuator is a power supply that supplies power, e.g., 200 watts, to resistance elements 214a, 214b, 224a and 224b. Alternative types of heat actuators include inductive, radiant, connective, ultrasonic or a combination of heating types. Clamping ridges 214a and 214b can but do not have to be heat providing.

As illustrated, the heater using whatever type(s) of heat transfer is capable in one embodiment of heating dialysate starting from a temperature of about five to about thirty ° C. to a temperature of about thirty-seven ° C. or body temperature and at a flowrate of from zero to about three-hundred ml/min. A controller (not illustrated) within machine 100h controls a duty cycle or power on/power off cycle in one embodiment to accommodate different starting dialysate temperatures and different dialysate flowrates. The controller can be a delegate or subordinate processor operating with a supervisory processor and a safety processor. An outflow fluid temperature monitor 226 senses the temperature of dialysate leaving fluid heating pathway 42b and provides feedback to the controller to increase or decrease the duty cycle as needed to achieve the desired outflow temperature.

Referring now to FIG. 25B, a separable fluid heater 240 employing mechanical clamping to create a fluid heating pathway (e.g., like pathway 42a of FIGS. 1 and 3) within the separate heater 240 is illustrated. Separate fluid heater 240 can be used for example in system 100a of FIG. 1, system 100c of FIG. 3, and cassette 10f of FIGS. 22A and 22B. Heater 240 employs any of the types of heating in any combination discussed herein.

A fluid heating pouch 230 is connected to heater lines 38a and 38b through any method described herein. Materials for pouches 212, 230 include any of those for sheets 74a to 74c. Materials for tubes 38a and 38b include any of those for the tubing described herein. As seen, heating pouch 230 as formed is simpler than fluid heating pathway 42a of separate heater 40 of FIGS. 1 and 3.

Heater 240 in the illustrated embodiment includes a clamshell configuration, in which first and second heating enclosures 242 and 244 are connected hingedly together. When closed, heating path forming ridges 214a and 214b of enclosures 242 and 244, respectively, mate and clamp pouch 230. Enclosures 242 and 244 also form or include grooves 218a and 218*b*, respectively, which except lines 38*a* and 38*b*, respectively, allowing enclosures 242 and 244 to fit flushly together without crimping those lines.

Ridges 214*a* and 214*b* may or may not themselves be heating elements as described above in connection with FIG. 25A. Enclosures 242 and 244 in an embodiment each include a heating plate 246*a* and 246*b*, respectively. Heating plates 246*a* and 246*b* heat fluid within the crimped fluid heating pathway, for example, according to the temperatures and flowrates described above in connection with FIG. 25A.

Referring now to FIGS. 26A and 26B, an alternative apparatus and method for operating a balance chamber 250 is illustrated. One primary difference illustrated by FIG. 26A is that balance chamber 250 is driven magnetically and not via a separate pump as has been discussed previously. Middle sheet 74*b* includes outer plies 74*d* and 74*e*, which sandwich a layer ferromagnetic material 252, such as carbon or iron. Ferromagnetic material 252 is thin enough to allow middle sheet 74*b* to flex back and forth as necessary within a chamber formed by chamber forming members 102*a* and 102*b*. Outer plies 74*d* and 74*e* can be of any material listed above for sheets 74*a* to 74*c*. Alternatively, ferromagnetic material 252 is impregnated or interspersed, e.g., as a powder or grain, into a single ply sheet 74*b*. In any case, middle, moving sheet 252 needs to be compatible with sterile or near sterile medical fluids.

Balance chamber 250 is shown in operation with a portion of a dialysis machine 100 (e.g., 100*a*, 100*c*, 100*e*, 100*f* and 100*h*) operating with a cassette 10 (e.g., cassette 10*a*, 10*c*, 10*e*, 10*f* and 10*h*, respectively). Dialysis machine 100 includes or defines first and second chamber forming members 102*a* and 102*b*. For example, one of members of 102*a* or 102*b* is stationary and configured to accept flexible sheeting cassette 10 (e.g., formed in wall 220 of machine 100*h*), while the other of chamber forming members 102*a* or 102*b* is part of a door (e.g., door 202) that is closed onto the opposing side of flexible sheeting cassette 10 after it has been loaded into dialysis machine 100.

Electromagnets 254*a* and 254*b* in the illustrated embodiment are embedded within members 102*a* and 102*b*, respectively, creating a magnetic field around the chamber, which can be modulated and polarized to pull ferromagnetic sheet 74*b* to upper sheet 74*a* or lower sheet 74*c* of cassette 10. Electromagnets 254*a* and 254*b* are alternatively coiled around spherical chamber-creating members 102*a* and 102*b*, respectively, and are in any case provided with enough mass to operate balance chamber 250 as discussed below.

Electromagnets 254*a* and 254*b* are each connected via leads 256 and 258 to a controller 248. Controller 248 in one embodiment is a delegate or subordinate controller or printed circuit board ("PCB") that operates with a supervisory processor and a safety processor. Controller 248 in one embodiment also controls the valves operating with valve seats 28*j* to 28*m* (See FIGS. 1 and 3), which switch in synchronization with the switching of electromagnets 254*a* and 254*b*.

To polarize electromagnet 254*a*, controller 248 causes the leads 256 and 258 leading to electromagnet 254*a* to power that electromagnet. To polarize electromagnet 254*b*, controller 248 causes the leads 256 and 258 leading to electromagnet 254*b* to power that electromagnet. When electromagnet 254*a* is energized, ferromagnetic sheet 74*b* is pulled to the top of balance chamber 250. When electromagnet 254*b* is energized, ferromagnetic sheet 74*b* is pulled to the bottom of the chamber. In this manner, balance chamber 250 is self-powering or self-operating and provides a pumping function in addition to a metering function. A separate pump is not needed.

It is also contemplated that magnetically doped middle layer 74*b* also allows for the measurement of position of the layer. By oscillating the power to electromagnetic coils 254*a* and 254*b*, it is possible to read the current generated by the inertial movement of the layer in the electromagnetic coil when the coil is off. This information relates to or is dependent on the velocity of the middle, magnetically doped layer 74*b*. By integrating the velocity information it is possible to reliably determine position. This information can be used for determining flowrate out of or into the chamber and to determine when the chamber stroke has finished.

In the illustrated embodiment, chamber forming members 102*a* and 102*b* each define or include a port 104 to which a tube (not illustrated) is releasably or permanently secured via any of the methods and embodiments discussed herein. In an embodiment, after cassette 10 is loaded into machine 100, a static negative pressure or vacuum is drawn on ports 104, pulling first and third plies or sheets 74*a* and 74*c* against the inner at least substantially spherically shaped cavities defined by first and second members 102*a* and 102*b*. Flexible sheets 74*a* to 74*c* are made of a suitably stretchable, complaint, non-magnetic and leak-free material.

Although members 102*a* and 102*b* are shown defining at least substantially spherical shapes, other suitable cross-sectional shapes may be used, such as substantially triangular or substantially trapezoidal shapes. Further, although not illustrated, members 102*a* and 102*b* can define air channels that extend radially from ports 104 in various directions to help spread the vacuum across a larger surface of plies 74*a* and 74*c*. Once sheets 74*a* and 74*c* are pulled via vacuum against the inner surface of chamber forming members 102*a* and 102*b*, respectively, balance chamber 50 is ready for operation.

In one alternative embodiment, sheets 74*a* and 74*c* are rigid or semi-rigid and preformed having the, e.g., semicircular, chamber shape, making ports 104 and associated negative pressure unnecessary. In another alternative embodiment, electromagnets 254*a* and 254*b* and ferromagnetic sheet 74*b* are employed with a balance chamber that is re-used, i.e., is not disposable, so that outer sheets 74*a* and 74*c* are not needed. That is, magnetic actuation can be used with any type of balance chamber and is expressly not limited to a cassette-based or flexible sheeting cassette-based application as shown here.

FIG. 26A illustrates a state of operation in which no fluid has been delivered to balance chamber 250. In the illustrated embodiment, valve seat 28*l* is shown operating with a valve actuator 106, which is part of machine 100. Here, positive air pressure is applied to the port of actuator 106 to force a plunger 108 to compress valve seat 28*l* against second sheet 74*b*, closing balance chamber outlet 58*a*. Actuator 106 includes an o-ring seal 110, which creates a sliding seal between plunger 108 in the inner, e.g., cylindrical housing of valve actuator 106. To open balance chamber outlet 58*a*, a negative pressure is applied to port 106, pulling plunger 108 upwards against stop 112, enabling fluid to open seat 28*l* and flow outwardly from upper balance chamber compartment 54*a* through balance chamber outlet 58*a*.

In operation, to fill upper balance chamber compartment 54*a*, plunger 108 is pressurized, closing valve seat 28*l* and balance chamber outlet 58*a*. A similar valve actuator and plunger closes balance chamber inlet 56*a*. Electromagnet 254*a* is energized, pulling sheet 74*b* against upper sheet 74*a*. Next, the valve actuator and plunger operating with balance chamber inlet 56*a* is opened, electromagnet 254*a* is de-energized, electromagnet 254*b* is energized, pulling sheet 74*b* fully across the chamber and against lower sheet 74c, creating a vacuum and filling upper balance chamber compartment 54a.

To empty upper balance chamber compartment 54a and fill lower balance chamber compartment 54b, the valve actuator and plunger operating with balance chamber inlet 56a is closed, plunger 108 is pulled against stop 112, opening valve seat 28l and balance chamber outlet 58a, electromagnet 254b is de-energized, electromagnet 254a is energized, pulling sheet 74b fully across the chamber and against upper sheet 74a, dispelling fluid from balance chamber compartment 54a, through balance chamber outlet 58a and simultaneously creating a vacuum within balance chamber compartment 54b, filling such chamber. The cycle is then reversed using second balance chamber inlet 56b and second balance chamber outlet 58b (See FIG. 1) to dispel fluid from balance chamber compartment 54b and simultaneously fill balance chamber compartment 54a.

Because the volume defined by compartments 54a and 54b is fixed and because second sheet 74b is pushed all the way against upper and lower sheets 74a or 74c in each half stroke, the same volume of fluid is outputted through balance chamber outlets 58a and 58b in each half stroke. In this manner fresh and spent fluid balancing and UF removal can be readily and accurately controlled.

It is also contemplated to impregnate plungers 108 with a ferromagnetic material and open and close valve seats 28 electromagnetically.

Referring now to FIG. 26B, FIG. 26A is rotated ninety degrees about an access through ports 104 to show one embodiment for creating balance chamber seals via mechanical clamping crimping. Chamber forming members 102a and 102b each define or include a balance chamber crimping ridge or ring 216a and 216b (described above in connection with FIGS. 24A and 24B). Rings 216a and 216b in an embodiment extend around the circumference of balance chamber 50 or 250, except to allow for inlet and out let paths 56 and 58. Rings 216a and 216b crimp together to seal sheets 74a to 74c mechanically enough to withstand the positive and negative pressures and variations of same within the chamber. Clamping rings 216a and 216b operate with any type of balance chamber operation, e.g., via separate pump or electromagnetic operation.

An outer safety ring seal 72m may be provided optionally. Seal 72m is formed via any of the techniques discussed herein. It serves to mitigate the damage from any dialysate escaping the mechanical seal formed by mechanical rings 216a and 216b. It also allows for tolerance in aligning cassette 10 within machine 100.

Figure 27:
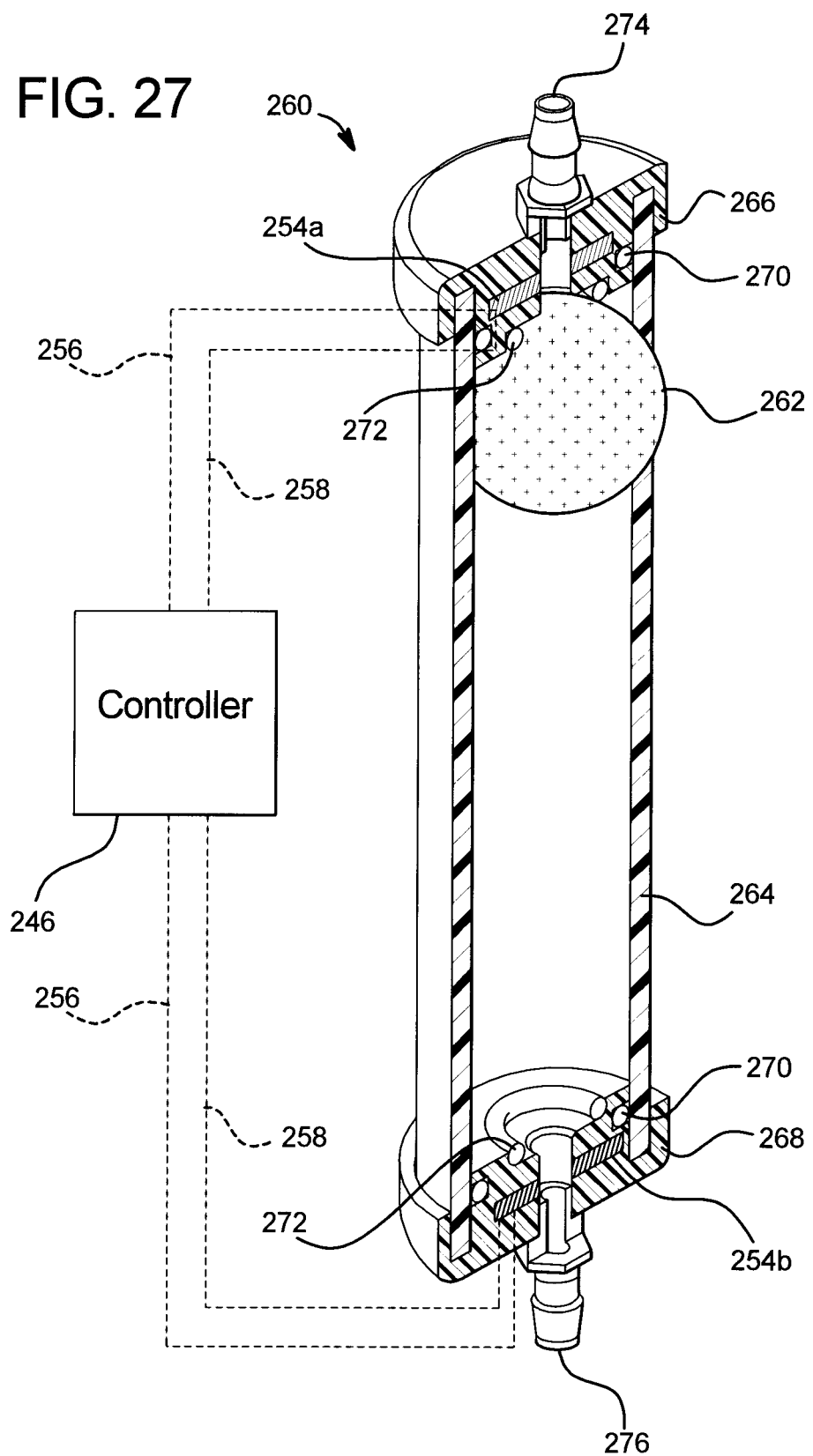
FIG. 27 illustrates a balancing tube or balancing piston driven by a magnetic field.

Referring now to FIG. 27, one embodiment of a magnetically driven balance tube 260 is illustrated. A balance tube is discussed in connection with FIG. 45 of the parent application. As discussed in the parent application, balance tube 260 here includes a separator 262, which functions similar to flexible membrane 74b of balance chamber 250. In the illustrated embodiment, separator 262 is a ball or spherical object that moves snuggly within a cylindrical housing 264. A pair of caps 266 and 268 are provided on either end of cylindrical housing 264. Caps 266 and 268 seal to cylindrical tubing 264 via outer O-rings 270. Separator or ball 262 seals to caps 266 and 268 via inner O-rings 272. In an alternative embodiment, caps 266 and 268 are permanently or hermetically sealed to cylindrical tube 264. Ports 274 and 276 are formed integrally with or are attached to caps 266 and 268, respectively. Ports 274 and 276 seal to mating tubes via any mechanism known to those with skill in the art.

Separator 262 is impregnated with a ferromagnetic material, such as carbon or iron. For example, a carbon core could be covered with a shell made of a medically safe material. Electromagnets 254a and 254b are in one embodiment embedded within caps 266 and 268, respectively, creating a magnetic field around separator 262, which can be modulated and polarized to pull ferromagnetic separator 262 to upper cap 266 or lower cap 268. Electromagnets 254a and 254b are each connected via leads 256 and 258 to a controller 248 described above. Electromagnets 254a and 254b are alternatively located outside of caps 266 and 268 and coiled instead around caps 266 and 268 and potentially end positions of tube 264. Here, the magnets can be housed within the machine as opposed to being located with in tube 260.

To polarize electromagnet 254a, controller 248 causes the leads 256 and 258 leading to electromagnet 254a to power that electromagnet. To polarize electromagnet 254b, controller 248 causes the leads 256 and 258 leading to electromagnet 254b to power that electromagnet. When electromagnet 254a is energized, ferromagnetic separator 262 is pulled to cap 266. When electromagnet 254b is energized, ferromagnetic separator 262 is pulled to cap 268. The movement of ball 262 pushes out and pulls in fresh/spent or spent/fresh fluid through port 274 or 276 upon each stroke. In this manner, balance tube 260 is self-powering or self-operating and provides a pumping function in addition to a metering function. A separate pump is not needed. As discussed above, magnetically impregnated separator 262 allows for its position to be determined within housing 264

In an embodiment, cylindrical tube 264 is translucent or transparent, so that an optical sensor can detect if ferromagnetic ball or separator 262 has properly reached the end of travel. Ultrasonic or other types of sensors may be used alternatively. Ferromagnetic ball or separator 262 is sized to fit snuggly but smoothly within the interior of cylinder 264. A small amount of mixing between fresh and effluent fluid may occur without substantially affecting the performance of the system. In an alternative embodiment, a cylindrical piston type separator is provided. In either case, ferromagnetic separator 262 may have additional sealing apparatus, such as wipers or deformable flanges that help to enhance the sliding or rolling seal as the case may be.

Balance tube 260 may be made of plastic or other suitable material. In an embodiment, balance tube 260 is a disposable item, which may be formed integrally with cassette 10 or attached to the cassette via tubing. O-rings and fittings may not be necessary if injection molded caps or assemblies are used. In addition, sensors such as ultrasonic or optical sensors, for the positioning of the separator can eliminate the need for sealing at the end of the tube.

Referring now to FIG. 28 an electromagnetically controlled volumetric pump 280 is illustrated. Volumetric pump 280 is shown operating with a dialysis machine 100, such as machine 100b (FIG. 2), which uses a cassette 10, such as cassette 10b (FIG. 2). Pump 280 can operate out of phase with a second electromagnetically controlled volumetric pump 280 in a manner discussed herein.

Machine 100 includes first and second pump chamber forming members 114a and 114b, which define the shape of the volumetric pump 280. Cassette 10 is configured to be loaded within the machine 100 such that a circular flexible membrane portion of cassette 10 is in alignment with the spherically shaped chamber defined by pump chamber forming members 114a and 114b. Although the spherical shape shown in FIG. 28 is one suitable shape, other shapes could be defined for volumetric pump 280, such as a trapezoidal or triangular shape. Also, valve seats 28q and 28s are aligned with valve actuators 106 as shown. Valve actuators 106 operate as described above in connection with FIG. 7 and include a plunger 108, which slides back and forth within the actuator body.

Pump 280 uses first and second flexible sheets 74a and 74b. Sheets 74a and 74b are each impregnated with a ferromagnetic material 252, such as an inner carbon or iron layer. Electromagnets 254a and 254b are embedded within pump chamber forming members 114a and 114b, respectively, creating a magnetic field around sheets 74a and 74b, which can both be energized to pull ferromagnetic sheets 74a and 74b apart to upper and lower members 114a and 114b, respectively. Alternatively, only one of electromagnets 254a and 254b is energized, pulling both sheets 74a and 74b towards that electromagnet. Electromagnets 254a and 254b are each connected via leads 256 and 258 to a controller 248 as described above. They can alternatively be located outside of an winding around members 114a and 114b.

In an initial state (shown in FIG. 28), electromagnet 254b is powered, which pulls first and second flexible sheets 74a and 74b to conform with the inner surface of lower chamber forming member 114b. Initially, a positive pressure is applied to both valve actuators 106, closing valve seats 28q and 28s. Again, valve actuators 106 can be any combination of pneumatically, mechanically, electrically and/or electromagnetically operated. As seen in FIG. 28, dialysate or medical fluid (including blood) 116 is pressurized against valve seat 28q, but is precluded from entering into the sealed chamber of volumetric pump 280.

In a second state, electromagnet 254b continues to be powered as is the positive pressure applied to valve actuator 106 at valve seat 28s. A negative pressure is applied to valve actuator 106 at valve seat 28q, which pulls and holds plunger 108 to and against stop 112, allowing fluid 116 to flow through pump inlet pathway 66b and into the chamber of volumetric pump 280. The force of fluid 116, e.g., via gravity may be enough to cause first flexible member 74a to be pushed against inner surface of upper pump chamber forming member 114a. Alternatively or additionally, electromagnet 254a is powered to pull first flexible sheet 74a against the inner surface of upper member 114a. This action causes a vacuum, which pulls fluid 116 into the pump chamber.

In a third state, valve seat 28q is closed, while valve seat 28s is opened. Power at electromagnet 254b is maintained, so that sheet 74b continues to be pulled against member 114b. Power is removed from electromagnet 254a causing electromagnet 254b to pull upper flexible sheet 74a against lower flexible sheet 74b at member 114b, which in turn causes fluid 116 to be pushed out of the at least substantially spherical chamber of volumetric pump 280, through pump outlet pathway 68b, to its desired destination. First and second membranes 74a and 74b are now at the initial state shown in FIG. 28, so that pump 280 is able to repeat the above described cycle as soon as valve seat 28s is closed.

Because the volume formed by the chamber of members 114a and 114b is known and because the flexible sheets are moved repeatedly to the upper and lower surfaces of the chambers, the volume of fluid pumped with each stroke is known and repeatable. Accordingly, a separate volumetric control apparatus, such as balance chamber 50 or 250, is not needed. The total volume of fluid pumped is equal to the volume of each stroke multiplied by the number of strokes. UF is controlled via one of the methods discussed above. As discussed above, magnetically impregnated sheet 74a and 74b allow for their position to be determined within chamber forming members 11245 and 114b.

Many embodiments have been described herein for different flexible sheeting cassettes having varying degrees and types of fluid flow components and functionality. The parent application for this application referenced herein includes many different embodiments for hemodialysis hemofiltration and hemodiafiltration systems. In particular, many embodiments are shown using dual dialzyers and a flow restriction between the dialyzers, which causes both diffusive and convective clearances associated with HHD. The flexible sheeting cassettes described herein may be used for each of the systems described in the parent application, including but not limited to: (i) the volumetric pump-based HCHDF systems of FIGS. 1, 4 and 5, which provide diffusive and convective clearance; (ii) the volumetric pump-based HF systems of FIGS. 6 and 7; (iii) the alternative volumetric pump-based HDF system of FIG. 8; (iv) the volumetric pump-based regeneration systems of FIGS. 9 to 11; (v) the peristaltic pump-based HDF and HF systems of FIGS. 12 and 13; (vi) the co-current flow system of FIG. 14; the pneumatically controlled system of FIGS. 15 and 16; (vii) the single balance chamber systems of FIGS. 17 to 22; (viii) the torturous path system of FIGS. 24 and 29, wherein the tortuous paths are formed between the sheets or plies 74a to 74u in any of the manners described above; (ix) the dual balance chamber systems of FIGS. 25 and 26; (x) the weight measurement system of FIGS. 30 and 31; the enhanced convection of HDF filter of FIG. 32; (xi) the linear tubing pump systems of FIGS. 38 to 41; and (xii) the fluid heater of FIGS. 42 and 43.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A hemodialysis system comprising:
   a dialyzer;
   a dialysate source;
   a dialysate pump;
   a dialysate cassette operatively connected to the dialysate pump such that the dialysate pump can pump dialysate through the dialysate cassette when the dialysate cassette is in fluid communication with the dialysate source, the dialysate cassette in fluid communication with the dialyzer;
   a blood pump; and
   a blood cassette operatively connected to the blood pump such that the blood pump can pump blood through the blood cassette, the blood cassette including a rigid housing and a flexible membrane attached to the rigid housing, the housing including a from-patient tube connector, a to-patient tube connector, a to-dialyzer tube connector, a from-dialyzer tube connector, and wherein the flexible membrane defines a valve seat for opening and closing a to-patient line of the blood cassette, the to-patient line in fluid communication with the to-patient tube connector.

2. The hemodialysis system of claim 1, which includes an internal air separation chamber connected fluidly to the from-dialyzer tube connector and the to-patient tube connector.

3. The hemodialysis system of claim 1, which further includes a tube connector for priming the blood cassette.

4. The hemodialysis system of claim 1, wherein the blood cassette is operably connected to the blood pump via a blood pumping tube extending outside of the rigid housing, the blood pumping tube connected fluidly to the from-patient tube connector and the to-dialyzer tube connector.

5. The hemodialysis system of claim 1, wherein at least one of the tube connectors is a tube port.

6. The hemodialysis system of claim 1, wherein the to-dialyzer tube connector is in operation located elevationally above the to-patient tube connector.

7. The hemodialysis system of claim 1, wherein the to-dialyzer tube connector is in operation located elevationally above the from-patient tube connector.

8. The hemodialysis system of claim 1, wherein the to-dialyzer tube connector is in operation located elevationally at the top of the blood cassette.

9. The hemodialysis system of claim 1, wherein at least one of the from-patient tube connector, to-patient tube connector, to-dialyzer tube connector, and from-dialyzer tube connector extends outwardly from an outer wall of the housing to accept the respective tube.

10. The hemodialysis system of claim 1, wherein the blood cassette further includes a blood pumping tube for operable connection to the blood pump.

11. The hemodialysis system of claim 10, wherein the blood pumping tube is a linear peristaltic blood pumping tube.

12. The hemodialysis system of claim 1, which includes at least one pressure sensor, and wherein the blood cassette further includes at least one pressure sensing area positioned and arranged for operable engagement with the at least one pressure sensor.

13. The hemodialysis system of claim 12, which includes arterial and venous pressure sensors and mating arterial and venous pressure sensing areas on the blood cassette.

14. The hemodialysis system of claim 1, wherein lines internal to the housing of the blood cassette are valved.

15. The hemodialysis system of claim 1, wherein the blood cassette and the dialysate cassette are integrated into a single cassette.

16. A hemodialysis system comprising:
a dialyzer;
a blood pump;
fresh and used dialysate pumps;
a blood cassette including a rigid housing and a flexible membrane attached to the rigid housing, the rigid housing including a blood pumping tube operatively connected to the blood pump for pumping blood through the blood cassette, the housing further including a from-patient tube connector, a to-patient tube connector, a to-dialyzer tube connector, a from-dialyzer tube connector, a valve seat defined by the flexible membrane for opening and closing a to-patient line of the blood cassette, the to-patient line in fluid communication with the to-patient tube connector, a fresh dialysate pumping tube operatively connectable to the fresh dialysate pump, and a used dialysate pumping tube operatively connectable to the used dialysate pump;
wherein the fresh and used dialysate pumps are operable with a dialysate cassette separate from the blood cassette, the dialysate cassette in fluid communication with the dialyzer; and
wherein at least one of the tube connectors is a tube port.

17. The hemodialysis system of claim 16, wherein the blood pumping tube, the fresh dialysate pumping tube and the used dialysate pumping tube are each linear peristaltic pumping tubes.

18. A hemodialysis system comprising:
a dialyzer;
a blood pump;
fresh and used dialysate pumps;
a cassette including a rigid housing and a flexible membrane attached to the rigid housing, the rigid housing including a blood pumping tube operatively connected to the blood pump for pumping blood through the cassette, the housing further including a from-patient tube connector, a to-patient tube connector, a to-dialyzer tube connector, a from-dialyzer tube connector, a valve seat defined by the flexible membrane for opening and closing a to-patient line of the cassette, the to-patient line in fluid communication with the to-patient tube connector, a fresh dialysate pumping tube operatively connectable to the fresh dialysate pump, and a used dialysate pumping tube operatively connectable to the used dialysate pump; and
wherein the cassette further includes a vent to vent air removed from blood within the cassette.

19. A hemodialysis system comprising:
a dialyzer;
a blood pump;
fresh and used dialysate pumps;
a cassette including a rigid housing and a flexible membrane attached to the rigid housing, the rigid housing including a blood pumping tube operatively connected to the blood pump for pumping blood through the cassette, the housing further including a from-patient tube connector, a to-patient tube connector, a to-dialyzer tube connector, a from-dialyzer tube connector, a valve seat defined by the flexible membrane for opening and closing a to-patient line of the cassette, the to-patient line in fluid communication with the to-patient tube connector, a fresh dialysate pumping tube operatively connectable to the fresh dialysate pump, and a used dialysate pumping tube operatively connectable to the used dialysate pump; and
wherein the cassette includes an air separation chamber formed within the housing.

20. A hemodialysis system comprising:
a dialyzer;
a blood pump; and
a blood cassette including a housing and a pumping tube, the pumping tube located outside of the housing and extending along a first side of the housing, the pumping tube operatively connected to the blood pump such that the blood pump in operation contacts the pumping tube for pumping blood through the cassette, the housing including a from-patient tube connector, a to-patient tube connector, a saline/priming tube connector, a to-dialyzer tube connector, a from-dialyzer tube connector, and wherein each of the connectors extends along a side of the housing different from the first side of the housing.

21. The hemodialysis system of claim 20, wherein each of the tube connectors extends along a side of the housing opposing the first side of the housing.

22. The hemodialysis system of claim 20, wherein at least one of the tube connectors is a tube port.

23. The hemodialysis system of claim 20, wherein each of the connectors is integral with and extends from the housing.

* * * * *